(12) United States Patent
Chinnaiyan et al.

(10) Patent No.: US 8,143,232 B2
(45) Date of Patent: Mar. 27, 2012

(54) GENE FUSION TARGETED THERAPY

(75) Inventors: Arul M. Chinnaiyan, Plymouth, MI (US); Jindan Yu, Ann Arbor, MI (US); Ram Shankar Mani, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 119 days.

(21) Appl. No.: 12/716,653

(22) Filed: Mar. 3, 2010

(65) Prior Publication Data

US 2010/0227910 A1    Sep. 9, 2010

Related U.S. Application Data

(60) Provisional application No. 61/156,957, filed on Mar. 3, 2009.

(51) Int. Cl.
*C12N 15/11*   (2006.01)
*C07H 21/02*   (2006.01)

(52) U.S. Cl. .......................................... 514/44; 536/24.5

(58) Field of Classification Search ........................ None
See application file for complete search history.

(56) References Cited

U.S. PATENT DOCUMENTS

| 2005/0014166 A1 | 1/2005 | Trono et al. |
| 2007/0212702 A1 | 9/2007 | Tomlins et al. |
| 2009/0208937 A1 | 8/2009 | Chinnaiyan et al. |

FOREIGN PATENT DOCUMENTS

WO   WO 03/070972   *  8/2003

OTHER PUBLICATIONS

GenBank Accession NM_001243433, Aug. 21, 2011.*
Mehra R. et al, "Comprehensive Assessment of TMPRSS2 and ETS Family Gene Aberrations in Clinically Localized Prostate Cancer," Mod Pathol. May 2007, vol. 20 , pp. 538-544.
Liu W. et al, "Multiple Genomic Alterations on 21Q22 Predict Various TMPRS S2/ERG Fusion Transcripts in Human Prostate Cancers," Gene Chromosomes Cancer, Nov. 2007, vol. 46, pp. 972-980.
Paoloni-Giacobino et al.,"Cloning of the TMPRSS2 Gene, Which Encodes a Novel Serine Protease With Transmembrane, LDLRA, and SRCR Domains and Maps to 21Q22.3," Genomics 44: 309 (1997).
Velasco et al., "Identification and Validation of Novel Androgen-Regulated Genes in Prostate Cancer," Endocrinology 145(8): 3913 (2004).
Lin et al., "Prostate-Localized and Androgen-Regulated Expression of the Membrane-Bound Serine Protease TMPRSS2," Cancer Research 59: 4180 (1999).
Tomlins et al., "Role of the RMPRSS2-ERG Gene Fusion in Prostate Cancer," Neoplasia, vol. 10, No. 2 pp. 177-188 (Feb. 2008).
Yu et al., Integrative Genomics Analysis Reveals Silencing of B-Adrenergic Signaling by Polycomb in Prostate Cancer, Cancer Cell 12, 419-431 2007A.
Barski et al., "High-Resolution Profiling of Histone Methylations in the Human Genome," Cell 129, 823-837 2007.
Johnson et al., "Genome-Wide Mapping of in Vivo Protein-DNA Interactions," Science (New York, NY) 316, 1497-1502 2007.
Mikkelsen et al., "Genome-Wide Maps of Chromatin State in Pluripotent and Lineage-Committed Cells," Nature 448, 553-560 2007.
Robertson et al., "Genome-Wide Profiles of STAT1 DNA Association Using Chromatin Immunoprecipitation and Massively Parallel Sequencing," Nature Methods 4, 651-657 2007.
Tomlins et al., "Recurrent Fusion of TMPRSS2 and ETS Transcription Facto Genes in Prostate Cancer," Science 310, 644-648 2005.
Tomlins et al.,"Distinct Classes of Chromosomal Rearrangements Create Oncogenic ETS Gene Fusions in Prostate Cancer," Nature 448, 595-599 2007.
Wang et al., "A Hierarchical Networkof Transcription Factors Governs Androgen Receptor-Dependent Prostate Cancer Growth," Molecular Cell 27, 380-392 2007.
Rhodes et al.,"Molecular Concepts Analysis Links Tumors, Pathways, Mechanisms, and Drgus," Neoplasia (New York, NY 9, 443-454 2007.
Tomlins et al., "Integrateive Molecular Concept of Prostate Cancer Progression," Nature Genetics 39, 41-51 2007.
Clark et al., "Complex Patterns of ETS Gene Alteration Arise During Cancer Development in the Human Prostate," Oncogene 27, 1993-2003 2008.
Demichelis et al., "TMPRSS2: ERG Gene Fusion Associated With Lethal Prostate Cancer in a Watchful Waiting Cohort," Oncogene 26, 4596-4599 2007.
Furusato et al., "ERG Oncoprotein Expression in Prostate Cancer: Clonal Progression of ERG-Positive Tumor Cells and Potential for ERG-Based Stratification," Mod Pathol 21, 67-75 2008.
Nam et al., "Expression of the TMPRSS2:ERG Fusion Gene Predicts Cancer Recurrence After Surgery for Localised Cancer," British Journal of Cancer 97, 1690-1695 2007.
Rajput et al., Frequency of the TMPRSS2: ERG Gene is Increased in Moderate to Poorly Differentiated Prostate Cancerm Journal of Clinical Pathology 60, 1238-1243 2007.
Wang et al., "Expression of Variant TMPRSSE/ERG Fusion Messenger RNAs is Associated With Aggressive Prostate Cancer," Cancer Research 66, 8347-8351 2006.

* cited by examiner

*Primary Examiner* — Richard Schnizer
(74) *Attorney, Agent, or Firm* — Casimir Jones, S.C.

(57) ABSTRACT

The present invention relates to compositions and methods for cancer therapy, including but not limited to, targeted inhibition of cancer markers. In particular, the present invention relates to recurrent gene fusions as clinical targets for prostate cancer.

9 Claims, 22 Drawing Sheets

1 taggcgcgag ctaagcagga ggcggaggcg gaggcggagg gcgaggggcg gggagcgccg 61 cctggagcgc ggcaggaagc cttatcagtt gtgagtgagg accagtcgtt gtttgagtgt 121 gcctacggaa cgccacacct ggctaagaca gagatgaccg cgtcctcctc cagcgactat 181 ggacagactt ccaagatgag cccacgcgtc cctcagcagg attggctgtc tcaaccccca 241 gccagggtca ccatcaaaat ggaatgtaac cctagccagg tgaatggctc aag TAGGCGCGAGCTAAGCAGGAiiiiiGGCGGAGGCGGAGGCGGAGGGCGAGGGGCG
GGGAGCGCCGCCTGGAGCGCGGCAG$^{75}$...G$^{76}$AAGCCTTATCAGTTGTGAGTGAGGi
iiiiACCAGTCGTTGTTTGAGTGTGCCTACGGAACGCCACACCTGGCTAAGACAG
AGATGACCGCGTCCTCCTCCAGCGACTATGGACAGACTTCCAAGATGAGCCCACG
CGTC
CCTCAGCAGGATTGGCTGTCTCAACCCCCAGCCAGGGTCACCATCAAAATGGAAT
GTAACCCTAGCCAGG
TGAATGGCTCAAG

US 8,143,232 B2

GENE FUSION TARGETED THERAPY

CROSS REFERENCE TO RELATED APPLICATIONS

This application claims priority to U.S. Provisional Patent Application Ser. No. 61/156,957, filed: Mar. 3, 2009, which is herein incorporated by reference in its entirety.

STATEMENT REGARDING FEDERALLY SPONSORED RESEARCH OR DEVELOPMENT

This invention was made with government support under grant numbers CA069568, CA129565 and CA111275 awarded by the National Institutes of Health and W81XWH-08-0031 awarded by the Army Medical Research and Material Command. The government has certain rights in the invention.

FIELD OF THE INVENTION

The present invention relates to compositions and methods for cancer therapy, including but not limited to, targeted inhibition of cancer markers. In particular, the present invention relates to recurrent gene fusions as clinical targets for prostate cancer.

BACKGROUND OF THE INVENTION

A central aim 1n cancer research is to identify altered genes that are causally implicated in oncogenesis. Several types of somatic mutations have been identified including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, Nat Rev Cancer 1: 245 (2001)). Recurrent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, Mutat Res 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, Nature 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, Nature 243: 290 (1973); de Klein et al., Nature 300: 765 (1982)). Importantly, this finding led to the rational development of imatinib mesylate (Gleevec), which successfully targets the BCR-ABL kinase (Deininger et al., Blood 105: 2640 (2005)). Thus, therapies that target recurrent gene rearrangements in common epithelial tumors are needed.

SUMMARY OF THE INVENTION

The present invention relates to compositions and methods for cancer therapy, including but not limited to, targeted inhibition of cancer markers. In particular, the present invention relates to recurrent gene fusions as clinical targets for prostate cancer.

For example, in some embodiments, the present invention provides a method of inhibiting the expression of an ERG gene in a cell, comprsing contacting the cell with an siRNA against ERG (e.g., an siRNA selected from, for example, SEQ ID NOs: 30-41). In some embodiments, the cell is a cancer cell (e.g, a prostate cancer cell). In some embodiments, the cell is in vivo. In some embodiments, the cell is in an animal (e.g., a human). In some embodiments, the cell is ex vivo. In some embodiments, the ERG gene is fused to TMPRSS2.

In further embodiments, the present invention provides a kit, comprising a pharmaceutical composition that inhbits the expression of an ERG gene in a cell, wherein the composition comprises a siRNA against ERG (e.g., an siRNA having a sequence selected from, for example, SEQ ID NOs: 30-41).

In other embodiments, the present inveniton provides methods and compositions that inhbit the expression of an ERG gene in a cell, comprising antisense, shRNA, miRNA, siRNA including blunt ends, overhangs, and miRNA therapies and method for their use.

Additional embodiments are described herein.

DESCRIPTION OF THE FIGURES

FIG. 26 shows the sequence of DQ204772 (TMPRSS2:ERG fusion) (SEQ ID NO: 43, upper sequence; SEQ ID NO: 44, lower sequence).

DEFINITIONS

Figure 1:
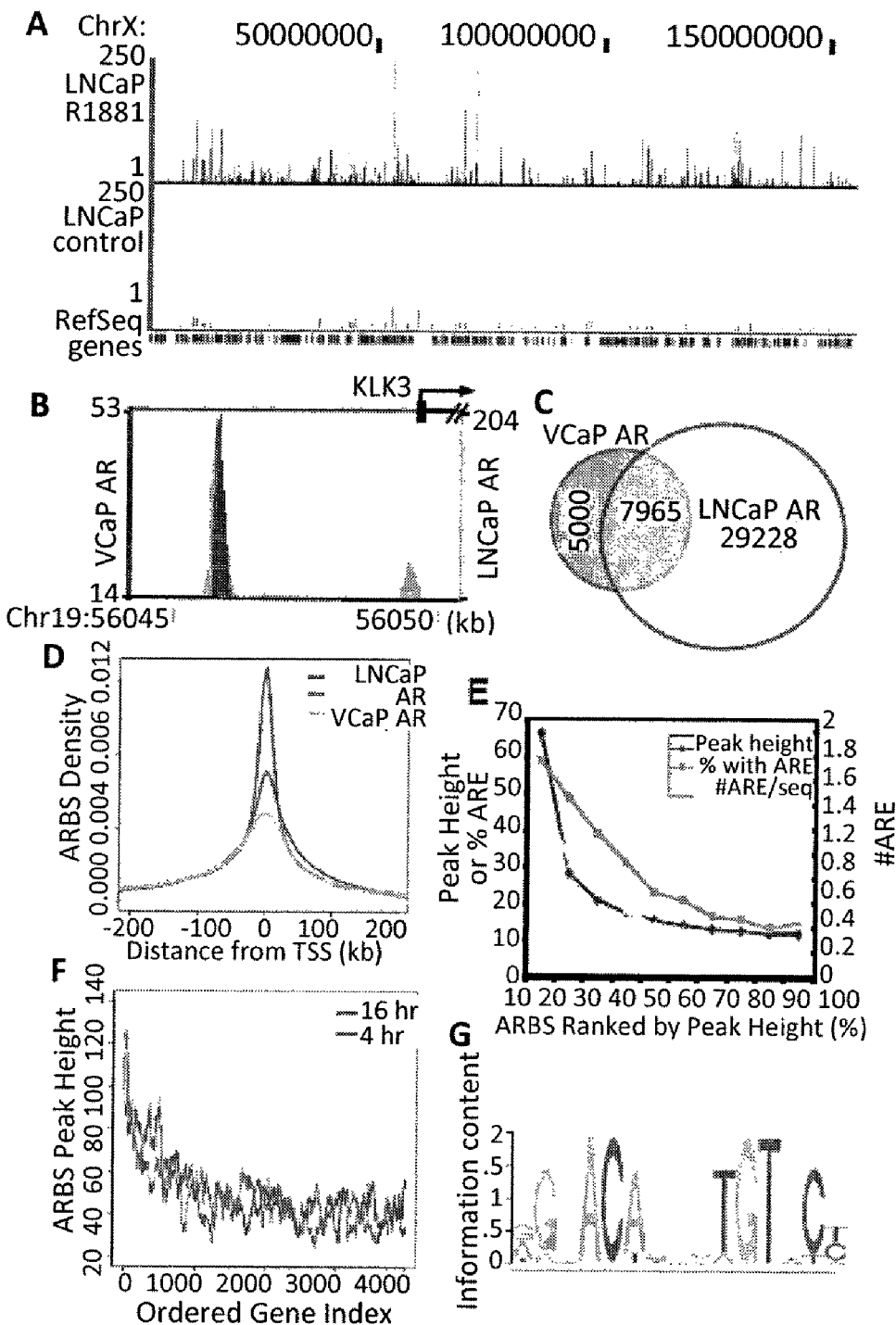
FIG. 1 shows the genomic landscape of AR binding in prostate cancer. (A) ChIP-Seq AR bound peaks on a representative chromosome. (B) Plot displays ChIP-Seq reads of AR binding on the KLK3 enhancer. (C) Venn diagram representing the overlap of AR-bound genomic regions derived from LNCaP and VCaP cells. (D) Distance of AR bound sites (ARBS) to the transcription start sites (TSS) of the closest genes. (E) The height of AR bound peaks is positively associated with the percentage of sequences that contains ARE motifs (% ARE) as well as the average number of AREs per peak region (#ARE). (F) The height of AR bound peaks is associated with androgen responsiveness (r=0.72 for 4 h and r=0.68 for 16 h). (G) The consensus motif present in AR bound regions identified by ChIP-Seq.

To facilitate an understanding of the present invention, a number of terms and phrases are defined below:

As used herein, the term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

As used herein, the terms "detect", "detecting" or "detection" may describe either the general act of discovering or discerning or the specific observation of a detectably labeled composition.

As used herein, the term "inhibits at least one biological activity of a gene fusion" refers to any agent that decreases any activity of a gene fusion of the present invention (e.g., including, but not limited to, the activities described herein), via directly contacting gene fusion protein, contacting gene fusion mRNA or genomic DNA, causing conformational changes of gene fusion polypeptides, decreasing gene fusion protein levels, or interfering with gene fusion interactions with signaling partners, and affecting the expression of gene fusion target genes. Inhibitors also include molecules that indirectly regulate gene fusion biological activity by intercepting upstream signaling molecules.

As used herein, the term "inhibits at least one biological activity of an ETS family member gene" refers to any agent that decreases any activity of an ETS family member gene (e.g., ERG) (e.g., including, but not limited to, invasion of cells expressing the ETS family member gene, as well as other activities described herein), via directly contacting the ETS family member protein, contacting the ETS family member mRNA or genomic DNA, causing conformational changes of ETS family member polypeptides, decreasing ETS family member protein levels, or interfering with ETS family member interactions with signaling partners, and affecting the expression of ETS family member target genes Inhibitors also include molecules that indirectly regulate ETS family member biological activity by intercepting upstream signaling molecules.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

The present invention relates to compositions and methods for cancer therapy, including but not limited to, targeted inhibition of cancer markers. In particular, the present invention relates to recurrent gene fusions as clinical targets for prostate cancer.

In some embodiments, the present invention provides therapeutics (e.g., nucleic acid based therapeutics or small molecule therapeutics) that target gene fusions. Gene fusions are described, for example, in U.S. patent application Ser. No. 11/825,552 and U.S. Patent Publication US-2007-0212702, each of which is herein incorporated by reference in its entirety. In some embodiments, therapeutics target TMPRSS2:ERG gene fusions. The present invention is not limited to a particular mechanism. Indeed, an understanding of the mechanism is not necessary to practice the present invention. Nonetheless, it is contemplated that targeting portions of gene fusions not found in the native genes (e.g., fusion junctions) that are found only in cancer cells will decrease side effects relative to targeting regions of genes found in all cells.

I. Gene Fusions

As described herein, embodiments of the present invention provide compositions and methods for inhibiting the activity of recurrent gene fusions associated with cancer (e.g., prostate cancer). In some embodiments, gene fusions are targeted as anti-cancer therapeutics. In some embodiments, the gene fusions are the result of a fusion between an androgen regulated gene or a housekeeping gene and an ETS family member gene.

A. Androgen Regulated Genes

Genes regulated by androgenic hormones are of critical importance for the normal physiological function of the human prostate gland. They also contribute to the development and progression of prostate carcinoma. Recognized ARGs include, but are not limited to: DDX5; TMPRSS2; PSA; PSMA; KLK2; SNRK; Seladin-1; and, FKBP51 (Paoloni-Giacobino et al., *Genomics* 44: 309 (1997); Velasco et al., *Endocrinology* 145(8): 3913 (2004)). Transmembrane protease, serine 2 (TMPRSS2; NM_005656), has been demonstrated to be highly expressed in prostate epithelium relative to other normal human tissues (Lin et al., *Cancer Research* 59: 4180 (1999)). The TMPRSS2 gene is located on chromosome 21. This gene is located at 41,750,797-41,801,948 bp from the pter (51,151 total bp; minus strand orientation). The human TMPRSS2 protein sequence may be found at GenBank accession no. AAC51784 (Swiss Protein accession no. O15393)) and the corresponding cDNA at GenBank accession no. U75329 (see also, Paoloni-Giacobino, et al., *Genomics* 44: 309 (1997)).

In some embodiments, gene fusions comprise transcriptional regulatory regions of an ARG. The transcriptional regulatory region of an ARG may contain coding or non-coding regions of the ARG, including the promoter region. The promoter region of the ARG may further contain an androgen response element (ARE) of the ARG. The promoter region for TMPRSS2, in particular, is provided by GenBank accession number AJ276404.

B. Housekeeping Genes

Housekeeping genes are constitutively expressed and are generally ubiquitously expressed in all tissues. These genes encode proteins that provide the basic, essential functions that all cells need to survive. Housekeeping genes are usually expressed at the same level in all cells and tissues, but with some variances, especially during cell growth and organism development. It is unknown exactly how many housekeeping genes human cells have, but most estimates are in the range from 300-500.

Many of the hundreds of housekeeping genes have been identified. The most commonly known gene, GAPDH (glyceraldehyde-3-phosphate dehydrogenase), codes for an enzyme that is vital to the glycolytic pathway. Another important housekeeping gene is albumin, which assists in transporting compounds throughout the body. Several housekeeping genes code for structural proteins that make up the cytoskeleton such as beta-actin and tubulin. Others code for 18S or 28S rRNA subunits of the ribosome. HNRPA2B1 is a member of the ubiquitously expressed heteronuclear ribonuclear proteins. Its promoter has been shown to be unmethylated and prevents transcriptional silencing of the CMV promoter in transgenes (Williams et al., BMC Biotechnol 5, 17 (2005)). An exemplary listing of housekeeping genes can be found, for example, in Trends in Genetics, 19, 362-365 (2003).

C. ETS Family Member Genes

The E-twenty six (ETS) family of transcription factors regulate the intra-cellular signaling pathways controlling gene expression. As downstream effectors, they activate or repress specific target genes. As upstream effectors, they are responsible for the spacial and temporal expression of numerous growth factor receptors. Almost 30 members of this family have been identified and implicated in a wide range of physiological and pathological processes. These include, but are not limited to: ERG; ETV1 (ER81); FLI1; ETS1; ETS2; ELK1; ETV6 (TEL1); ETV7 (TEL2); GABPα; ELF1; ETV4 (E1AF; PEA3); ETV5 (ERM); ERF; PEA3/E1AF; PU.1; ESE1/ESX; SAP1 (ELK4); ETV3 (METS); EWS/FLI1; ESE1; ESE2 (ELF5); ESE3; PDEF; NET (ELK3; SAP2); NERF (ELF2); and FEV. Exemplary ETS family member gene sequences are given in FIG. 9.

Ets Related Gene (ERG; NM_004449), in particular, has been demonstrated to be highly expressed in prostate epithelium relative to other normal human tissues. The ERG gene is located on chromosome 21. The gene is located at 38,675,671-38,955,488 base pairs from the pter. The ERG gene is 279,817 total bp; minus strand orientation. The corresponding ERG cDNA and protein sequences are given at GenBank accesssion no. M17254 and GenBank accession no. NP04440 (Swiss Protein acc. no. P11308), respectively.

The ETS translocation variant 1 (ETV1) gene is located on chromosome 7 (GenBank accession nos. NC_000007.11; NC_086703.11; and NT_007819.15). The gene is located at 13,708330-13,803,555 base pairs from the pter. The ETV1 gene is 95,225 by total, minus strand orientation. The corresponding ETV1 cDNA and protein sequences are given at GenBank accession no. NM_004956 and GenBank accession no. NP_004947 (Swiss protein acc. no. P50549), respectively.

The human ETV4 gene is located on chromosome 14 (GenBank accession nos. NC_000017.9; NT_010783.14; and NT_086880.1). The gene is at 38,960,740-38,979,228 base pairs from the pter. The ETV4 gene is 18,488 by total, minus strand orientation. The corresponding ETV4 cDNA and protein sequences are given at GenBank accession no. NM_001986 and GenBank accession no. NP_01977 (Swiss protein acc. no. P43268), respectively.

II. Therapeutic Applications In some embodiments, the present invention provides therapies for cancer (e.g., prostate cancer). In some embodiments, therapies directly or indirectly target gene fusions of the present invention.

A. RNA Interference and Antisense Therapies

In some embodiments, the present invention targets the expression of gene fusions. For example, in some embodiments, the present invention employs compositions comprising oligomeric antisense or RNAi compounds, particularly oligonucleotides (e.g., those described herein), for use in modulating the function of nucleic acid molecules encoding cancer markers of the present invention, ultimately modulating the amount of cancer marker expressed.

1. RNA Interference (RNAi)

In some embodiments, RNAi is utilized to inhibit fusion protein function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of fusion proteins. In some embodiments of the present invention, the siRNAs described by SEQ ID NOs: 30-41 are utilized.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001;15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually Comers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7 mers to 25 mers), where it is important to achieve a compromise between oligonucleotide length and binding affinity, to retain efficacy and target specificity (Sohail et al, Nucleic Acids Res., 2001; 29(10): 2041- 2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15): 4417-24, each of which is herein incorporated by reference in its entirety. In addition, software (e.g., the MWG online siMAX siRNA design tool) is commercially or publicly available for use in the selection of siRNAs.

In some embodiments, the present invention utilizes siRNA including blunt ends (See e.g., US20080200420, herein incorporated by reference in its entirety), overhangs (See e.g., US20080269147A1, herein incorporated by reference in its entirety), locked nucleic acids (See e.g., WO2008/006369, WO2008/043753, and WO2008/051306, each of which is herein incorporated by reference in its entirety). In some embodiments, siRNAs are delivered via gene expression or using bacteria (See e.g., Xiang et al., Nature 24: 6 (2006) and WO06066048, each of which is herein incorporated by reference in its entirety).

In other embodiments, shRNA techniques (See e.g., 20080025958, herein incorporated by reference in its interety) are utilized. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA polymerase III.

2. Antisense

In other embodiments, fusion protein expression is modulated using antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a gene fusion of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in PCT Publ. No. WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Hely. Chim. Acta 78:486 [1995]) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil(pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyloxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapy

The present invention contemplates the use of any genetic manipulation for use in modulating the expression of gene fusions of the present invention. Examples of genetic manipulation include, but are not limited to, gene knockout (e.g., removing the fusion gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter (e.g., an androgen-responsive promoter)).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subjects in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target prostate tumors that express a gene fusion. Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a gene fusion of the present invention, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments include agents such as a coagulant, a cytokine, growth factor, bacterial endotoxin or the lipid A moiety of bacterial endotoxin. For example, in some embodiments, therapeutic agents include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeting a cancer marker of the present invention (e.g., ERG fusions). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising pharmaceutical agents that modulate the expression or activity of gene fusions of the present invention). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

E. Combination Therapy

In some embodiments, the present invention provides therapeutic methods comprising one or more compositions described herein in combination with an additional agent (e.g., a chemotherapeutic agent). The present invention is not limited to a particular chemotherapy agent.

Various classes of antineoplastic (e.g., anticancer) agents are contemplated for use in certain embodiments of the present invention. Anticancer agents suitable for use with embodiments of the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of embodiments of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosfamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of embodiments of the present invention. For example, the U.S. Food and Drug Administration maintains a formulary of oncolytic agents approved for use in the United States. International counterpart agencies to the U.S.F.D.A. maintain similar formularies. The below Table provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |

| | | |
|---|---|---|
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino]tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)—N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-,3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O—(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |

-continued

| | | |
|---|---|---|
| Goserelin acetate (acetate salt of [D-Ser(But)⁶,Azgly¹⁰]LHRH; pyro-Glu-His-Trp-Ser-Tyr-D-Ser(But)-Leu-Arg-Pro-Azgly-NH2 acetate [C₅₉H₈₄N₁₈O₁₄•(C₂H₄O₂)ₓ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino-[1,2-b]quinoline-3,14(4H,12H) dione hydrochloride trihydrate) | Camptosar | Pharmacia & Upjohn Company |
| Letrozole (4,4'-(1H-1,2,4-Triazol-1-ylmethylene)dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride C₁₁H₁₂N₂S•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]-benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-µ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc (Mg₃Si₄O₁₀(OH)₂) | Sclerosol | Bryan, Corp., Woburn, MA |

-continued

| | | |
|---|---|---|
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo-[5,1-d]-as-tetrazine-8-carboxamide) | Temodar | Schering |
| Teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R—(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

III. Drug Screening Applications

In some embodiments, the present invention provides drug screening assays (e.g., to screen for anticancer drugs). The screening methods of the present invention utilize cancer markers identified using the methods of the present invention (e.g., including but not limited to, gene fusions of the present invention). For example, in some embodiments, the present invention provides methods of screening for compounds that alter (e.g., decrease) the expression of gene fusions. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method.

In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly prostate cancer.

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

Experimental

The following examples are provided in order to demonstrate and further illustrate certain preferred embodiments and aspects of the present invention and are not to be construed as limiting the scope thereof.

EXAMPLE 1

A. Experimental Procedures

Cell lines. The prostate cancer cell lines LNCaP and VCaP were obtained from the American Type Culture Collection, and grown in RPMI and DMEM-glutamax medium supplemented with 10% FBS, respectively. Benign immortalized prostate cell line RWPE with stable overexpression of GUS (RWPE+GUS) control and ERG (RWPE+ERG) (Tomlins et al., Neoplasia (New York, N.Y. 10, 177-188 2008) were grown in Keratinocyte serum-free medium supplemented with bovine pituitary extract. VCaP cells were infected with ERG or control (GUS) lentiviruses, and stable clones expressing ERG (VCaP+ERG) or GUS (VCaP+GUS) were selected for further analysis.

Chromatin immunoprecipitation (ChIP). ChIP was carried out as previously described (Yu et al., Cancer cell 12, 419-431 2007) using antibodies against AR (Millipore, #06-680), ERG (Santa Cruz, #sc354) and rabbit IgG (Santa Cruz, #sc-2027). For AR ChIP assays, LNCaP and VCaP cells were grown in phenol red-free medium with charcoal-stripped serum for hormone deprivation for 3 days, before treatment for 16 hr with 1% ethanol or 1OnM of methyltrienolone (R1881, NEN Life Science Products) dissolved in ethanol. AR ChIP was performed in paired ethanol-treated and R1881-treated samples. For ERG ChIP, LNCaP, VCaP, RWPE+ERG, and RWPE+GUS cells grown in corresponding regular medium were used.

ChIP-on-Chip analysis. ChIP-on-Chip was performed using the Agilent promoter arrays (−8 kb upstream to 2 kb downstream) as described previously (Yu et al., Cancer research 67, 10657-10663 2007). A scoring scheme across sliding windows was used to identity ChIP-enriched regions. For each probe, the 400 bp window surrounding this probe was considered and assigned a score by averaging the scaled log-ratio values (xDev, calculated from single-array error model by Agilent software) of all probes in the window surrounding that probe. To assign a P value for each score, the scores were assumed to be normally distributed and the variance and mean (likely close to zero) was estimated from a trimmed score set which excluded the top 5% and bottom 5% of the scores. A window with P-value <0.01 is determined as a ChIPenriched region which is further mapped to human genome to locate the nearest gene.

ChIP-Seq. ChIP samples were prepared for sequencing using the Genomic DNA sample prep kit (Illumina) following manufacturers protocols. ChIP-Sequencing was performed using Illumina Genome Analyzer according to standard manufacturer's procedures. The raw sequencing image data were analyzed by the Illumina analysis pipeline, aligned to the unmasked human reference genome (NCBI v36, hg18) using the ELAND software (Illumina) to generate sequence reads of 25-32 bps.

ChIP-Seq data analysis. It was first counted how many uniquely mapped reads are there in each sample and the ratio of the two counts was used as the normalizing factor to bring the total number of useable reads to the same level in both samples. Next each uniquely mapped read was extended directionally to form a 200bp hypothetical DNA fragment (HDF) in each sample. 200 is assumed to be the average length of size-selected DNA pieces during sample preparation (175-225 bp).

Under the null hypothesis of no enrichment in the stimulated sample versus unstimulated samples, reads from both samples are assumed to land on the genome following the same Poisson distribution (after corrected for the read counts in the unstimuated sample). The average sequencing depth across the whole genome is used as the background rate estimate r0. The probability of observing the read difference between two samples in each coverage region was calculated numerically. Using Bonferroni corrected p-value of 0.001, it was determined which coverage regions are significantly enriched.

HMM was applied to define where enriched regions start and end. To be specific, the entire genome was partitioned into 25 by bin and the read coverage is counted in each bin in the two samples. The two states are enriched region and background. The observed data are HDF coverage difference. In the enriched regions, it was expected that enrichment of HDFs would be present in the stimulated sample but not in the unstimulated samples. Therefore the differences are assumed to be the result of two different Poisson distributions with rates r1 and r2, r1>r2. In background, the differences are assumed to come from two identical Poisson distribution with rate r0. The transition probabilities are estimated empirically. From the output of HMM, regions are selected based on posterior probability of being in the enriched regions. Out regions whose maximum read count in a bin does not exceed the threshold corresponding to Bonferroni corrected p-value of 0.001 calculated using differences of two Poisson distributions with background rate r0 are filtered out.

Binding sites motif analysis. Searching for known transcription factor binding sites (TFBS) was performed using the Matlnspector package (Cartharius et al., Bioinformatics (Oxford, England) 21, 2933-2942 2005) (Genomatix Software, GmbH, Munich, Germany). To identify over-represented TFBSs, motif scan was performed in both ChIP-enriched regions as well as control sequences which are obtained by randomly shuffling all bases in the original ChIP-enriched regions. The significance of over-representation of each TFBS in these two types of regions is measured by the p-value of Fisher's exact tests. The same default threshold in MatInspector for motif searching was used on all sequences and all 508 individual vertebrate TFBS matrices. De novo motif finding was performed using MEME (Bailey and Elkan, 1994). 128 sequences that are overlapped in both LNCaP and VCaP cells and are within 50 kb upstream of genes shown differential expression under the treatment of AR were used.

Gene expression profiling analysis. VCaP cells were hormone starved for 2 days and treated with 1% ethanol or 10 nM R1881, or infected with LacZ control adenovirus or ERG adenovirus. Total RNA was isolated using Trizol (Invitrogen) followed by purification using Qiagen RNeasy kit (Qiagen). Expression profiling was performed using the Agilent Whole Human Genome Oligo Microarrays according to the manufacturer's protocols (Agilent).

A time-course gene expression dataset profiling starved LNCaP cells subjected to DHT treatment for 0, 4 and 16 h using Affymetrix GeneChip Human Genome U133 Plus 2.0 Arrays was downloaded from NCBI GEO database (GSE7868). The raw CEL data were analyzed using the RMA algorithm (Irizarry et al., Biostatistics (Oxford, England) 4, 249-264 2003) with the newest probe mapping, and the bayesian regularized t statistic (Baldi and Long, Bioinformatics (Oxford, England) 17, 509-519 2001) was used to calculate the level of differential expression at each time point relative to 0 h.

Sequence conservation analysis. The AR enriched regions were identified by Chip-Seq and aligned at their center. The phastCons scores (Siepel et al., Genome research 15, 1034-1050 2005) were retrieved and averaged at each position.

Gene set enrichment analysis (GSEA). Expression profiling data of AR-treated VCaP, ERG adenovirus infected VCaP and control cells were generated by Agilent whole human genome arrays. Gene expression fold changes in experimental cells relative to controls were calculated and genes having at least 4 fold changes in AR-treated cells were defined as AR-regulated gene set. Gene expression fold changes in ERG adenovirus infected VCaP cells relative to controls were used to pre-rank genes and imported into GSEA program (Subramanian et al., Proceedings of the National Academy of Sciences of the United States of America 102, 15545-15550 2005) to examine if AR-regulated gene set is enriched in the data.

Quantitative PCR. Q-PCR was performed using Power SYBR Green Mastermix (Applied Biosystems) on an Applied Biosystems 7300 Real Time PCR machine as previously described (Yu et al., Cancer cell 12, 419-431 2007a). All primers were designed using Primer 3 and synthesized by Integrated DNA Technologies and are listed in Table 8. All PCR experiments were performed in triplicates.

Co-Immunoprecipitation and Western blotting. VCaP cells grown in DMEMglutamax (Invitrogen, Carlsbad, Calif.) supplemented with 10% FBS to 80% confluence. Cells were harvested with or without formaldehyde crosslinking, and nuclei were isolated subsequently. After washing with TBS twice, nuclei were lysed and sonicated in RIPA buffer containing protease inhibitors (Roche applied science, Indianapolis, Ind.). The lysate was centrifuged and used for co-immunoprecipitation with antibodies. Antibodies used for immunoprecipitation were: anti-AR (polyclonal (PG21), Millipore); anti-ERG (polyclonal, Santa Cruz), control antibody (Rabbit IgG polyclonal, Millipore). Mouse monoclonal anti-AR antibody (AR441) from Labvision (Thermo scientific, Fremont, Calif.) was used for Western experiment.

RNA interference. VCaP cells were treated with non-targeting siRNA (D-001210-01, Dharmacon), siRNA specific to both isoforms of ERG (D-003886-01, Dharmacon), TMPRSS2-ERG fusion transcript, and wild-type-ERG (UGG UCA GAG AGA AGC AAU A; SEQ ID NO: 42).

Cell growth and WST cell proliferation assay. VCaP cells were grown in 24 well plates ($5 \times 10^4$ cells/well) in DMEM-glutamax (Invitrogen, Carlsbad, Calif.) medium. The cells were deprived of androgen for 48 h in phenol red-free DMEM containing 10% charcoal stripped FBS before infection by adeno-ERG virus or adeno-LacZ control virus (Tomlins et al., Neoplasia (New York, N.Y.) 10, 177-188 2008). R1881 dissolved in ethanol was used at a final concentration of 1 nM. Assays were performed after 48 h of treatments. For cell count assay, cells were trypsinized and counted using Z2 Coulter particle counter and size analyzer (Beckman Coulter, Fullerton, Calif.). Cell proliferation assay with WST-1 reagent was performed following the manufacturer's instructions (Roche applied science, Indianapolis, Ind.). The reaction was performed on the 24 well culture plate and the solution was transferred to 96-well plate for reading using SpectraMax M5 plate reader (Molecular Devices, Sunnyvale, Calif.).

Cell Invasion assay. Cell invasion was carried out using a modified basement membrane chamber assay as previously described (Yu et al., Cancer cell 12, 419-431 2007a). Briefly, equal numbers of the indicated cells were seeded onto the basement membrane matrix (EC matrix, Chemicon) present in the insert of a 24-well culture plate, with fetal bovine serum added to the lower chamber as a chemoattractant. After 48 h, non-invading cells and the EC matrix were removed by a cotton swab. Invaded cells were stained with crystal violet and photographed. The inserts were treated with 10% acetic acid and absorbance was measured at 560 nm.

B. Results

Figure 8:
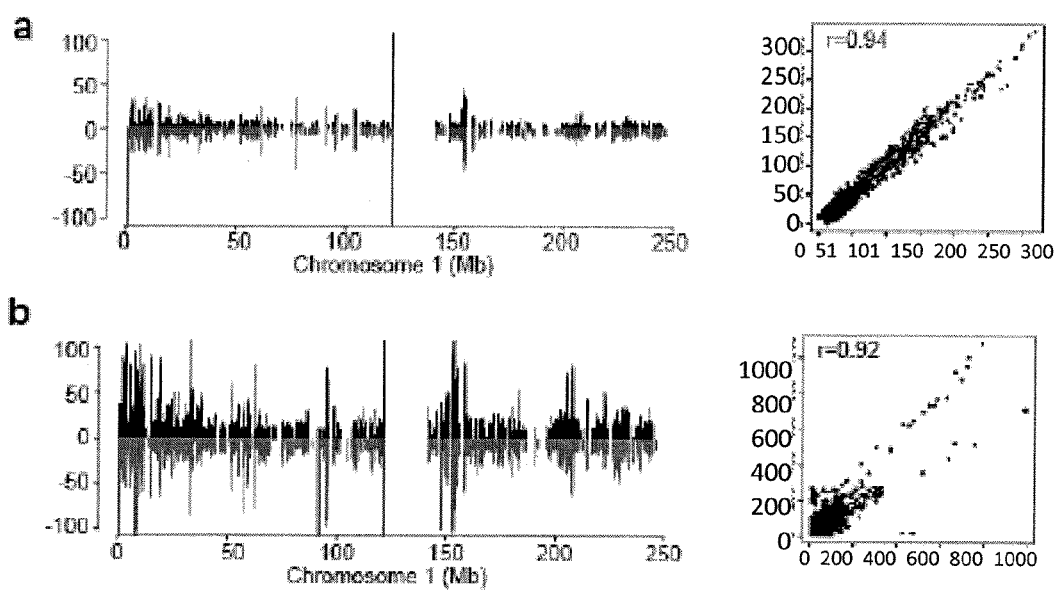
FIG. 8 shows the technical and biological reproducibility of ChIP-Seq. (A) reproducibility between technical replicates (black upward peaks vs. red downward peaks) of the same ChIP-Seq sample. b, reproducibility between ChIP-Seq analysis of two biological samples that were derived from separate ChIP and sample preparations.

Genomic landscape of AR occupancy. Taking advantage of the emerging ChIP-Seq technology (Barski et al., Cell 129, 823-837 2007; Johnson et al., Science (New York, N.Y. 316, 1497-1502 2007; Mikkelsen et al., Nature 448, 553-560 2007; Robertson et al., Nature methods 4, 651-657 2007), genomic regions bound by AR in two androgen-sensitive prostate cancer cell lines were determined. These included VCaP cells, which harbor the most common prostate cancer gene fusion TMPRSS2-ERG (Tomlins et al., Science 310, 644-648 2005), and LNCaP cells that are negative for ERG fusions but positive for a cryptic rearrangement of ETV1 (Tomlins et al., Nature 448, 595-599 2007). In order to define enriched genomic regions in ChIP-Seq experiments HPeak, a program applying a Hidden Markov Model-based algorithm for ChIP-Seq peak finding was used. The results demonstrated high reproducibility between technical and biological replicates of ChIPSeq experiments (FIG. 8). In the absence of androgen there is a very low level of basal AR binding activity, while upon androgen treatment AR binds to approximately 10-fold more genomic regions and with stronger enrichment (FIG. 1A, Table 1). After normalization to corresponding ethanol treated control samples using HPeak, a total of 37,439 and 12,965 AR binding peaks were detected in the androgen-treated LNCaP and VCaP cells, respectively.

Figure 9:
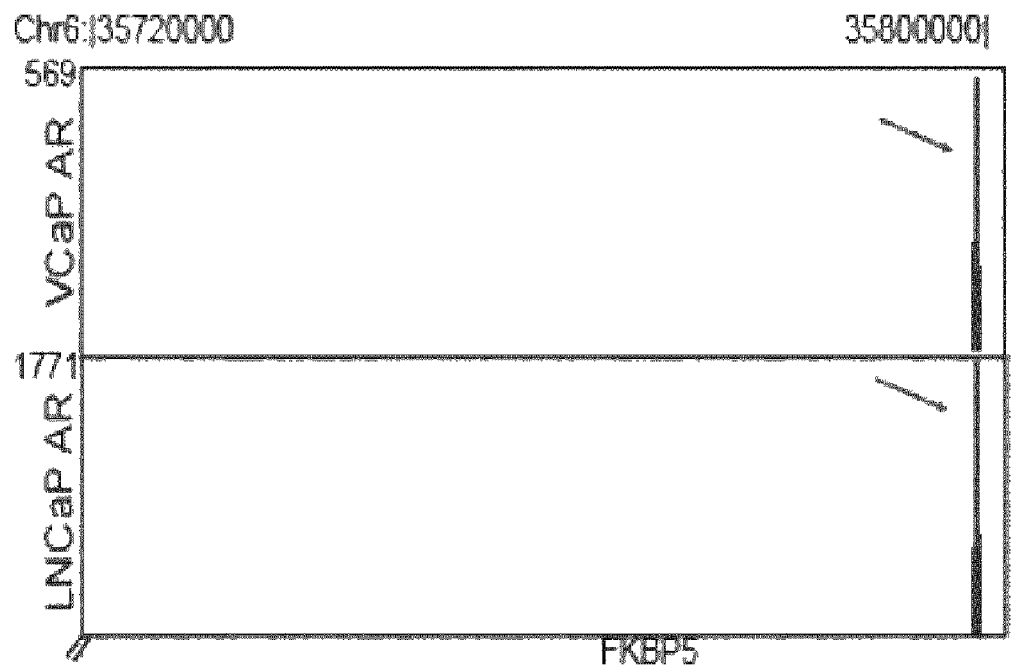
FIG. 9 shows AR ChIP-Seq binding peaks on FKBP5 enhancer.

A large number of previously reported AR target genes were identified. For example, FKBP5 is known to be regulated by AR via a distal enhancer (Magee et al., Endocrinology 147, 590-598 2006), and has been previously detected by ChIP-on-Chip as a top AR target gene (Bolton et al., Genes & development 21, 2005-2017 2007). FKBP5 was identified as the best target gene in both LNCaP and VCaP cells, with the highest number of reads mapped in single 25 bp sliding window being 1771 and 669, respectively (FIG. 9). In addition, a sharp ChIP-Seq AR binding peak was detected at the well-defined enhancer of the PSA gene, whereas a minor second peak was found at the PSA promoter (Jia and Coetzee, Cancer research 65, 8003-8008 2005) (FIG. 1B). Furthermore, a comparison of AR-bound regions between LNCaP and VCaP cells revealed a marked overlap; approximately 61% of AR bound genomic regions in VCaP cells, at a resolution of 25 bp window defined by HPeak, also recruit AR in LNCaP cells (FIG. 1C). Taken together, these results validate the accuracy of the ChIP-Seq assay in identifying AR binding sites.

Previous studies of a limited number of genes advocate AR regulation of target genes through distant enhancers (Bolton et al., 2007, supra). To evaluate the pattern of AR occupancy at the genome-scale, the distance of the midpoint of AR bound regions to the Transcription Start Sites (TSS) of the nearest genes was assessed. Only 5% of all AR bound regions identified in LNCaP cells locate within the proximity of TSS of target genes (Table 2). While some binding sites are over 100 kb upstream of TSS, approximately 50% of AR binding sites are within intragenic regions, indicating a diversity of androgen regulatory mechanisms mediated by promoter, enhancer, or intragenic elements. A much higher proportion (14%) of AR bound sites are within the promoter regions in VCaP cells as opposed to LNCaP cells (FIG. 1D), indicating a cell line-specific promoter-mediated regulation of target genes in VCaP cells that harbor TMPRSS2-ERG gene fusion.

Motif analysis of AR binding sites. To determine the preferred consensus binding sequences of AR, AR bound regions identified by ChIP-Seq were examined for the occurrence of all 508 pre-defined consensus sequence matrices of vertebrate transcription factors in the Genomatix database using MatInspector. This screen found the 15-bp canonical ARE as the most significantly enriched motif in AR binding sites (Table 3); up to 36.1% AR binding peaks from LNCaP and 33.2% from VCaP contain at least one ARE site (Table 4). The occurrence of ARE sites is positively correlated (r=0.87, P<0.001) with AR enrichment indicated by the height of AR binding peaks; up to 60% of the AR binding sites ranked in the top 10% by peak height contain AREs (FIG. 1E). Furthermore, some AR binding peaks contain more than one ARE, and the average number of ARE sites per peak is also positively correlated (r=0.93, P<0.001) with peak height, further confirming the importance of ARE sites in recruiting the transcription factor. Analysis of AR binding sites in androgen-regulated genes defined by gene expression profiling (Wang et al., Molecular cell 27, 380-392 2007) revealed a positive correlation (r=0.72, P<0.001) between peak height and androgen responsiveness (FIG. 1F).

Besides ARE sites, motif scan of AR bound sequences identified significant (P<1×10$^{-158}$ by Fisher's exact test) enrichment of binding motifs of other transcription factors (Table 3) including previously characterized AR co-factors, such as the Forkhead transcriptional factors (Heemers and Tindall, Endocrine reviews 28, 778-808 2007). ETS family binding motifs were found to be the 2nd most significantly (P<1×10$^{-300}$ by Fisher's exact test) enriched motif; approximately 29% of AR binding peaks in VCaP and 27% in LNCaP contain ETS sites, comparable to the 33% and 36% occurrence rate of ARE sites, respectively (Table 4). This result suggests that AR and the ETS gene fusion product ERG may bind to a common set of sequences, especially in cells that express both TMPRSS2-ERG and AR, such as the VCaP cells. To further confirm the co-localization of AR and ERG binding motifs, a subset of 1,422 AR bound regions that contain both the ARE and ETS sites were analyzed. In 51% of these sequences ARE and ETS motifs are within 50 by to each other.

Figure 10:
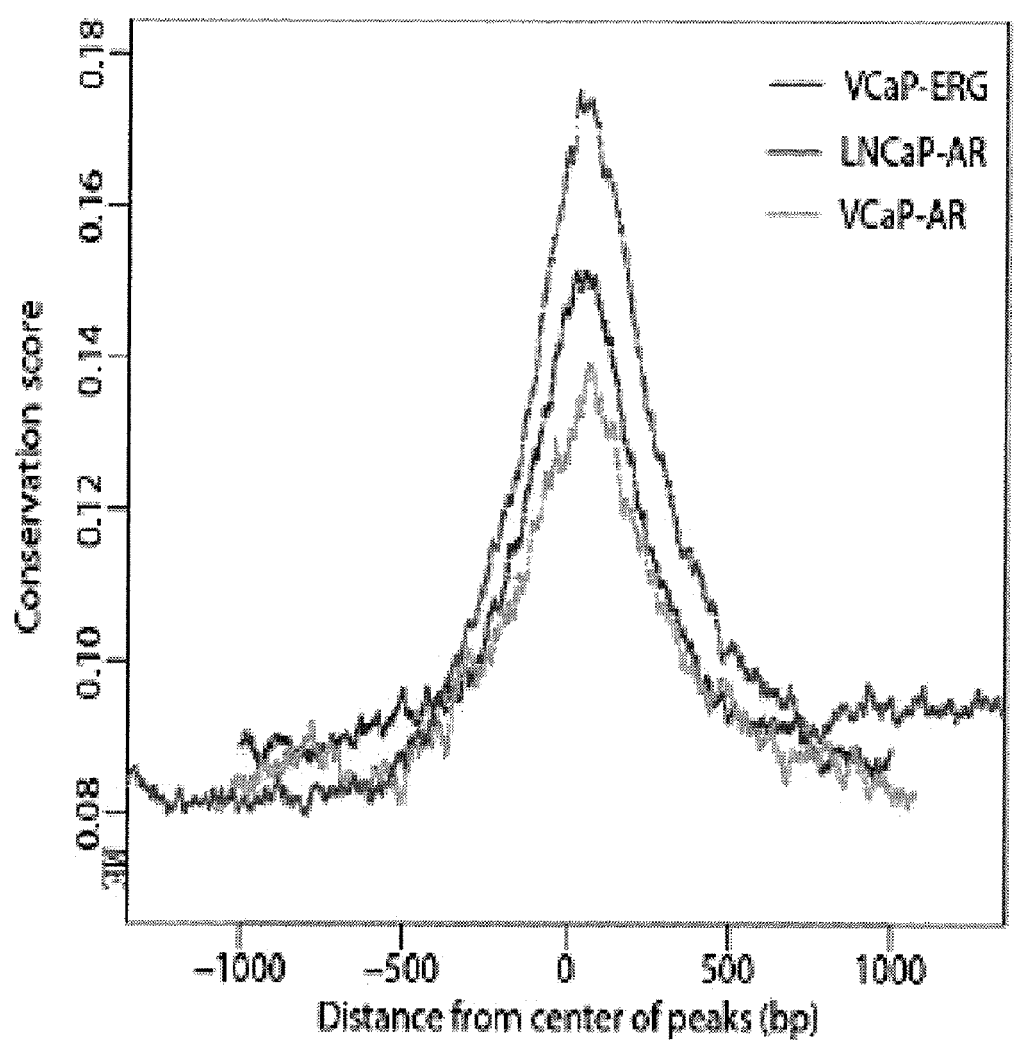
FIG. 10 shows conservation of transcription factor binding sites between human, mouse and another 15 vertebrate genomes.

It was next investigated whether ChIP-Seq data could be useful to predict unknown consensus motifs of the corresponding transcription factors. First, the analysis of AR bound sequences across species showed high conservation at the center of the peaks, being consistent with the notion that transcription factor binding loci are often phylogenetically conserved (FIG. 10). Next, de novo motif search by the MEME (Multiple Em for Motif Elicitation) Program in a subset of 128 AR binding peaks that overlap between LNCaP and VCaP, and also map to androgen-responsive genes (Wang et al., Molecular cell 27, 380-392 2007) identified a frequently occurring consensus motif, which was named "memeARE", that has marked similarities to the canonical ARE sites (FIG. 1G).

Figure 11:
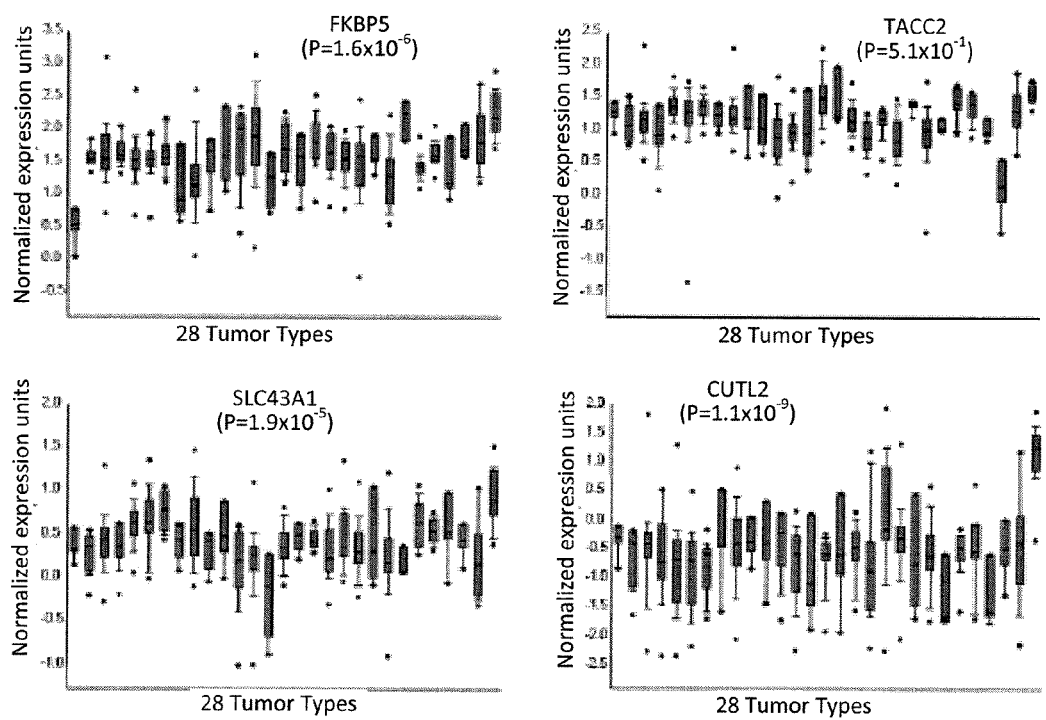
FIG. 11 shows prostate tissue specificity of top AR-bound genes.

AR binding correlates with gene expression. To study the association between AR binding and androgen regulation of gene expression, top AR bound genes were examined. Besides FKBP5, the additional top 5 targets in LNCaP cells are C6ORF81, TACC2, CUTL2 and SLC43A1, all of which are also included in the top 10 AR bound targets in VCaP cells. All of these genes except C6ORF81, an uncharacterized transcript, showed marked overexpression in prostate cancer relative to other tumor types in a large multi-tumor microarray data set (FIG. 11), indicating that these genes are relatively "prostate specific".

Figure 2:
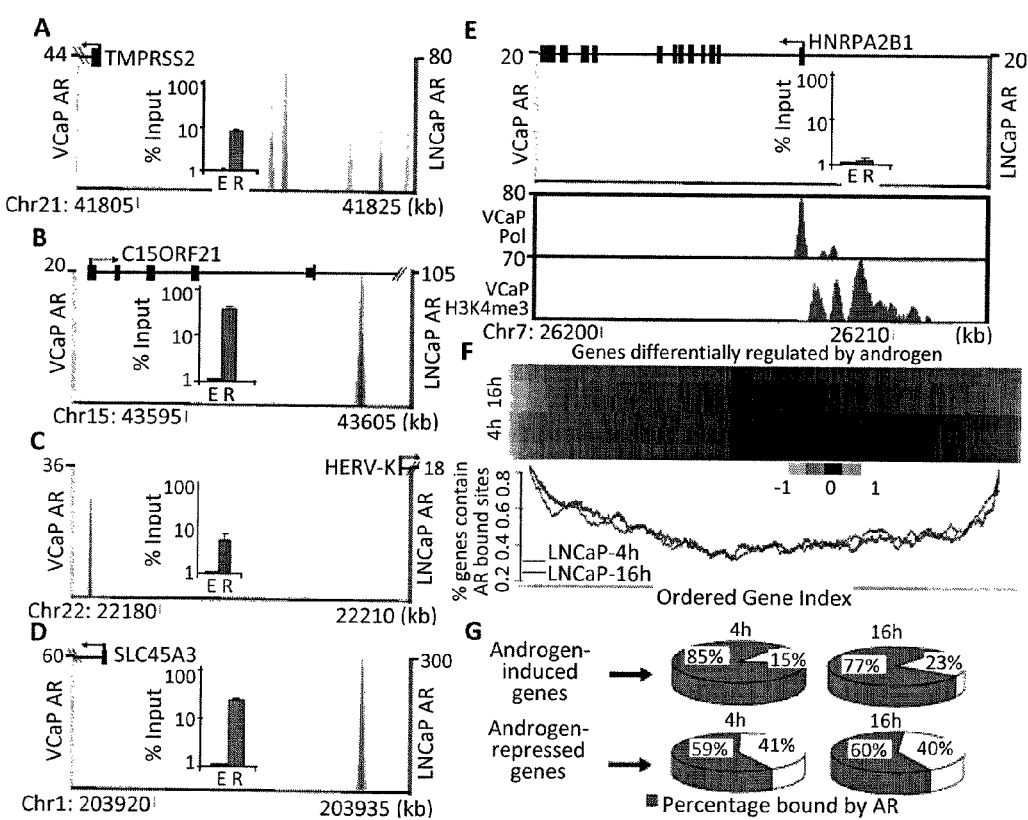
FIG. 2 shows AR binding on 5' fusion partners of prostate cancer and its correlation with androgen-mediated gene expression. (A-E) AR bound peaks at regulatory regions of previously characterized 5' fusion partners in prostate cancer. Plots are denoted as in FIG. 1B. On the Y-axes are the number of reads in each 25 bp sliding window in VCaP (left) and LNCaP (right). Inset represents validation by conventional ChIP-PCR of AR binding (measured as percentage of input) on target genes in LNCaP cells that have been hormone-deprived for 3 days and treated with either ethanol (E) or R1881 (R) for 16 h. Below the plot of (E) are PolII- and H3K4me3-enriched ChIPSeq peaks at the corresponding region for the androgen-insensitive house-keeping gene, HNRPA2B1. (F) Correlation between androgen-regulated gene expression and AR binding. Top panel: androgen-induced or -repressed genes ranked by t-statistics at 4 h and 16 h after androgen stimulation relative to 0 h in LNCaP prostate cancer cells. Bottom panel: the (4 h) and (16 h) curves represent the 500-gene moving averages of the fraction of differentially expressed genes that have at least one ChIP-Seq AR bound sites within its intragenic region or 50 kb upstream of their TSS. (G) Percentage of androgen-induced or -repressed genes that contain at least one AR bound site.

To confirm AR binding in the context of recurrent gene fusion, AR occupancy on previously reported 5' gene fusion partners in prostate cancer was examined. AR binds the regulatory elements of all 5' fusion partner genes that are androgen sensitive including TMPRSS2, C15ORF21, HERV-K, and SLC45A3 (Tomlins et al., Nature 448, 595-599 2007) (FIG. 2A-D). Moreover, conventional ChIP-PCR using primers specific to each target gene confirmed AR binding detected by ChIP-Seq assay (FIG. 2A-D inset). By contrast, no AR occupancy was detected within the regulatory regions of HNRPA2B1, a 5' fusion partner which is not androgen sensitive but is ubiquitously expressed (Tomlins et al., Nature 448, 595-599 2007), a feature that may have led to the upregulation of the fusion product (FIG. 2E). ChIP-Seq analysis using antibodies against RNA PolII and Histone H3 Lysine 4 trimethylation (H3K4me3) confirmed the active and open chromatin structure of the HNRPA2B1 promoter (FIG. 2E).

Figure 12:
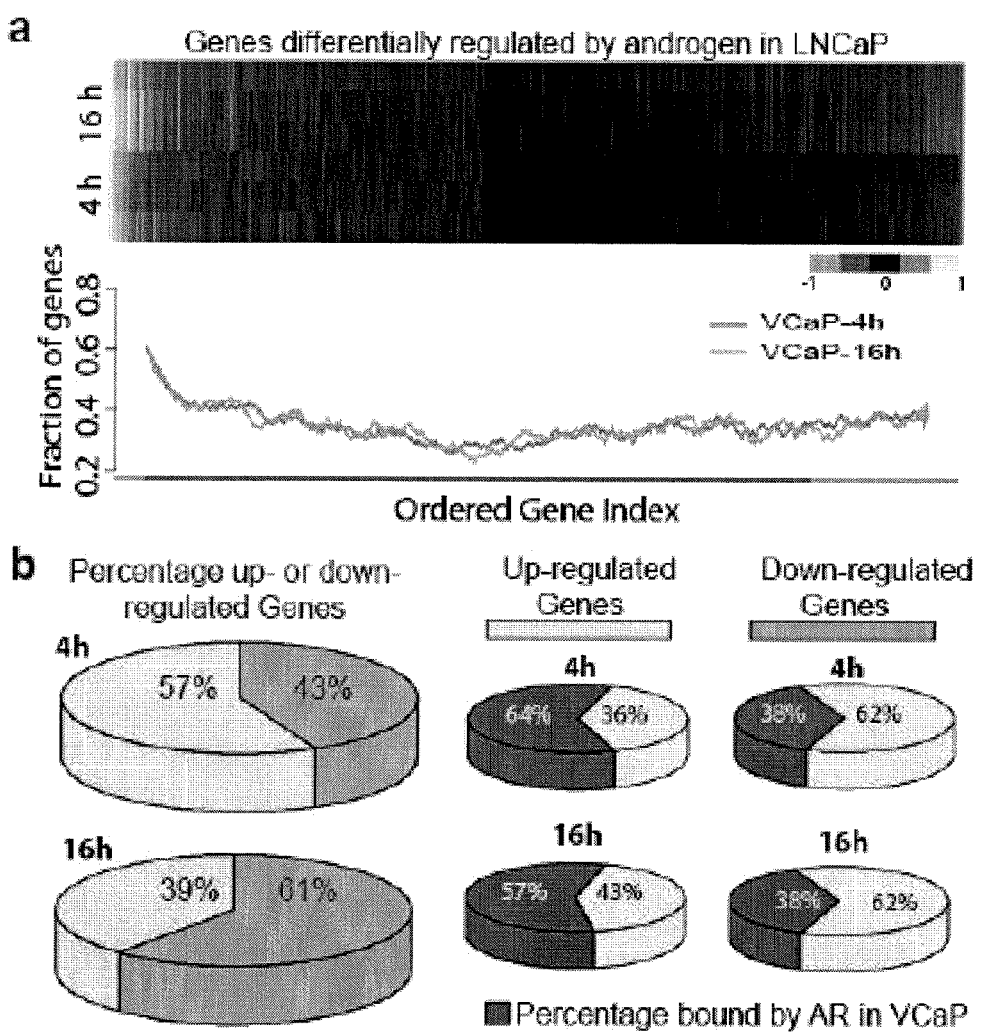
FIG. 12 shows a correlation between differential expression and AR binding in VCaP. (A), Top panel: up- or down-regulated genes by androgen ranked by t-statistics at 4 and 16 h relative to 0 h in LNCaP prostate cancer cell line. Bottom panel: the (4 h) and (16 h) curves represent the 500 gene moving averages of the fraction of genes that contain AR binding sites within 50 kb upstream of the transcription start site or intragenic region in VCaP cells. (B), Percentage of genes that are up-regulated or down-regulated by androgen at 4 h or 16 h of androgen treatment, relative to 0 h, in LNCaP that contain at least one AR binding sites in VCaP as identified by ChIPseq (shown at the right panels).
Figure 13:
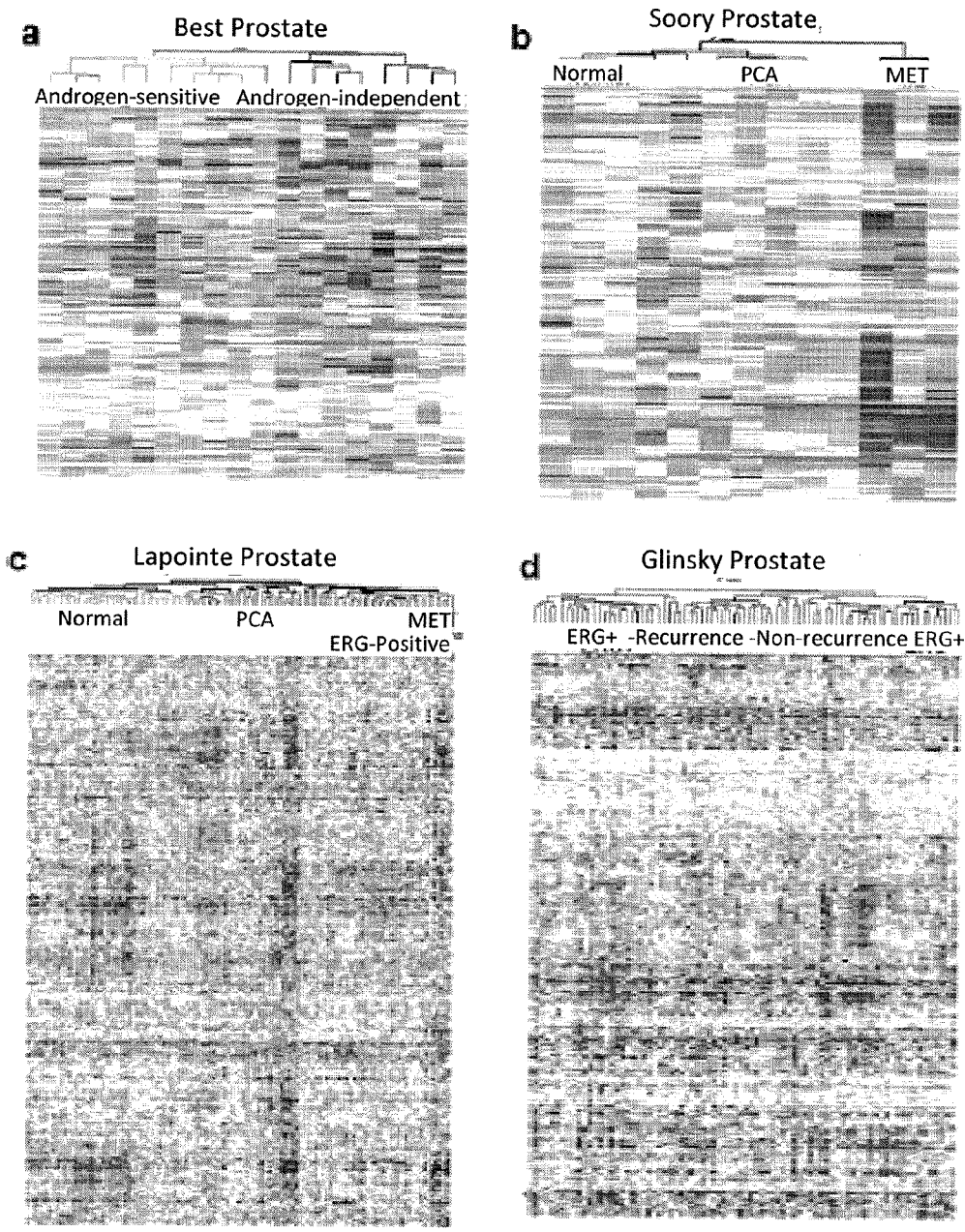
FIG. 13 shows the association of AR-bound genes with in vivo gene expression. AR-bond genes are associated with androgen responsiveness (A), prostate cancer grade (B-C) and ERG status (C-D).

Next, to correlate AR binding with expression regulation by androgen on a genome scale, over-representation of AR binding on androgen-regulated genes defined by an expression microarray study of LNCaP prostate cancer cells (Wang et al., 2007, supra) was examined. The results demonstrated substantially more AR binding in the genomic regions of androgen-responsive genes (FIG. 2F). There were no major differences of this enrichment between the early (4 h) and late (16 h) time-points of androgen treatment. A higher percentage of androgen-induced genes containing AR bound regions than androgen-repressed genes was observed (FIG. 2G), confirming a primary role of AR as a transcriptional activator. The percentage of androgen-induced genes that are bound by AR dropped from 85% at 4 h of androgen treatment to 77% at 16 h, whereas that of the androgen-repressed genes remained essentially the same, around 60%, at both the early and late time-points. A similar correlation of AR occupancy with androgen-responsiveness was observed in VCaP cells (FIG. 12).

Figure 3:
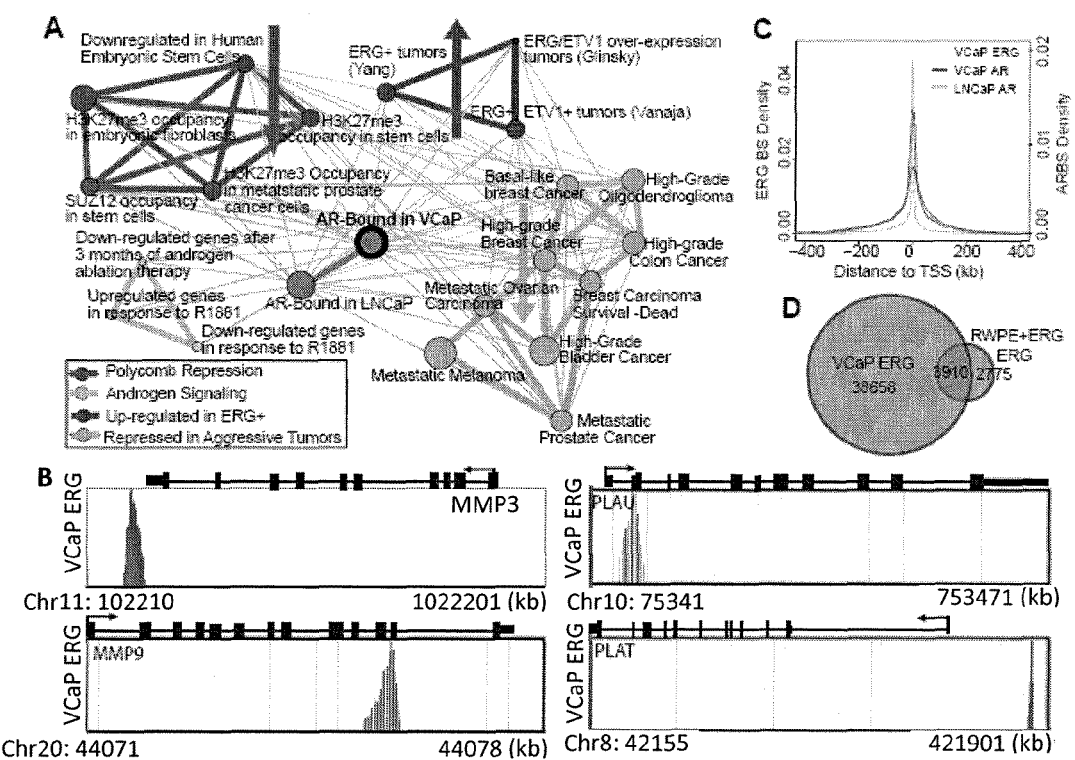
FIG. 3 shows the genomic landscape of ERG binding in prostate cancer cells. (A) Network view of the molecular concepts enriched for VCaP AR-bound genes. Each node represents a molecular concept or a gene set, with node size proportional to the number of genes within each concept. (B) Example of ERG binding on previously reported ERG targets in VCaP cells. (C) Distribution of AR or ERG binding sites relative to closest TSS. (D) Venn diagram showing overlap of endogenous ERG bound sites identified in VCaP cells with ectopic ERG bound sites found in RWPE+ERG cells with stable ERG overexpression.
Figure 6:
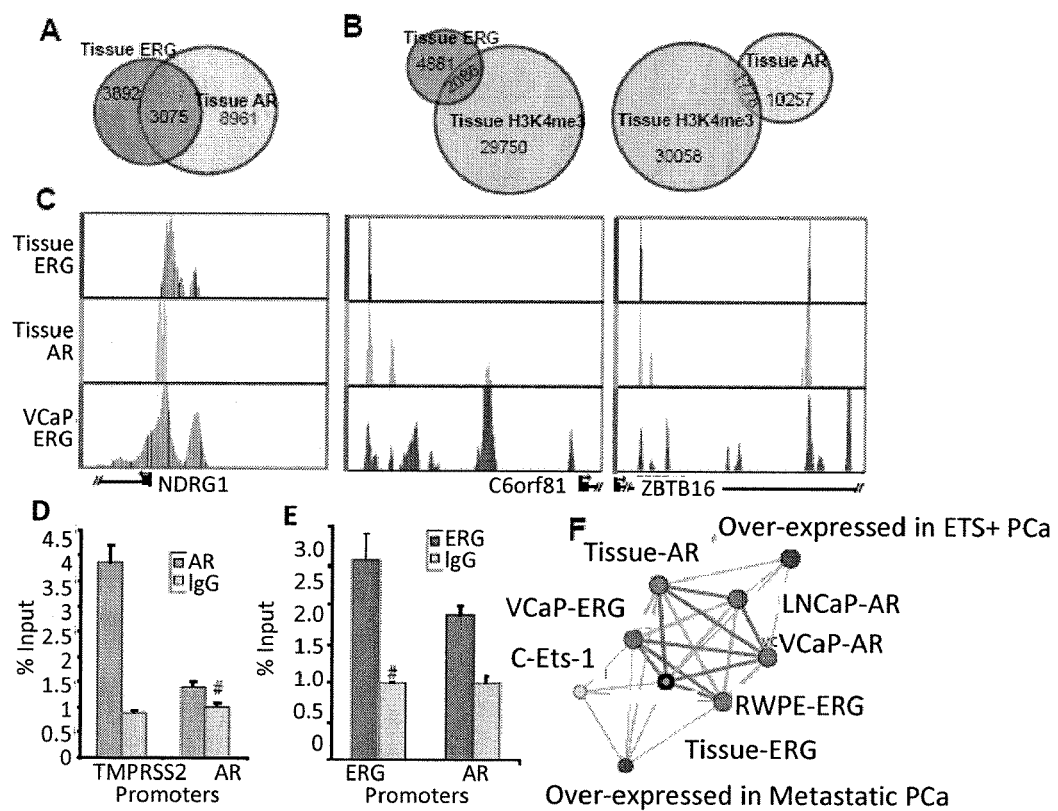
FIG. 6 shows confirmation of genome-wide ERG and AR co-localization in human prostate cancer tissue. (A) ERG and AR ChIP-Seq analysis of a representative human prostate cancer tissue. (B) Venn diagram showing overlap of AR or ERG bound genomic regions with those enriched for H3K4me3, a histone mark associated with active chromatin and gene expression. (C) Representative examples of genes co-occupied by AR and ERG in prostate cancer tissue. Plots are denoted as in FIG. 1B, except that the Y-axes indicate AR and ERG binding in tissues and the schematic gene structures shown to scale relative to chromosomal positions are below the ChIP-Seq plots. (D) ChIP-PCR confirmation of AR occupancy on the enhancers of TMPRSS2 and AR. (E) ChIP-PCR confirmation of ERG occupancy on the regulatory regions of AR and wild-type ERG. (F) Network view of molecular concepts enriched for ERG bound genes in metastatic prostate cancer tissue (Tissue-ERG).

To obtain functional annotation of AR bound genes, the top 3000 AR-occupied genes were analyzed for enrichment in over 15,000 molecular concepts or biological correlates in the Oncomine Molecular Concepts Map (MCM) (Rhodes et al., Neoplasia (New York, N.Y. 9, 443-454 2007). The results demonstrated an enrichment network that significantly (P<1.0×10$^{-100}$) linked AR-bound genes in VCaP to those in LNCaP cells, as well as to multiple androgen-regulated gene sets both in vitro or in vivo (P<1.0×10−10) (FIG. 3A, Table 5). The most enriched (P<1.0×10−20) molecular concepts are gene sets silenced by Polycomb group proteins in embryonic stem cells or metastatic prostate cancers, confirming an association of androgen signaling with processes of normal cellular differentiation. Consistent with the observation of decreased androgen signaling in androgen-independent metastatic prostate cancer (Tomlins et al., Nature genetics 39, 41-51 2007), highly significant enrichments (P<4.0×10−15) of AR binding were observed with gene expression concepts corresponding to "genes under-expressed in metastatic or high-grade tumors". MCM analysis revealed a novel link (P<4.0×10−13) of AR-bound genes to ERG overexpression signatures in prostate cancer, indicating a potential association between AR and ERG regulatory pathways. In summary, ARbound genes were significantly (P<2.0×10−10) associated with prostate tumor sub-types of androgen sensitivity, disease status, ERG expression, and patient survival (Table 5). Heatmaps of hierarchical clustering of gene expression datasets using AR bound genes are shown in FIG. 6.

Figure 14:
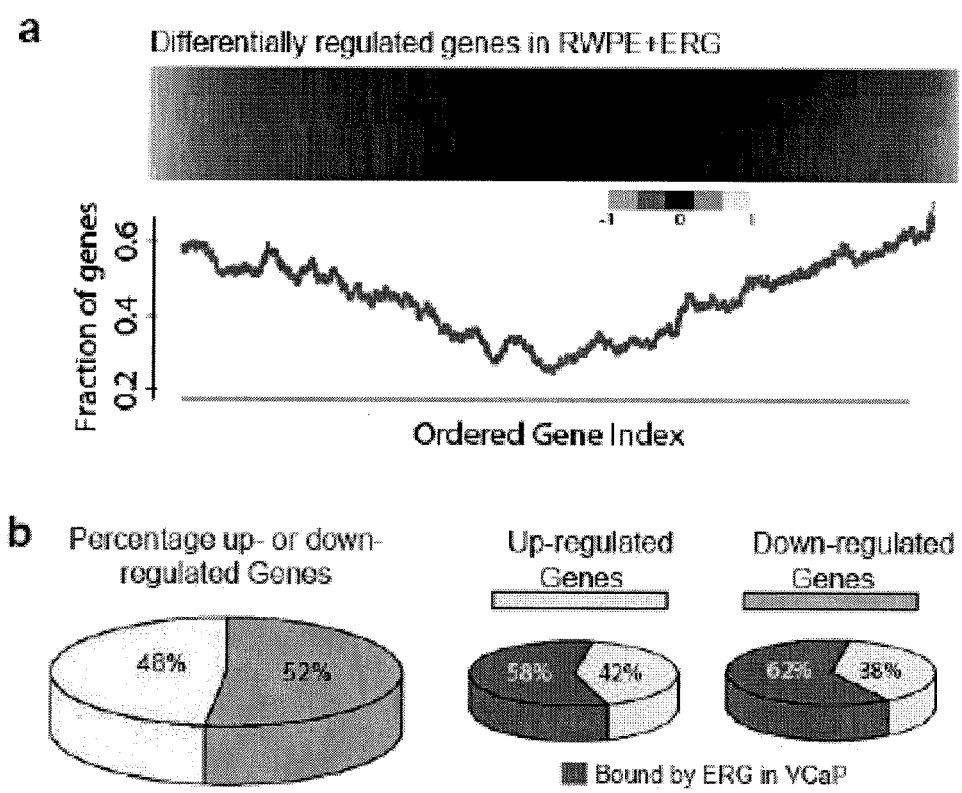
FIG. 14 shows correlation between ERG-induced differential expression and ERG binding. (A), Top panel: up- or down-regulated genes by ERG overexpression ranked by t-statistics in RWPE benign prostate epithelial cell line. Bottom panel: the red line represents the 500 gene moving averages of the fraction of genes that contain ERG binding sites within 50 kb upstream of the transcription start site or intragenic region in VCaP cells. (B), Percentage of genes that is up-regulated or down-regulated by ERG overexpression in RWPE that contain at least one ERG binding sites in VCaP as identified by ChIPseq.

Genome-wide ERG Occupancy in Prostate Cancer Cells. To investigate the potential link between AR- and ERG-mediated transcriptional pathways, ChIP-Seq of ERG was performed in VCaP cells that contain TMPRSS2-ERG gene fusions. As a negative control experiment, ERG ChIP-Seq was also carried out in LNCaP cells that are negative for ERG fusions, thus expressing very low levels of ERG. 42,568 ERG bound peaks were identified in VCaP cells, whereas in LNCaP cells there were only 608 ERG bound regions, representing a background level (Table 1). Moreover, ChIP-Seq successfully detected ERG binding on previously reported target genes, including MMP3, MMP9, PLAT and PLAU (Tomlins et al., Neoplasia (New York, N.Y. 10, 177-188 2008) (FIG. 3B). To correlate ERG binding with gene expression on a larger scale, over-representation of ERG binding on genes differentially regulated by ectopic ERG overexpression (Tomlins et al., 2008, supra) was examined. The results demonstrated an enrichment of ERG binding at the genomic regions of ERG regulated genes (FIG. 14).

Next, the genomic distance of ERG binding sites to the TSS of the nearest genes from RefSeq was determined. While only 5% of AR binding sites in LNCaP and 14% of AR binding sites in VCaP map to promoter regions, approximately 34% of ERG binding sites locate within the proximity of the TSS of target genes (Table 2). This is consistent with the understanding of primarily enhancer-mediated AR regulation (Wang et al., 2007, supra) but promoter-mediated ERG regulation (Tomlins et al., 2008, supra). Furthermore, the distribution of AR binding sites in VCaP demonstrated an overall shift from the enhancer-dominant AR binding pattern in LNCaP towards a more promoter dominant distribution of ERG binding in VCaP cells (FIG. 3C), showing a potential role of ERG in recruiting AR to these promoters in the latter.

To further examine ERG binding activity, ERG ChIP-Seq was performed in the RWPE benign prostate epithelial cells with stable overexpression of ectopic ERG gene fusion product RWPE+ERG) or a GUS (β-glucoronidase) control (RWPE+GUS). 10,765 ERG binding peaks were observed in RWPE+ERG cells, approximately 10 fold more than what is detected in the RWPE+GUS control cells. To remove non-specific binding, ERG binding peaks in the RWPE+ERG cells were compared with those in RWPE+GUS control at each 25 bp sliding window, leading to a total of 6,685 ERG bound regions specific to the RWPE+ERG cells. 58% of these genomic regions also recruited endogenous ERG in VCaP cells (FIG. 3D). There are approximately 30,000 more binding peaks of endogenous ERG in VCaP than that of ectopic ERG in RWPE+ERG cells, indicating the use of additional cofactors for complete recruitment of ERG to its target genes in an endogenous setting. Motif analysis of ERG bound regions in both VCaP and RWPE+ERG cells revealed ETS family binding sites as the most significantly enriched motifs (Table 4), while AREs were found to be the most enriched motif in AR binding peaks and the NRSF binding motif the optimal for NRSF binding sites (Johnson et al., Science (New York, N.Y. 316, 1497-1502 2007), thus supporting the specificity of ChIP-Seq data.

Figure 15:
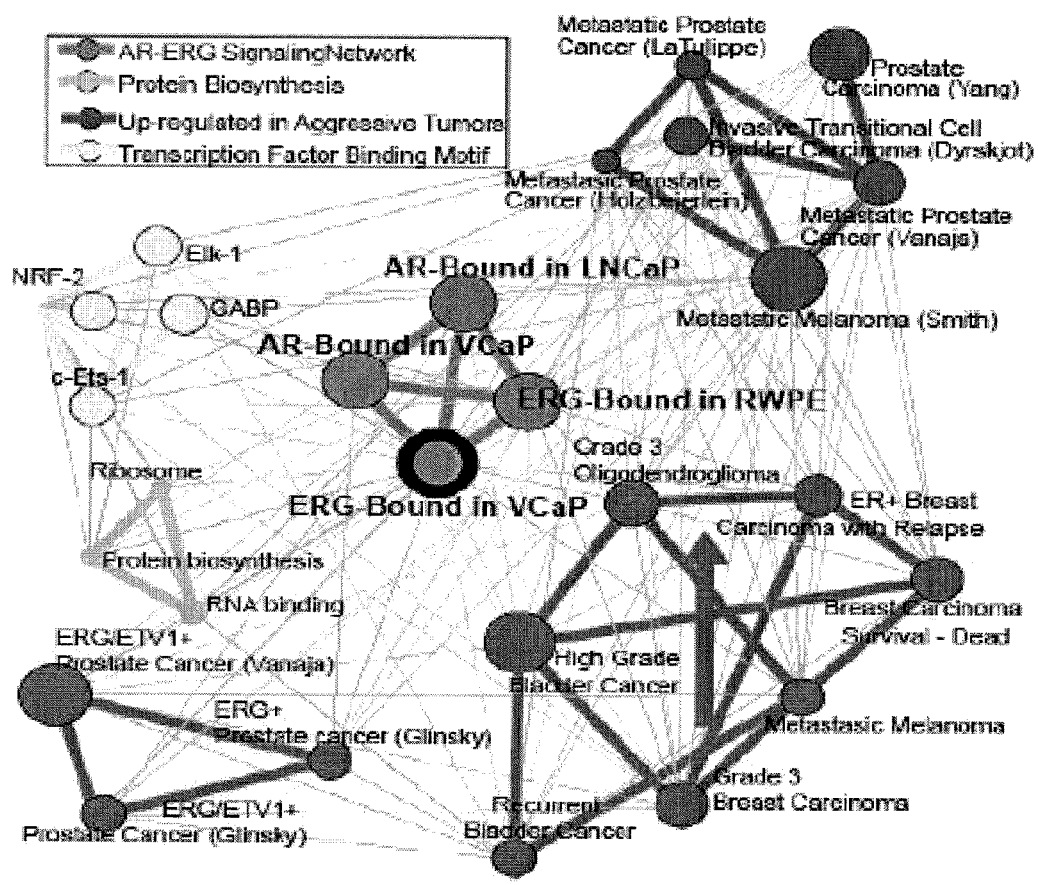
FIG. 15 shows a network view of the molecular concepts enriched for VCaP ERG-bound genes. ChIP-Seq ERG-bound genes in VCaP cells were ranked based on peak height and the top 3000 genes were analyzed for disproportional enrichment in molecular signatures or gene sets denoted in MCM.

To gain insights into ERG-mediated pathways, enrichment MCM analysis of ERG-occupied genes in VCaP cells (FIG. 15 and Table 6) was performed. The most significant (P<1.0×10−100) enrichment network interconnected the molecular concepts of "ERG-bound in VCaP" (the index list queried), "ERG-bound in RWPE+ERG", and "ETS binding motifs". Further, ERG-occupied genes significantly overlap with genes that distinguish ETS positive prostate cancers from ETS negative tumors. ERG-occupied genes also overlap with genes overexpressed in metastatic prostate cancer or more aggressive forms of other solid tumors such as bladder cancer, breast cancer, oligodendroglioma, and melanoma. This is consistent with the growing notion that TMPRSS2-ERG positive prostate cancers have a more aggressive course (Clark et al., Oncogene 27, 1993-2003 2008; Demichelis et al., Oncogene 26, 4596-4599 2007; Furusato et al., Mod Pathol 21, 67-75 2008; Nam et al., British journal of cancer 97, 1690-1695 2007; Rajput et al., Journal of clinical pathology 60, 1238-1243 2007; Wang et al., Cancer research 66, 8347-8351 2006). Within the strongest (P<1.0×10−100) enrichment network for ERG bound genes are concepts of "AR-bound in LNCaP", and "AR-bound in VCaP", providing the first evidence for a link between these two transcription factors in prostate cancer.

Figure 4:
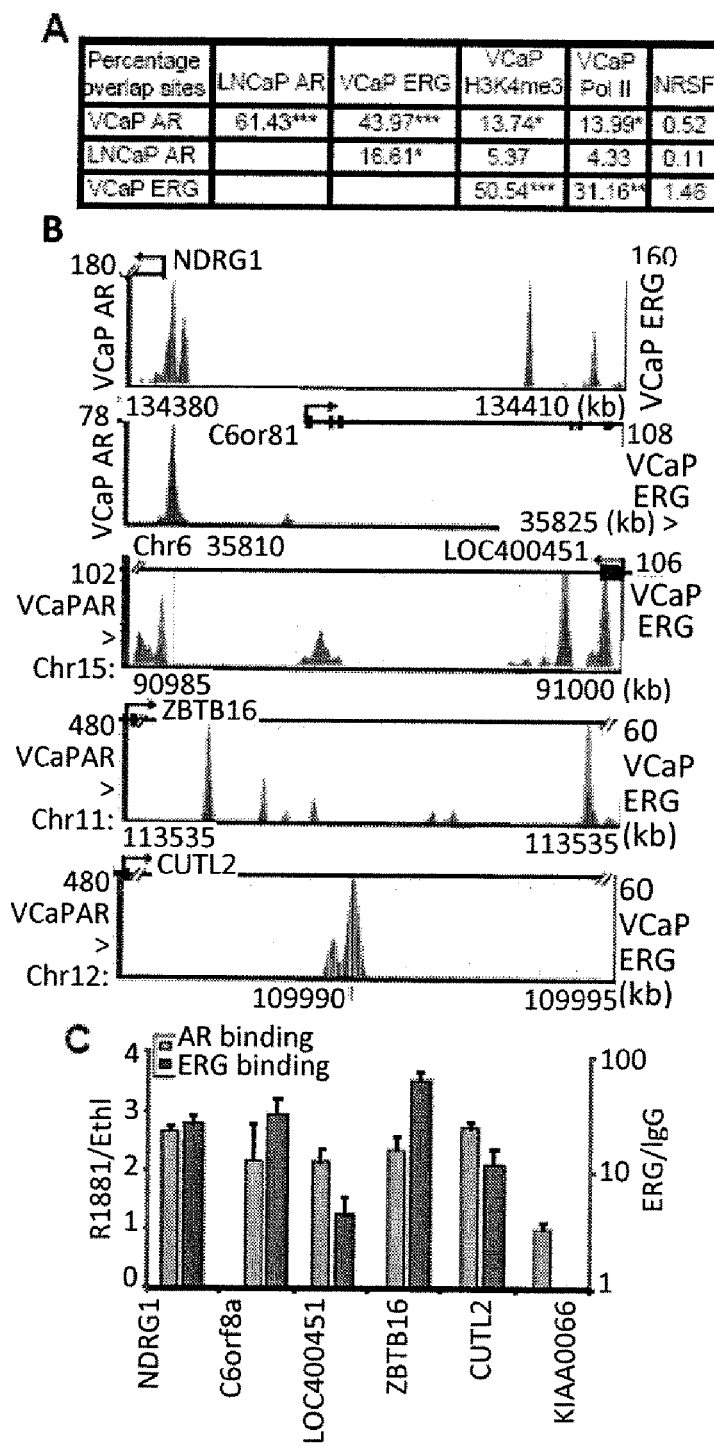
FIG. 4 shows molecular cross-talk between ERG- and AR-mediated pathways. (A) Overlap of LNCaP AR, VCaP AR, VCaP ERG, VCaP H3K4me3, and VCaP PolII bound regions. $*P<0.05$, $P<0.01$, and $*P<0.001$ by hypergeometric tests. (B) Representative examples of genes co-occupied by AR and ERG in VCaP cells. Plots are denoted as in FIG. 1B, except that the Y axes represent the number of ChIP-Seq reads of AR (left) and ERG binding (right), respectively. (C) ChIP-PCR confirmation of AR and ERG co-occupancy on the list of genes shown in 4B. Y-axis on the left represents AR ChIP enrichment of target genes in R1881 (R) treated, relative to ethanol (E) treated VCaP cells that have been hormone deprived for 3 days.

AR and ERG Co-occupy Many Target Genes. To examine potential AR and ERG co-occupancy of target genes, the genomic regions bound by each transcription factor were compared for overlap at every 25 bp sliding window. While 61% of AR bound regions from LNCaP and VCaP overlap, approximately 44% of AR bound regions overlap with those bound by ERG in VCaP cells (FIG. 4A). However, only 16.6% of AR bound regions in LNCaP overlap with ERG bound sites in VCaP, indicating the differences between cell lines. The observed overlap between AR and ERG bound regions is substantial as AR and ERG bound regions cover less than 0.1% and 0.7% of the entire human genome, and thus the chance of this low percentage to overlap is exceedingly small. This chance is further reduced by the fact that AR primarily binds to enhancer elements while ERG binds to promoters of target genes. To statistically confirm that the overlap between AR and ERG is not a random event, the ChIP-Seq derived binding sites of NRSF (Johnson et al., Science (New York, N.Y. 316, 1497-1502 2007), a neural specific transcription factor that has not been shown to associate with either AR or ERG, was used as a control. There is less than 2% overlap of the bound regions of either AR or ERG with NRSF. The overlap between AR and ERG binding sites is thus significantly (P<0.0001 by Chi-Square test) more than their overlap with NRSF bound regions.

To preclude the possibility that AR and ERG co-occupy target regions merely because they both bind to actively transcribed genes, ChIP-Seq analysis of H3K4me3 and RNA PolII, which binds primarily to the proximity of TSS of actively transcribed genes (Barski et al., Cell 129, 823-837 2007) was performed. 4.3%, 14% and 31% of LNCaP AR, VCaP AR and VCaP ERG bound regions, respectively, overlapping with RNA PolII binding sites was observed (FIG. 4A). The overlap of AR with PolII is substantially lower than the overlap between ERG and PolII. The present invention is not limited to a particular mechanism. Indeed, an understanding of the mechanism is not necessary to practice the present invention. Nonetheless, the results showed that although there is only 14% of AR bound regions overlapping with RNA PolII, there are substantially more (44%) AR bound regions that overlap with ERG binding sites, thus suggesting their co-occupancy due to mechanisms other than binding to expressed genes. Therefore, although the amount of overlap with PolII indeed reflects the binding of a specific transcription factor to active TSS, the overlap between AR and ERG is much higher than their overlap with PolII, thus precluding the mechanism of their overlap being solely related to expressed genes with PolII binding. This is further confirmed by a similar overlapping pattern of AR and ERG with H3K4me3 mark of active genes (FIG. 4A). Moreover, the much higher percentage (14%) of VCaP AR than LNCaP AR (4.3%) binding sites overlapping with either PolII or H3K4me3 indicates enhanced promoter-mediated AR regulation in VCaP cells (FIG. 3C).

To confirm co-occupancy of AR and ERG on target genes, a set of 5 genes bound by both AR and ERG was randomly selected, including NDRG1, C6orf81, LOC400451, ZBTB16, and CUTL2 that are located on different chromosomes. The results demonstrated a clear overlap of AR and ERG bound regions at the proximity of these target genes (FIG. 4B). Using primers specific to each of these genes AR and ERG binding was confirmed by conventional ChIP-PCR assay (FIG. 4C). The enrichment of AR binding was assessed in VCaP cells treated with synthetic androgen relative to vehicle treated cells. Enrichment of ERG binding was evaluated relative to the IgG control used for ChIP.

Figure 5:
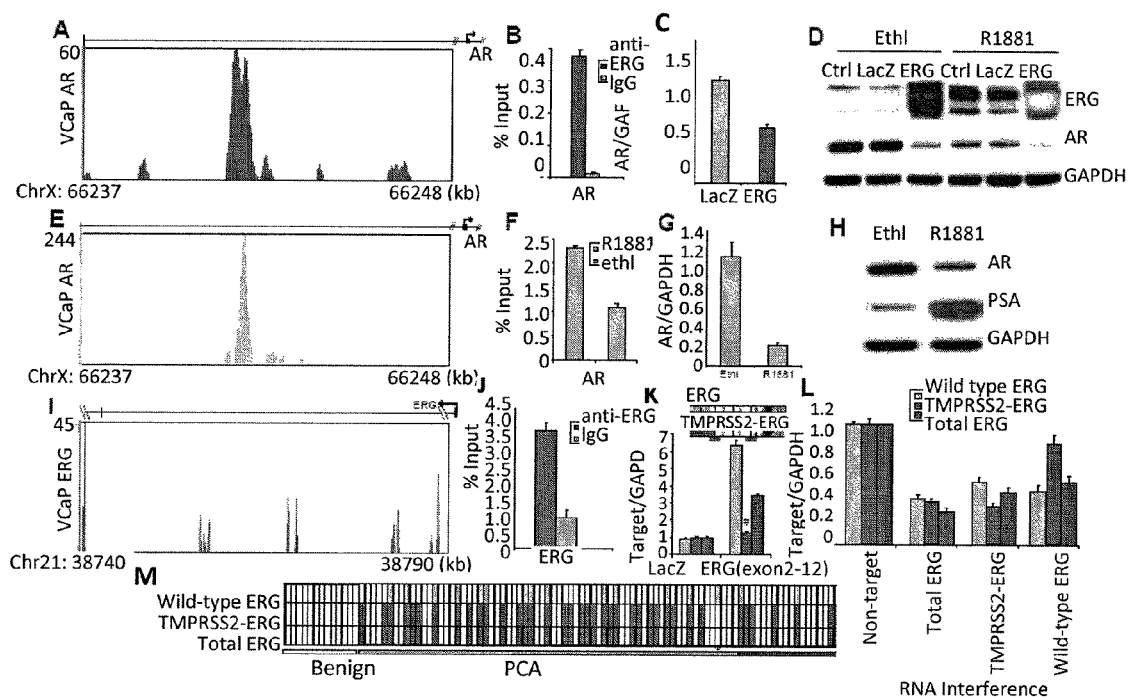
FIG. 5 shows feedback loops connecting TMPRSS2-ERG, wild-type ERG and AR. (A) ERG binds to the regulatory region of AR by ChIP-Seq analysis. Plots for A, E, and I are denoted as in FIG. 1B, except that on the Y-scales is the number of ChIP-Seq reads of AR or ERG binding in VCaP cells as indicated. (B) Conventional ChIP-PCR confirmation of ERG binding to the regulatory region of AR. (C) Ectopic ERG overexpression in VCaP cells represses AR mRNA. (D) Ectopic ERG overexpression in VCaP cells inhibits AR protein levels. (E) AR binds to the regulatory region of AR by ChIP-Seq analysis. (F) Conventional ChIP-PCR confirmation of AR binding to the regulatory region of AR. (G) Synthetic androgen R1881 inhibits AR mRNA expression in VCaP cells. (H) R1881 inhibits AR protein expression in VCaP cells. (I) ERG binds to the regulatory region of wild-type ERG by ChIP-Seq analysis. (J) Conventional ChIP-PCR confirmation of ERG binding to the regulatory region of wild-type ERG. Error bars: $n=3$, mean±SEM, $P<0.01$. (K) Ectopic expression of the truncated ERG (exons 2-12) which is the prevalent fusion product in prostate cancer induces wild-type ERG but not TMPRSS2-ERG and total ERG. (L) Specific RNA interference of TMPRSS2-ERG leads to repression of wild-type ERG. (M) Wild-type ERG is induced in a subset of human prostate cancers expressing ETS gene fusions.
Figure 16:
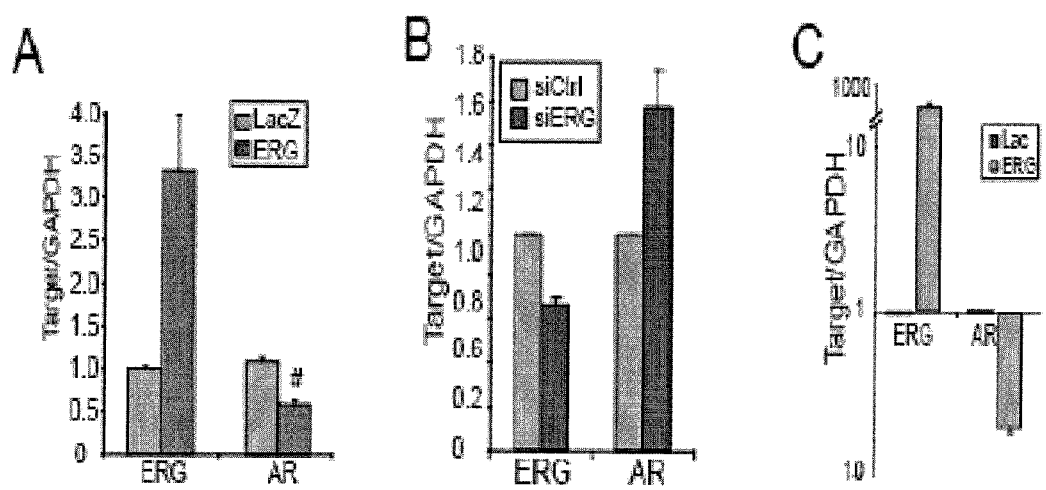
FIG. 16 shows that ERG expression negatively regulates the level of AR expression. (A) VCaP cells were infected with adenovirus ERG or lacZ control. QRTPCR was performed to assay the level of ERG and AR in lacZ or ERG infected cells. (B) VCaP cells were transfected with siRNA duplex against ERG (siERG) or a control siRNA. QRT-PCR was performed to assay the level of ERG and AR. (C) RWPE benign prostate epithelial cells were infected with adenovirus ERG or lacZ control. QRT-PCR.
Figure 17:
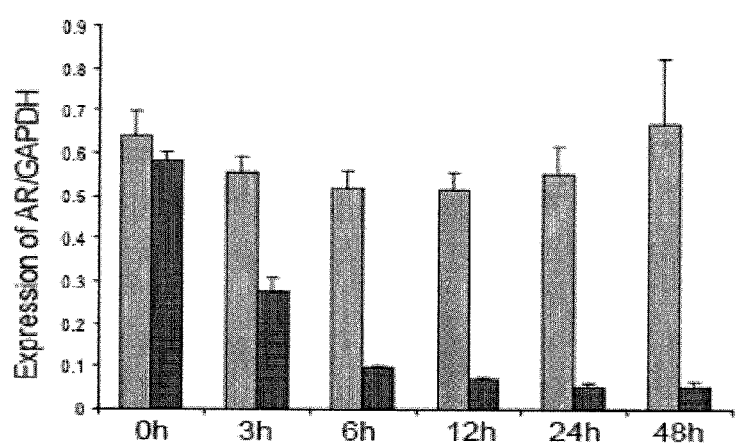
FIG. 17 shows repression of AR transcript following time-course treatment of synthetic androgen R1881.
Figure 18:
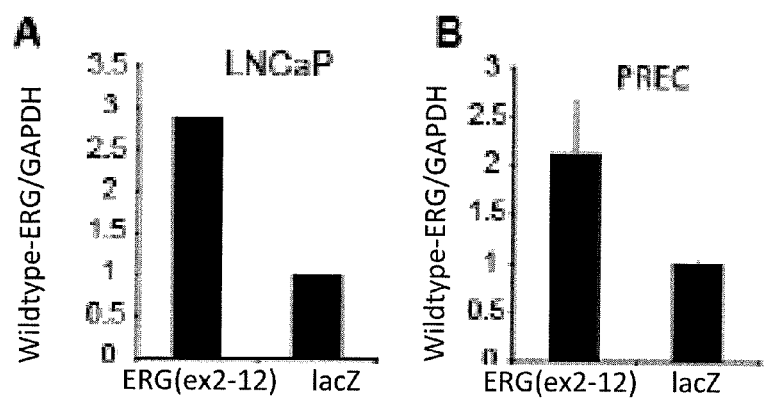
FIG. 18 shows that overexpression of the primary fusion ERG product upregulates wild-type ERG expression in LNCaP and PREC cells.
Figure 19:
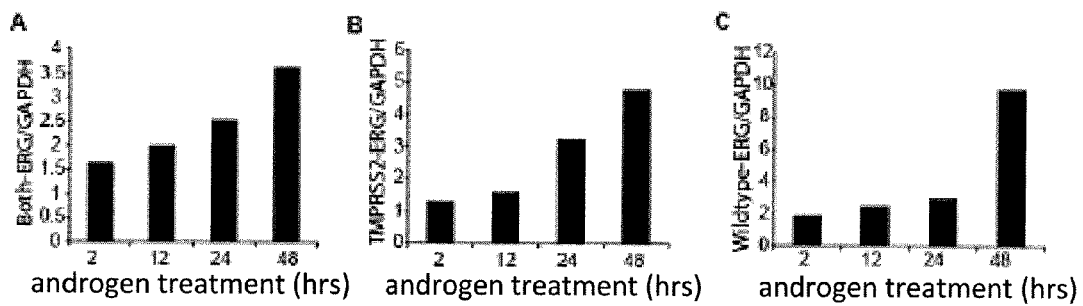
FIG. 19 shows expression analysis of ERG variants following timecourse of androgen treatment.
Figure 20:
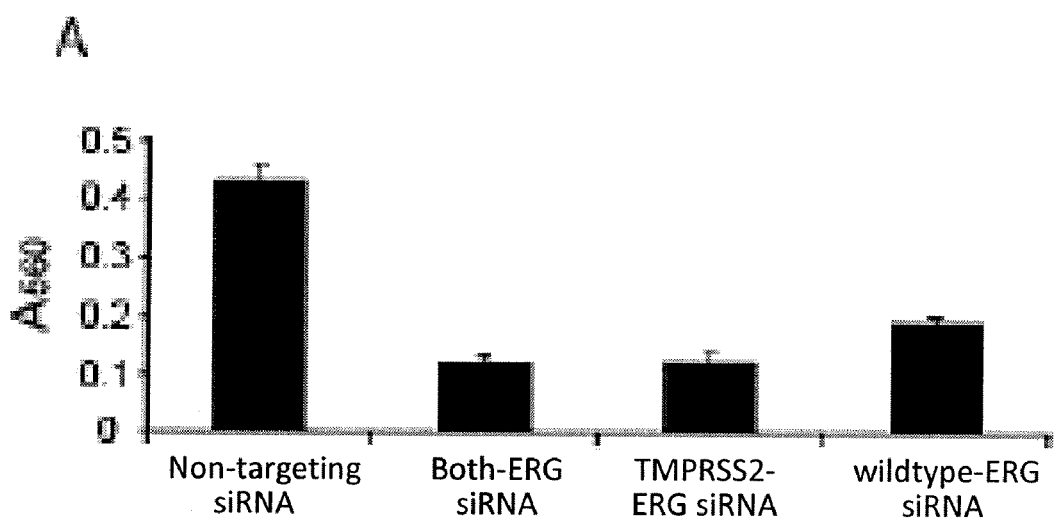
FIG. 20 shows reduced invasion upon RNA interference of various ERG variants. RNA interference specific to each ERG variants was done in VCaP cells. (A) Invasion assay was performed using the Modified Boyden Chamber Assay. (B) Photomicrographs of invaded cells are shown.
Figure 20:
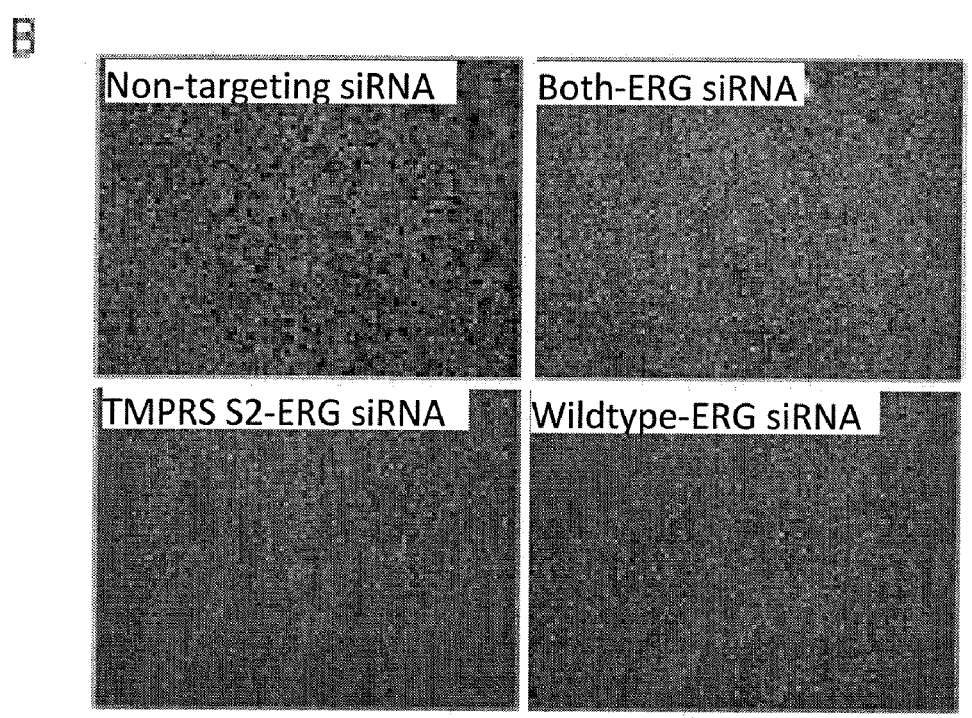

Feedback Loops Connecting TMPRSS2-ERG, Wild-type ERG and AR. One of the genes that were strongly bound by ERG in VCaP cells was AR (FIG. 5A). The regulation of AR by ERG may thus suggest a feedback loop in between. By conventional ChIP-PCR assay ERG binding on the AR locus in VCaP cells was confirmed (FIG. 5B). In addition, by both ectopic ERG overexpression and RNA interference assays it was demonstrated that the transcript level of AR is negatively regulated by ERG (FIG. 5C, FIG. 16). Moreover, immunoblot analysis of VCaP cells demonstrated clear repression of AR protein upon ERG overexpression (FIG. 5D). An examination of AR and ERG co-occupancy at the AR gene revealed AR binding to its own genomic regulatory region (FIG. 5E). Conventional ChIP-PCR assay demonstrated strong AR enrichment at itself in androgen-treated VCaP cells relative to vehicle-treated cells (FIG. 5F). Moreover, compared with vehicle treated cells, hormone-deprived VCaP cells treated with synthetic androgen expressed significantly less amount of AR (FIG. 5G), and this repression reached to over 10 folds at 24 h after treatment (FIG. 17). Immunoblot analysis further confirmed this negative feedback loop of AR at the protein level (FIG. 5H). As cross-regulation of AR and ERG, and self-regulation of AR, was observed, it was investigated whether ERG may regulate itself. ChIP-Seq analysis demonstrated multiple ERG binding peaks at the genomic loci of the ERG gene (FIG. 5I). By conventional ChIP-PCR using primers flanking the highest binding peak within the ERG genomic region, strong ERG binding in VCaP cells (FIG. 5J) was confirmed. To investigate the auto-regulation of ERG expression, a truncated version of ERG starting from exon 2 to the reported stop codon was overexpressed in VCaP cells and the corresponding expression changes were assayed using primers specific to TMPRSS2-ERG, wild-type ERG and both (FIG. 5K). The results showed that truncated ERG, which is the prevalent fusion product in prostate cancer, induces the expression of wild-type ERG but not TMPRSS2-ERG, which is under the regulation of the TMPRSS2 enhancer. This finding was confirmed in benign prostate epithelial cells (PREC) and LNCaP prostate cancer cells by overexpressing fusion ERG and assaying for wild-type ERG (FIG. 18). Concordantly, a delayed upregulation of the wild-type ERG, relative to TMPRSS2-ERG, was observed following androgen treatment, showing the secondary effect of androgen on wild-type ERG through its primary effect on TMPRSS2-ERG (FIG. 19). Furthermore, specific RNA interference of TMPRSS2-ERG led to the repression of wild-type ERG, while specific RNA interference of wild-type ERG did not affect TMPRSS2-ERG expression (FIG. 5L). RNA interference of ERG variants also strongly reduced the invasive potential of VCaP prostate cancer cells (FIG. 20). Moreover, qRT-PCR analysis of the three ERG variants in a panel of benign prostate tissue, localized and metastatic prostate cancer indicated induction of wild-type ERG in a subset of human prostate cancers expressing ETS gene fusions (FIG. 5M). Thus a subset of prostate cancers that harbor the TMPRSS2-ERG fusion may also induce expression of wild-type ERG defining a distinct molecular sub-type. Taken together, cross- and auto-regulation of TMPRSS2-ERG, wild-type ERG and AR form an interconnected transcriptional "switch" involved in the homeostasis of the AR-ERG regulatory network and the progression of prostate cancer.

Figure 21:
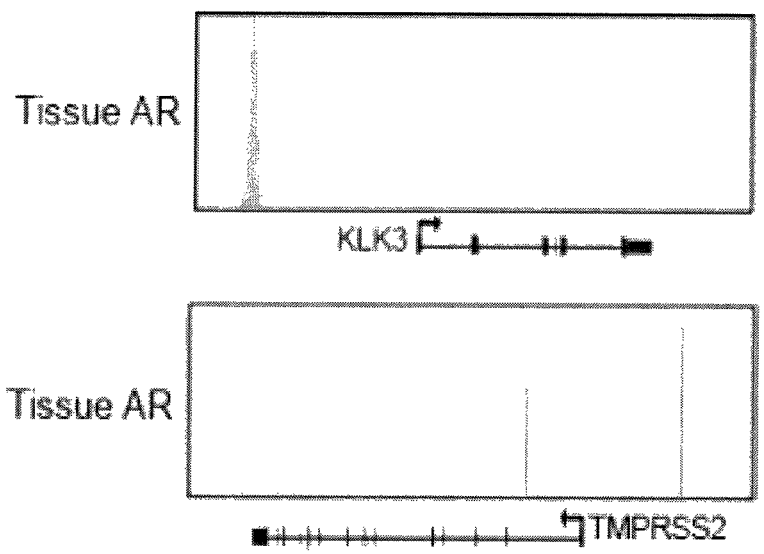
FIG. 21 shows that ChIP-Seq analysis of a metastatic prostate cancer tissue revealed AR binding at the previously reported enhancers of the KLK3 and TMPRSS2 genes.

The Regulatory Circuitry of ERG and AR in Prostate Cancer Tissue. Using in vitro cell line models, interconnected regulatory network of AR and ERG were demonstrated. To further investigate its relevance in vivo, AR and ERG co-occupancy were validated by ChIP-Seq analysis of a human prostate tumor that harbors the TMPRSS2-ERG gene fusion and also expresses high levels of AR. Due to a number of technical challenges, the community has had difficulty in developing genome wide maps of transcription factors in human tumors (as opposed to cell lines). A ChIP-Seq protocol that is optimized for DNA derived from frozen human tissue specimens was developed. By ChIP-Seq analysis of an ERG+, AR+human prostate cancer tissue, it was possible to detect 12,036 AR bound and 6,967 ERG bound regions (Table 1). As intimated by the cell line data, AR binding peaks were identified at the previously defined enhancer elements of the PSA and TMPRSS2 genes (FIG. 21).

A comparison of tissue AR and ERG bound regions revealed marked overlap (44%), thus validating genome-wide co-occupancy of AR and ERG in prostate tumors in vivo (FIG. 6A). To further validate the specificity of this overlap ChIP-Seq analysis of H3K4me3, a histone mark for active transcription, was performed in the same tissue. Due to the good quality of the anti-H3K4me3 antibody and the abundance of this active histone mark, 31,836 bound regions were observed. However, despite much wider coverage of H3K4me3 mark over the genome only 5.5% and 6.5% of these regions overlap with tissue AR and ERG binding sites, respectively (FIG. 6B). The overlap between tissue AR and ERG bound regions is significantly (P<0.0001 by Chi-Square test) more than their overlap with H3K4me3. In addition, a closer examination of a set of AR and ERG co-occupied genes, including NDRG1, C6orf81 and ZBTB16, confirmed that tissue AR and ERG binding sites overlap with VCaP ERG binding sites (FIG. 6C).

The feedback loops detected in VCaP cells that connect TMPRSS2-ERG, wild-type ERG and AR were analyzed in tissue. Conventional ChIP-PCR assays were carried out on individual genes in the same metastatic prostate cancer tissue that was used for ChIP-Seq analysis. The enrichment of target genes by anti-AR or anti-ERG antibodies were evaluated relative to the control IgG with no enrichment, and normalized to the 3' intronic region of the KIAA0066 non-target control gene. A strong binding of AR on the TMPRSS2 enhancer was confirmed (FIG. 6D). Significant (P<0.05 by t-test) AR ChIP-enrichment on its own genomic regions was observed. Similarly, ChIP-PCR analysis confirmed ERG binding on the regulatory regions of both ERG and AR genes in prostate tumors (FIG. 6E).

To explore the potential function of ERG bound genes in metastatic prostate cancer, the 1,534 genes that contain ERG binding peaks within the proximity of TSS were selected. This set of genes were compared for disproportional enrichment in all molecular concepts or gene sets in the Oncomine MCM database (Rhodes et al., 2007, supra). This analysis revealed a core transcriptional regulatory circuitry composed of biological correlates with highly significant overlaps ($P<1.0\times10^{-100}$); these include ERG-bound and AR-bound in tumors, ERG-bound and AR-bound in VCaP cells, and ERG-bound in stable RWPE+ERG cells (FIG. 6F). While the overlap of AR and ERG bound sites in the AR+ and ERG+tissue as well as VCaP cells are of the highest significance, their overlap with those in the ERG-negative LNCaP cells are of much less significance ($P<1.0\times10^{-50}$) (Table 7). In addition, a marked overlap was observed between tissue ERG-bound genes and genes that contain ETS motifs, supporting the relevant enrichment of ETS motif in ERG bound regions identified by ChIP-Seq. ERG-bound genes are associated with genes differentially regulated in ETS+prostate cancer as well as metastatic prostate cancer, up to 80% of which harbor TMPRSS2-ERG gene fusions. Therefore, MCM analysis of ERG-bound genes in tissue revealed a core transcriptional regulatory network of AR and ERG that is functionally associated with expression deregulation in prostate cancer.

Figure 7:
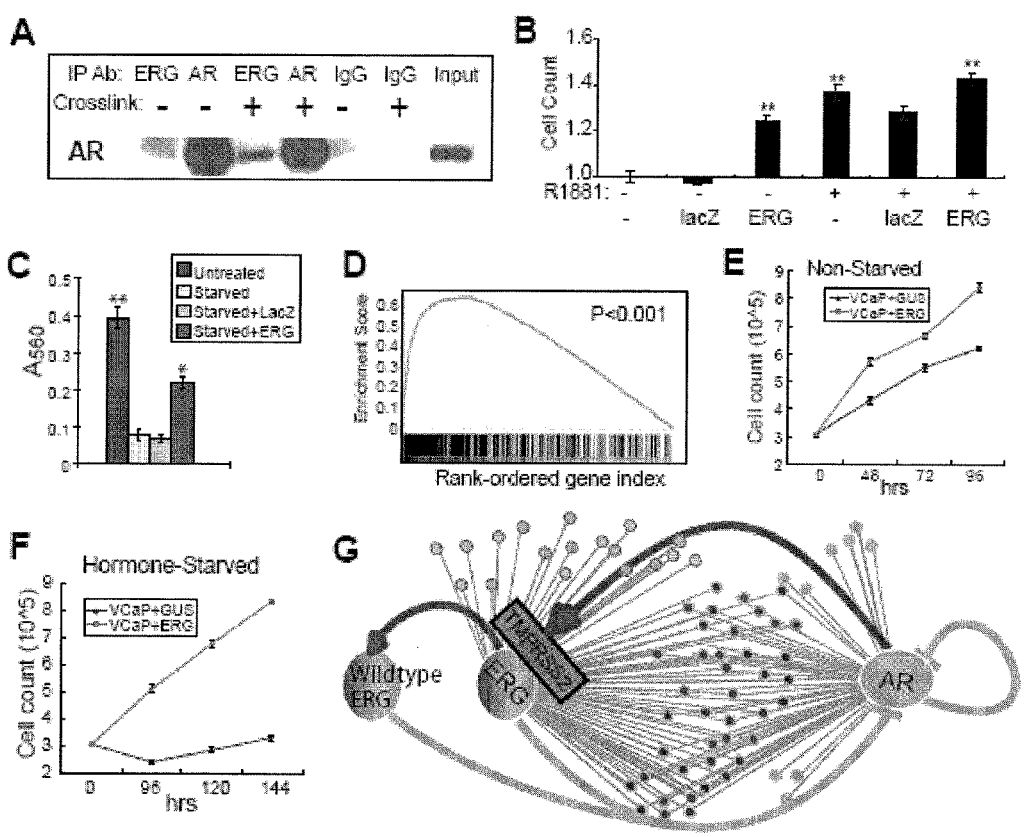
FIG. 7 shows ectopic expression of ERG maintains the neoplastic properties of androgen-sensitive prostate cancer cells in the absence of androgen. (A) Indirect AR and ERG interaction mediated by bound DNA. VCaP (B) Ectopic ERG overexpression induces VCaP cell growth in the absence of androgen. (C) Ectopic ERG overexpression partially rescues androgen-mediated cell invasion in hormone-deprived VCaP cells. (D) Significant overlap ($P<0.001$) between androgen-induced and ERG-mediated gene expression patterns. (E) Ectopic ERG overexpression in prostate cancer cells increases cell growth. (F) Ectopic ERG overexpression confers androgen-independent cell proliferation. (G) Conceptual model of the interconnected transcriptional regulatory circuitry in human prostate tumors.

ERG Overexpression Maintains the Neoplastic Properties of Androgen-sensitive Prostate Cancer Cells in the Absence of Androgen. ChIP-Seq experiments demonstrated co-occupancy of AR and ERG at genomic regions in both in vitro cell lines and in vivo tissue, thus showing that AR and ERG proteins may interact or bind in close proximity at target DNA. To experimentally confirm this interaction, co-immunoprecipitation (co-IP) assays were carried out in VCaP cells. The results showed that AR and ERG proteins do not directly cooperate with each other to form a protein complex (FIG. 7A). However, co-IP analysis following protein-DNA cross-linking detected ERG protein in the AR precipitates but not in the control IgG pulldown, showing an indirect AR and ERG protein interaction mediated by the DNA that they both bind.

Figure 22:
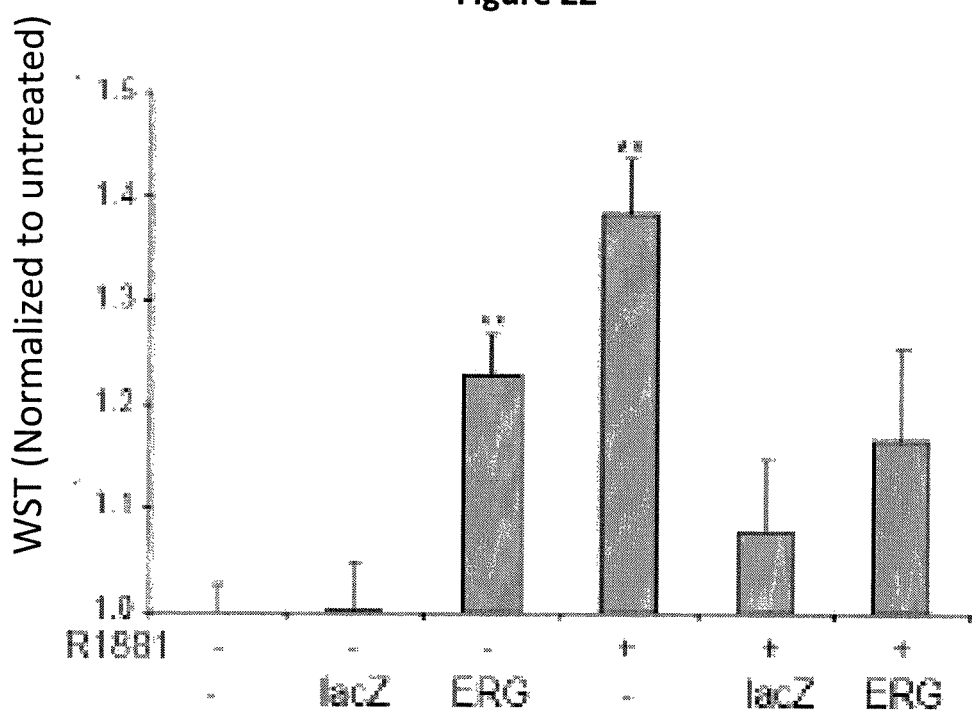
FIG. 22 shows that ERG overexpression induces hormone-deprived prostate cancer cell growth as determined by WST cell proliferation assay.
Figure 23:
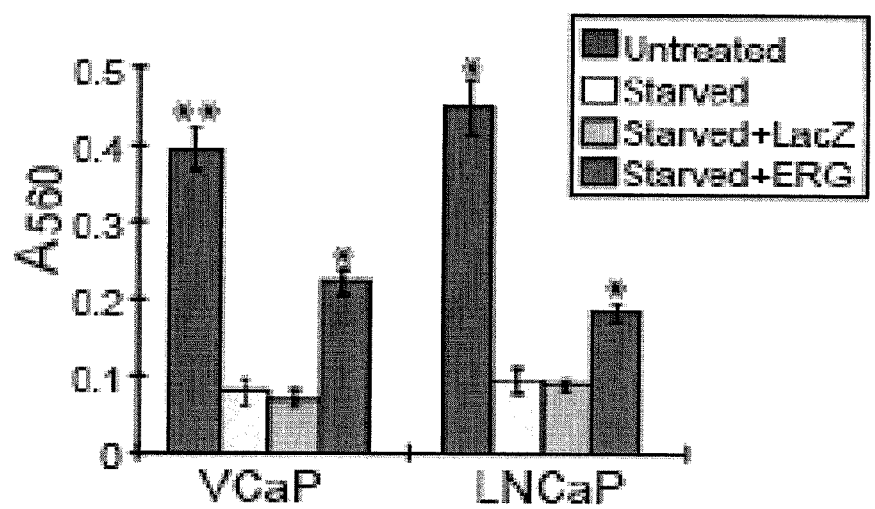
FIG. 23 shows that ERG overexpression rescues cell invasion of hormone deprived LNCaP and VCaP prostate cancer cells.
Figure 24:
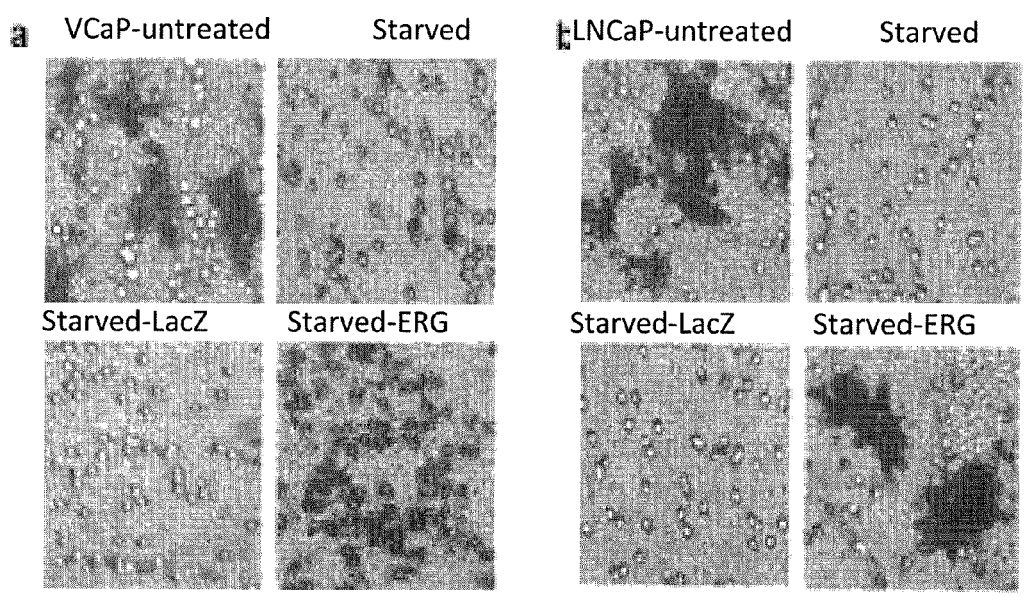
FIG. 24 shows ERG overexpression in hormone-deprived (A), VCaP and (B), LNCaP prostate cancer cells partially rescues androgen-induced cell invasion.
Figure 25:
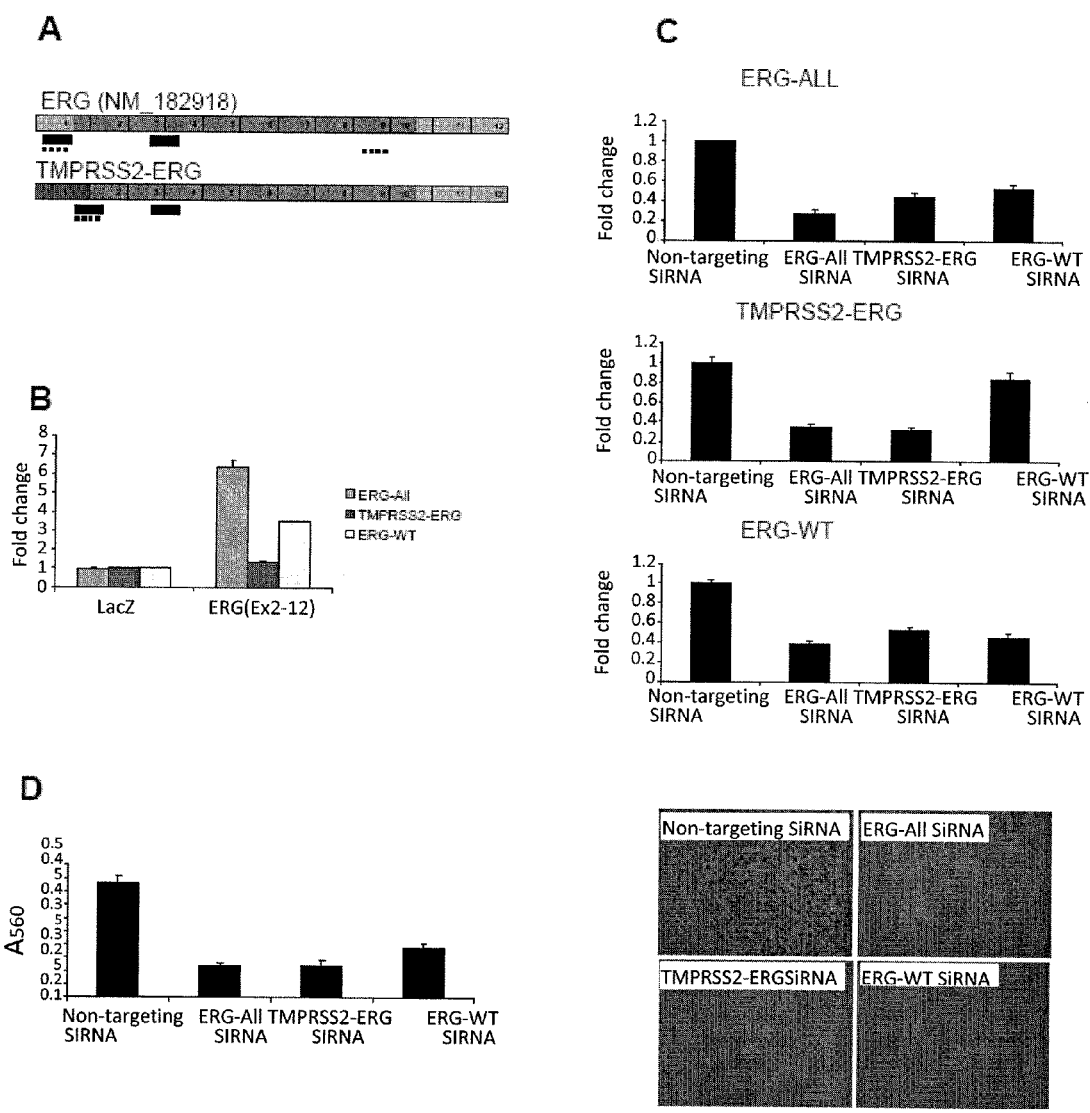
FIG. 25A-D shows siRNA inhibition of ERG and TMPRSS2-ERG.

To investigate the functional consequence of AR and ERG co-occupancy of target genes, the effects of ERG overexpression was compared with that of androgen stimulation. The hypothesis was that, by regulating a shared set of target genes, ERG overexpression may convey some androgen-mediated effects. Androgen treatment of hormone-starved VCaP cells induced cell proliferation as monitored by cell count and the WST cell proliferation assay (FIG. 7B and FIG. 22). Overexpression of the ERG gene fusion product substantially induced VCaP cell growth even at the absence of androgen. Similarly, androgen withdrawal attenuates the invasive capabilities of the androgen-sensitive VCaP and LNCaP cells, as expected, and this inhibition can be partially rescued by ERG overexpression (FIG. 7C and FIGS. 23-24). To evaluate the underlying mechanism of this shared functionality, the gene expression changes induced by androgen and ectopic ERG overexpression were investigated. GSEA (Gene Set Enrichment Analysis) analysis revealed a significant overlap ($p<0.001$) of AR and ERG-mediated gene expression patterns (FIG. 7D), which may confer the common neoplastic properties of AR and ERG.

It was next hypothesized that, through cross-talk with AR-mediated pathways, ERG may be able to drive androgen-sensitive cells to proliferate in an androgen-independent manner. To test this hypothesis, the androgen-sensitive VCaP prostate cancer cells were infected with GUS control lentivirus or ERG lentivirus. Stable clones expressing ERG (VCaP+ERG) or GUS (VCaP+GUS) were selected and assayed for cell proliferation. It was observed that VCaP+ERG cells grow markedly faster than the VCaP+GUS control cells; the difference is especially prominent at the absence of androgen (FIG. 7E-F). The VCaP+ERG cells were able to proliferate continuously in the absence of androgen, while the VCaP+GUS cells failed to grow. Therefore, ERG may play a critical role in regulating androgen-independent prostate cancer progression.

TABLE 1

Summary of sequencing reads obtained by ChIP-seq

| Cell types | Treatment | ChIP Antibodies | Uniquely mapped reads | Enriched Peaks |
|---|---|---|---|---|
| VCaP | | H3K4me3 | 10.95 | 30336 |
| VCaP | | PolII | 6.88 | 15881 |
| VCaP | ethanol treated | AR | 4.12 | 1297 |
| VCaP | R1881 treated | AR | 15.44 | 21376 |
| VCaP | | ERG | 9.42 | 42568 |
| LNCaP | ethanol treated | AR | 2.12 | 6006 |
| LNCaP | R1881 treated | AR | 3.23 | 44536 |
| LNCaP | | ERG | 4.5 | 608 |
| RWPE | ERG overexpression | ERG | 3.95 | 10765 |
| RWPE | Control GUS | ERG | 2.72 | 1184 |
| Tissue (WA18-31) | metastatic Pca | AR | 17.4 | 12036 |
| Tissue (WA18-31) | metastatic Pca | ERG | 18.47 | 6967 |
| Tissue (WA18-31) | metastatic Pca | 3mH3K4 | 11.85 | 31836 |

TABLE 2

Distribution of ChIPseq AR/ERG binding sites relative to TSS of the nearest genes (negative for upstream, positive for downstream). Shown are the number of binding sites at each distance bin.

| Distance of binding sites to TSS (kb) | AR-bound in LNCaP ethl-treated | AR-bound in LNCaP R1881-treated | AR-bound in VCaP ethl-treated | AR-bound in VCaP R1881-treated | ERG-bound in VCaP | ERG-bound in LNCaP | ERG-bound in RWPE + ERG | ERG-bound in RWPE + GUS |
|---|---|---|---|---|---|---|---|---|
| −199 | 2 | 9 | 2 | 5 | 11 | 1 | 1 | |
| −198 | 2 | 12 | 2 | 2 | 11 | | | 1 |
| −197 | | 10 | 2 | 7 | 7 | 1 | 6 | |
| −196 | 1 | 7 | | 6 | 7 | 2 | 2 | |
| −195 | 3 | 12 | 3 | 6 | 7 | | | 1 |

TABLE 2-continued

Distribution of ChIPseq AR/ERG binding sites relative to TSS of the nearest genes (negative for upstream, positive for downstream). Shown are the number of binding sites at each distance bin.

| Distance of binding sites to TSS (kb) | AR-bound in LNCaP ethl-treated | AR-bound in LNCaP R1881-treated | AR-bound in VCaP ethl-treated | AR-bound in VCaP R1881-treated | ERG-bound in VCaP | ERG-bound in LNCaP | ERG-bound in RWPE + ERG | ERG-bound in RWPE + GUS |
|---|---|---|---|---|---|---|---|---|
| −194 |   | 14 |   | 1 | 6 | 1 | 3 |   |
| −193 |   | 9 |   |   | 6 | 8 |   |   |
| −192 | 2 | 9 | 1 |   | 5 | 11 | 5 |   |
| −191 | 1 | 13 | 1 |   | 5 | 6 |   |   |
| −190 |   | 4 |   |   | 2 | 6 | 1 |   |
| −189 | 1 | 8 | 1 |   | 5 | 5 | 2 |   |
| −188 |   | 13 |   |   | 2 | 6 | 1 |   |
| −187 | 3 | 17 | 1 |   | 3 | 12 |   |   |
| −186 | 2 | 11 | 3 |   | 6 | 10 | 2 |   |
| −185 |   | 10 | 1 |   | 2 | 10 | 1 |   |
| −184 | 1 | 12 |   |   | 2 | 4 | 2 |   |
| −183 | 1 | 5 |   |   | 3 | 12 |   |   |
| −182 | 3 | 9 | 1 |   | 3 | 8 | 1 |   |
| −181 | 3 | 11 |   |   | 8 | 9 | 2 |   |
| −180 |   | 8 |   |   | 2 | 4 | 3 |   |
| −179 |   | 10 |   |   | 5 | 5 | 2 |   |
| −178 | 1 | 6 |   |   | 5 | 8 | 1 | 1 |
| −177 |   | 17 | 2 |   | 6 | 7 | 1 | 1 | 1 |
| −176 | 1 | 19 | 1 |   | 4 | 10 |   |   |
| −175 |   | 9 |   |   | 3 | 8 | 1 |   |
| −174 | 1 | 25 | 2 |   | 5 | 15 | 1 | 1 |
| −173 | 4 | 16 | 1 |   | 4 | 9 | 1 |   |
| −172 | 3 | 9 |   |   | 7 | 8 | 3 |   |
| −171 |   | 9 | 1 |   | 3 | 10 | 2 | 3 |
| −170 | 1 | 11 | 2 |   | 4 | 14 | 1 | 3 |
| −169 | 2 | 12 | 1 |   | 1 | 4 | 1 |   |
| −168 | 1 | 7 | 2 |   | 8 | 9 | 2 |   |
| −167 | 2 | 14 | 2 |   | 3 | 8 | 2 | 1 |
| −166 | 4 | 15 | 1 |   | 6 | 14 | 1 | 1 |
| −165 | 1 | 12 | 1 |   | 1 | 7 | 1 | 2 | 1 |
| −164 |   | 11 | 1 |   | 4 | 8 |   |   |
| −163 | 1 | 7 | 3 |   | 7 | 10 | 3 |   |
| −162 | 2 | 13 | 1 |   | 1 | 13 |   | 1 |
| −161 |   | 13 | 1 |   | 8 | 10 | 1 | 1 |
| −160 | 1 | 19 | 2 |   | 2 | 6 | 1 | 1 |
| −159 | 1 | 7 |   |   | 4 | 10 | 3 | 1 |
| −158 | 2 | 16 | 3 |   | 4 | 14 | 2 | 2 |
| −157 |   | 18 | 1 |   | 4 | 12 | 1 |   |
| −156 | 1 | 15 | 3 |   | 6 | 12 | 2 |   |
| −155 | 1 | 14 | 2 |   | 5 | 11 |   |   |
| −154 | 3 | 12 | 2 |   | 8 | 9 | 1 |   |
| −153 | 1 | 12 | 1 |   | 8 | 10 | 1 | 8 |
| −152 |   | 19 |   |   | 7 | 10 | 4 |   |
| −151 | 1 | 17 |   |   | 6 | 10 | 1 | 4 | 2 |
| −150 | 1 | 14 | 1 |   | 8 | 14 | 4 | 1 |
| −149 |   | 17 |   |   | 5 | 14 | 1 |   |
| −148 |   | 13 | 3 |   | 9 | 11 | 1 | 4 |
| −147 | 3 | 14 |   |   | 6 | 18 | 1 | 2 |
| −146 | 3 | 19 | 3 |   | 8 | 12 | 1 | 2 |
| −145 | 1 | 14 | 1 |   | 6 | 9 | 1 | 4 | 1 |
| −144 | 4 | 17 | 2 |   | 11 | 12 | 1 | 4 | 2 |
| −143 | 3 | 20 |   |   | 8 | 14 | 1 | 2 |
| −142 | 3 | 27 | 2 |   | 5 | 15 | 2 | 2 | 1 |
| −141 | 2 | 27 |   |   | 6 | 18 | 1 | 4 |
| −140 | 1 | 17 |   |   | 5 | 11 |   | 4 |
| −139 | 3 | 20 |   |   | 4 | 18 | 1 | 4 | 1 |
| −138 |   | 9 | 1 |   | 10 | 11 | 2 |   |
| −137 | 1 | 20 | 1 |   | 5 | 18 | 1 |   |
| −136 | 1 | 18 | 4 |   | 12 | 14 | 1 | 1 |
| −135 | 1 | 16 | 1 |   | 6 | 10 | 5 | 1 |
| −134 | 2 | 24 | 2 |   | 16 | 19 | 1 | 1 |
| −133 | 3 | 20 | 1 |   | 10 | 14 | 2 | 8 |
| −132 | 3 | 12 |   |   | 6 | 14 | 3 | 1 |
| −131 |   | 13 | 1 |   | 7 | 14 | 3 | 1 |
| −130 | 2 | 26 | 2 |   | 12 | 22 | 1 | 2 |
| −129 | 2 | 18 | 1 |   | 7 | 19 | 4 |   |
| −128 | 1 | 22 | 1 |   | 9 | 17 | 2 |   |
| −127 | 3 | 23 | 3 |   | 6 | 16 | 3 | 1 |
| −126 | 3 | 26 | 1 |   | 9 | 20 | 5 |   |

TABLE 2-continued

Distribution of ChIPseq AR/ERG binding sites relative to TSS of the nearest genes (negative for upstream, positive for downstream). Shown are the number of binding sites at each distance bin.

| Distance of binding sites to TSS (kb) | AR-bound in LNCaP eth1-treated | AR-bound in LNCaP R1881-treated | AR-bound in VCaP eth1-treated | AR-bound in VCaP R1881-treated | ERG-bound in VCaP | ERG-bound in LNCaP | ERG-bound in RWPE + ERG | ERG-bound in RWPE + GUS |
|---|---|---|---|---|---|---|---|---|
| −125 | 4 | 27 | 3 | 10 | 18 | | 2 | 1 |
| −124 | 1 | 17 | 2 | 16 | 15 | 1 | 4 | |
| −123 | 4 | 31 | 5 | 9 | 11 | 1 | 2 | 1 |
| −122 | 3 | 16 | 6 | 12 | 24 | | 5 | |
| −121 | 3 | 17 | 2 | 10 | 17 | | | 1 |
| −120 | 3 | 20 | 1 | 9 | 21 | 2 | 6 | 1 |
| −119 | 3 | 25 | 4 | 5 | 17 | 3 | 1 | 3 |
| −118 | 1 | 31 | 1 | 11 | 19 | | 8 | 1 |
| −117 | 5 | 17 | 1 | 11 | 15 | | 2 | 1 |
| −116 | 4 | 17 | 2 | 13 | 17 | 1 | 7 | |
| −115 | 5 | 21 | 1 | 13 | 18 | | 4 | |
| −114 | 8 | 22 | 1 | 9 | 22 | 2 | 8 | 1 |
| −113 | 1 | 30 | 3 | 8 | 27 | | 7 | 1 |
| −112 | 5 | 20 | 1 | 14 | 29 | | 4 | 1 |
| −111 | 2 | 29 | 1 | 13 | 22 | | 4 | |
| −110 | 6 | 19 | 4 | 11 | 24 | | 7 | |
| −109 | 1 | 27 | 2 | 13 | 23 | | 4 | 1 |
| −108 | 2 | 38 | 2 | 26 | 24 | 1 | 3 | |
| −107 | 7 | 34 | 3 | 19 | 23 | | 9 | |
| −106 | 6 | 37 | 1 | 18 | 31 | 2 | 8 | 3 |
| −105 | 8 | 20 | 5 | 18 | 28 | 2 | 6 | 2 |
| −104 | 5 | 36 | 4 | 10 | 28 | | 6 | 1 |
| −103 | 7 | 43 | 3 | 16 | 27 | 2 | 8 | 1 |
| −102 | 3 | 28 | 2 | 11 | 24 | 1 | 9 | 1 |
| −101 | | 28 | | 10 | 31 | 3 | 6 | 3 |
| −100 | 3 | 30 | 2 | 16 | 32 | 1 | 11 | 2 |
| −99 | 3 | 20 | 1 | 14 | 45 | 2 | 13 | 1 |
| −98 | 7 | 33 | 5 | 16 | 51 | 4 | 17 | |
| −97 | 5 | 28 | 1 | 24 | 50 | 4 | 17 | |
| −96 | 4 | 39 | 5 | 16 | 51 | 3 | 15 | 3 |
| −95 | 6 | 36 | 2 | 11 | 51 | 2 | 12 | 2 |
| −94 | 5 | 24 | 7 | 23 | 57 | 3 | 13 | 2 |
| −93 | 6 | 42 | 1 | 18 | 58 | 1 | 17 | 3 |
| −92 | 3 | 37 | 3 | 12 | 49 | 3 | 16 | 2 |
| −91 | 3 | 31 | | 12 | 42 | 1 | 13 | |
| −90 | 4 | 27 | 2 | 16 | 47 | 4 | 19 | 1 |
| −89 | 3 | 39 | 4 | 18 | 48 | 2 | 13 | 1 |
| −88 | 3 | 31 | 2 | 14 | 44 | 5 | 17 | 1 |
| −87 | 6 | 31 | 5 | 18 | 44 | 6 | 15 | 3 |
| −86 | 8 | 30 | 3 | 23 | 54 | | 10 | |
| −85 | 6 | 48 | 4 | 21 | 48 | 3 | 13 | 2 |
| −84 | 4 | 47 | 1 | 13 | 57 | 3 | 21 | 2 |
| −83 | 6 | 36 | 1 | 22 | 59 | 2 | 13 | 3 |
| −82 | 10 | 35 | 6 | 20 | 71 | 1 | 16 | 3 |
| −81 | 6 | 39 | 3 | 21 | 47 | 5 | 15 | 1 |
| −80 | 6 | 47 | 2 | 22 | 60 | 6 | 19 | 2 |
| −79 | 4 | 35 | 4 | 22 | 65 | 6 | 19 | 2 |
| −78 | 6 | 39 | | 16 | 51 | 2 | 16 | |
| −77 | 8 | 37 | 4 | 19 | 62 | 2 | 14 | 3 |
| −76 | 3 | 34 | 2 | 19 | 56 | 5 | 20 | 3 |
| −75 | 9 | 36 | 6 | 27 | 71 | 10 | 23 | 7 |
| −74 | 7 | 35 | 2 | 16 | 67 | 4 | 18 | 1 |
| −73 | 6 | 35 | 3 | 17 | 64 | 3 | 17 | 1 |
| −72 | 2 | 50 | | 18 | 57 | 2 | 13 | 1 |
| −71 | 9 | 49 | 1 | 22 | 63 | 3 | 14 | 2 |
| −70 | 5 | 35 | 1 | 20 | 69 | 6 | 23 | 2 |
| −69 | 10 | 33 | 4 | 18 | 60 | 5 | 26 | 2 |
| −68 | 5 | 42 | 5 | 32 | 72 | 4 | 10 | 4 |
| −67 | 4 | 52 | 2 | 22 | 65 | 4 | 27 | 5 |
| −66 | 6 | 54 | 4 | 21 | 60 | 2 | 15 | 3 |
| −65 | 7 | 41 | 4 | 33 | 99 | 3 | 27 | 4 |
| −64 | 6 | 53 | 3 | 22 | 80 | 1 | 22 | 2 |
| −63 | 9 | 52 | 4 | 22 | 77 | 5 | 21 | 3 |
| −62 | 5 | 49 | 2 | 26 | 72 | 4 | 14 | |
| −61 | 4 | 60 | 3 | 23 | 69 | 6 | 24 | 3 |
| −60 | 5 | 43 | 3 | 23 | 76 | 6 | 20 | 3 |
| −59 | 5 | 55 | 4 | 25 | 65 | 3 | 25 | 2 |
| −58 | 6 | 46 | 4 | 30 | 77 | 5 | 21 | 2 |
| −57 | 5 | 51 | 2 | 23 | 78 | 4 | 27 | 3 |

TABLE 2-continued

Distribution of ChIPseq AR/ERG binding sites relative to TSS of the nearest genes (negative for upstream, positive for downstream). Shown are the number of binding sites at each distance bin.

| Distance of binding sites to TSS (kb) | AR-bound in LNCaP ethl-treated | AR-bound in LNCaP R1881-treated | AR-bound in VCaP ethl-treated | AR-bound in VCaP R1881-treated | ERG-bound in VCaP | ERG-bound in LNCaP | ERG-bound in RWPE + ERG | ERG-bound in RWPE + GUS |
|---|---|---|---|---|---|---|---|---|
| −56 | 7 | 48 | 4 | 23 | 81 | 2 | 22 | 1 |
| −55 | 6 | 53 | 10 | 32 | 75 | 5 | 16 | 3 |
| −54 | 10 | 52 | 5 | 31 | 95 | 5 | 24 | 5 |
| −53 | 6 | 56 | 7 | 28 | 92 | 7 | 32 | 6 |
| −52 | 7 | 53 | 9 | 32 | 95 | 3 | 18 | 2 |
| −51 | 10 | 44 | 6 | 23 | 92 | 3 | 26 | 3 |
| −50 | 7 | 58 | 4 | 42 | 83 | 3 | 31 | 5 |
| −49 | 11 | 49 | 8 | 26 | 100 | 10 | 35 | 8 |
| −48 | 9 | 55 | 5 | 31 | 92 | 6 | 27 | 3 |
| −47 | 5 | 61 | 4 | 30 | 102 | 5 | 30 | 2 |
| −46 | 8 | 79 | 1 | 38 | 99 | 6 | 38 | 7 |
| −45 | 9 | 54 | 3 | 28 | 104 | 5 | 36 | 2 |
| −44 | 5 | 58 | 3 | 24 | 87 |  | 32 | 3 |
| −43 | 15 | 70 | 5 | 36 | 91 | 5 | 32 | 3 |
| −42 | 4 | 67 | 2 | 35 | 71 | 3 | 30 | 1 |
| −41 | 14 | 56 | 5 | 40 | 113 | 7 | 40 | 1 |
| −40 | 14 | 59 | 7 | 44 | 129 | 7 | 40 | 6 |
| −39 | 10 | 66 | 6 | 40 | 109 | 5 | 35 | 4 |
| −38 | 9 | 68 | 2 | 31 | 110 | 7 | 41 | 5 |
| −37 | 11 | 62 | 4 | 37 | 118 | 9 | 23 | 2 |
| −36 | 11 | 77 | 4 | 37 | 117 | 5 | 46 | 3 |
| −35 | 12 | 66 | 5 | 32 | 106 | 8 | 32 | 2 |
| −34 | 9 | 67 | 7 | 31 | 101 | 7 | 37 | 5 |
| −33 | 8 | 66 | 6 | 28 | 120 | 9 | 42 | 7 |
| −32 | 21 | 68 | 9 | 43 | 134 | 12 | 47 | 12 |
| −31 | 11 | 71 | 11 | 43 | 147 | 14 | 47 | 7 |
| −30 | 13 | 73 | 5 | 40 | 146 | 9 | 54 | 9 |
| −29 | 11 | 67 | 5 | 44 | 129 | 9 | 28 | 6 |
| −28 | 9 | 81 | 10 | 45 | 131 | 10 | 45 | 7 |
| −27 | 13 | 79 | 3 | 45 | 160 | 7 | 54 | 7 |
| −26 | 12 | 79 | 6 | 49 | 140 | 11 | 54 | 6 |
| −25 | 19 | 80 | 5 | 52 | 167 | 13 | 63 | 8 |
| −24 | 20 | 92 | 8 | 51 | 146 | 13 | 43 | 4 |
| −23 | 15 | 76 | 5 | 52 | 153 | 12 | 55 | 10 |
| −22 | 10 | 75 | 4 | 48 | 144 | 11 | 53 | 2 |
| −21 | 8 | 79 | 5 | 56 | 161 | 16 | 62 | 5 |
| −20 | 14 | 89 | 10 | 46 | 171 | 18 | 68 | 8 |
| −19 | 13 | 97 | 9 | 68 | 160 | 8 | 53 | 8 |
| −18 | 15 | 73 | 11 | 61 | 189 | 17 | 64 | 13 |
| −17 | 18 | 103 | 13 | 66 | 194 | 11 | 70 | 7 |
| −16 | 19 | 111 | 11 | 60 | 204 | 16 | 72 | 12 |
| −15 | 20 | 103 | 10 | 53 | 223 | 21 | 82 | 12 |
| −14 | 20 | 88 | 17 | 72 | 217 | 12 | 78 | 10 |
| −13 | 13 | 87 | 7 | 70 | 207 | 17 | 72 | 15 |
| −12 | 23 | 121 | 15 | 76 | 208 | 21 | 70 | 10 |
| −11 | 15 | 124 | 12 | 90 | 226 | 20 | 73 | 11 |
| −10 | 16 | 94 | 14 | 71 | 261 | 19 | 82 | 18 |
| −9 | 16 | 113 | 18 | 104 | 243 | 12 | 92 | 11 |
| −8 | 18 | 116 | 9 | 98 | 230 | 18 | 92 | 12 |
| −7 | 19 | 130 | 14 | 103 | 264 | 19 | 92 | 12 |
| −6 | 20 | 121 | 14 | 94 | 299 | 20 | 112 | 12 |
| −5 | 28 | 120 | 14 | 87 | 296 | 29 | 95 | 9 |
| −4 | 27 | 144 | 25 | 110 | 332 | 30 | 117 | 10 |
| −3 | 30 | 138 | 11 | 125 | 367 | 23 | 111 | 19 |
| −2 | 33 | 159 | 21 | 157 | 431 | 37 | 173 | 31 |
| −1 | 52 | 173 | 39 | 204 | 427 | 70 | 288 | 56 |
| 0 | 523 | 799 | 290 | 1247 | 6359 | 837 | 4442 | 511 |
| 1 | 90 | 301 | 177 | 1325 | 5220 | 372 | 1241 | 183 |
| 2 | 34 | 213 | 60 | 472 | 1029 | 60 | 188 | 27 |
| 3 | 24 | 150 | 36 | 243 | 350 | 17 | 79 | 19 |
| 4 | 26 | 169 | 29 | 137 | 255 | 15 | 76 | 10 |
| 5 | 23 | 220 | 20 | 125 | 191 | 11 | 63 | 9 |
| 6 | 17 | 132 | 18 | 112 | 168 | 8 | 55 | 14 |
| 7 | 18 | 145 | 16 | 87 | 154 | 11 | 46 | 8 |
| 8 | 17 | 148 | 12 | 82 | 149 | 8 | 46 | 12 |
| 9 | 22 | 139 | 14 | 89 | 127 | 8 | 55 | 5 |
| 10 | 20 | 117 | 6 | 69 | 141 | 11 | 50 | 6 |
| 11 | 16 | 120 | 11 | 59 | 126 | 8 | 56 | 8 |
| 12 | 15 | 123 | 8 | 69 | 121 | 5 | 43 | 9 |

TABLE 2-continued

Distribution of ChIPseq AR/ERG binding sites relative to TSS of the nearest genes (negative for upstream, positive for downstream). Shown are the number of binding sites at each distance bin.

| Distance of binding sites to TSS (kb) | AR-bound in LNCaP ethl-treated | AR-bound in LNCaP R1881-treated | AR-bound in VCaP ethl-treated | AR-bound in VCaP R1881-treated | ERG-bound in VCaP | ERG-bound in LNCaP | ERG-bound in RWPE + ERG | ERG-bound in RWPE + GUS |
|---|---|---|---|---|---|---|---|---|
| 13 | 17 | 134 | 11 | 62 | 127 | 10 | 31 | 6 |
| 14 | 21 | 126 | 9 | 67 | 119 | 5 | 32 | 6 |
| 15 | 17 | 137 | 7 | 56 | 126 | 7 | 34 | 8 |
| 16 | 13 | 114 | 10 | 49 | 87 | 3 | 27 | 1 |
| 17 | 15 | 109 | 5 | 57 | 99 | 4 | 24 | 3 |
| 18 | 10 | 107 | 8 | 55 | 95 | 7 | 32 | 3 |
| 19 | 11 | 109 | 11 | 38 | 88 | 2 | 27 | 4 |
| 20 | 15 | 97 | 5 | 49 | 93 | 5 | 26 | 3 |
| 21 | 10 | 97 | 8 | 42 | 96 | 7 | 26 | 5 |
| 22 | 13 | 98 | 9 | 45 | 94 | 6 | 36 | 5 |
| 23 | 12 | 100 | 4 | 47 | 78 | 2 | 25 | 2 |
| 24 | 11 | 99 | 6 | 48 | 78 | 1 | 24 | 5 |
| 25 | 11 | 105 | 9 | 34 | 75 | 7 | 25 | 3 |
| 26 | 9 | 105 | 7 | 47 | 78 | 4 | 30 | 4 |
| 27 | 8 | 86 | 7 | 46 | 76 | 2 | 29 | 3 |
| 28 | 11 | 90 | 7 | 49 | 70 | 7 | 19 | 3 |
| 29 | 10 | 76 | 5 | 28 | 83 | 5 | 16 | 2 |
| 30 | 11 | 78 | 6 | 37 | 84 | 6 | 21 | 3 |
| 31 | 14 | 101 | 7 | 31 | 60 | 3 | 19 | 3 |
| 32 | 10 | 86 | 2 | 40 | 61 | 3 | 24 | 3 |
| 33 | 11 | 94 | 5 | 42 | 68 | 2 | 18 | 3 |
| 34 | 4 | 79 | 3 | 27 | 68 | 3 | 18 | 1 |
| 35 | 17 | 68 | 5 | 22 | 61 | 2 | 16 | 2 |
| 36 | 7 | 79 | 4 | 33 | 55 | 2 | 18 | 3 |
| 37 | 11 | 88 | 3 | 34 | 60 | 1 | 12 | 3 |
| 38 | 10 | 72 | 2 | 25 | 63 | 5 | 12 | 2 |
| 39 | 6 | 57 | 8 | 31 | 58 | 3 | 13 | 4 |
| 40 | 7 | 65 | 3 | 33 | 56 | 5 | 10 | 4 |
| 41 | 9 | 76 | 5 | 21 | 57 | 2 | 18 | 1 |
| 42 | 12 | 65 | 5 | 26 | 53 | 3 | 13 | 3 |
| 43 | 8 | 73 | 4 | 22 | 52 |   | 13 | 1 |
| 44 | 5 | 58 | 3 | 19 | 40 | 2 | 16 | 5 |
| 45 | 6 | 69 | 2 | 31 | 61 | 3 | 11 | 2 |
| 46 | 8 | 56 | 4 | 20 | 38 | 3 | 14 | 5 |
| 47 | 4 | 53 | 5 | 22 | 54 |   | 14 | 4 |
| 48 | 4 | 55 | 2 | 22 | 47 |   | 13 | 1 |
| 49 | 7 | 61 | 6 | 26 | 36 |   | 10 | 1 |
| 50 | 6 | 77 | 8 | 22 | 47 | 3 | 11 | 2 |
| 51 | 6 | 50 | 2 | 23 | 31 | 4 | 6 | 2 |
| 52 | 6 | 54 | 2 | 20 | 45 |   | 9 | 2 |
| 53 | 6 | 61 | 5 | 20 | 35 | 3 | 11 | 2 |
| 54 | 4 | 56 | 4 | 16 | 38 | 3 | 14 | 1 |
| 55 | 7 | 41 | 1 | 16 | 33 |   | 7 | 2 |
| 56 | 6 | 55 | 3 | 24 | 39 |   | 5 | 3 |
| 57 | 8 | 59 | 3 | 14 | 45 | 1 | 9 | 1 |
| 58 | 5 | 60 |   | 25 | 40 |   | 7 | 2 |
| 59 | 6 | 58 | 2 | 16 | 41 | 1 | 10 | 1 |
| 60 | 7 | 43 | 1 | 19 | 35 | 2 | 11 | 2 |
| 61 | 6 | 36 | 5 | 24 | 45 | 3 | 12 | 2 |
| 62 | 7 | 49 | 2 | 20 | 36 | 3 | 9 | 1 |
| 63 | 4 | 40 | 4 | 18 | 29 |   | 8 | 2 |
| 64 | 3 | 52 | 2 | 11 | 31 | 2 | 8 | 3 |
| 65 | 6 | 50 | 2 | 15 | 31 |   | 8 |   |
| 66 | 3 | 39 | 3 | 20 | 37 | 1 | 10 |   |
| 67 | 5 | 37 | 4 | 19 | 38 | 1 | 10 | 2 |
| 68 | 2 | 47 | 2 | 15 | 30 | 2 | 7 |   |
| 69 | 6 | 47 | 3 | 18 | 44 | 2 | 9 | 1 |
| 70 | 6 | 45 | 3 | 16 | 39 | 2 | 12 |   |
| 71 |   | 43 | 3 | 11 | 27 | 1 | 3 |   |
| 72 | 3 | 43 | 4 | 22 | 29 | 4 | 8 | 1 |
| 73 | 5 | 57 | 2 | 19 | 34 | 1 | 5 | 2 |
| 74 | 4 | 37 | 1 | 12 | 37 | 1 | 7 | 1 |
| 75 | 5 | 34 | 2 | 18 | 29 | 1 | 10 | 1 |
| 76 | 5 | 39 | 3 | 19 | 29 | 2 | 7 | 1 |
| 77 | 9 | 48 | 3 | 15 | 35 | 2 | 7 |   |
| 78 | 2 | 31 | 5 | 18 | 32 | 1 | 7 | 1 |
| 79 | 5 | 37 | 2 | 19 | 30 | 2 | 11 | 3 |
| 80 | 6 | 36 | 4 | 7 | 24 | 1 | 5 | 1 |
| 81 | 6 | 35 | 4 | 15 | 21 |   | 9 | 2 |

TABLE 2-continued

Distribution of ChIPseq AR/ERG binding sites relative to TSS of the nearest genes (negative for upstream, positive for downstream). Shown are the number of binding sites at each distance bin.

| Distance of binding sites to TSS (kb) | AR-bound in LNCaP ethl-treated | AR-bound in LNCaP R1881-treated | AR-bound in VCaP ethl-treated | AR-bound in VCaP R1881-treated | ERG-bound in VCaP | ERG-bound in LNCaP | ERG-bound in RWPE + ERG | ERG-bound in RWPE + GUS |
|---|---|---|---|---|---|---|---|---|
| 82 | 2 | 49 | 2 | 9 | 26 | | 7 | 1 |
| 83 | 4 | 39 | 2 | 19 | 26 | | 9 | 1 |
| 84 | 3 | 32 | 1 | 12 | 31 | 2 | 10 | 2 |
| 85 | 5 | 39 | 5 | 10 | 26 | | 12 | 3 |
| 86 | 3 | 40 | 3 | 12 | 20 | | 5 | |
| 87 | 2 | 31 | 2 | 18 | 27 | 1 | 3 | |
| 88 | 4 | 34 | 3 | 8 | 22 | 1 | 8 | 2 |
| 89 | 4 | 33 | 1 | 8 | 22 | | 4 | 1 |
| 90 | 4 | 33 | | 11 | 30 | | 7 | 1 |
| 91 | 2 | 41 | 3 | 16 | 15 | | 4 | 1 |
| 92 | 4 | 28 | 1 | 14 | 21 | 1 | 4 | 2 |
| 93 | 6 | 36 | 1 | 10 | 24 | | 4 | |
| 94 | 4 | 27 | 2 | 6 | 23 | | 7 | 1 |
| 95 | 2 | 28 | 2 | 19 | 24 | | 11 | |
| 96 | 6 | 35 | 5 | 9 | 22 | 1 | 12 | 2 |
| 97 | 2 | 27 | 2 | 5 | 19 | 1 | 5 | |
| 98 | 3 | 27 | 3 | 11 | 21 | | 6 | 1 |
| 99 | 6 | 34 | 2 | 12 | 23 | | 11 | 1 |
| 100 | 3 | 19 | | 7 | 18 | 2 | 5 | |
| 101 | 2 | 24 | 3 | 18 | 21 | 1 | 4 | 1 |
| 102 | 2 | 23 | 2 | 10 | 18 | 1 | 1 | 1 |
| 103 | 6 | 28 | 1 | 8 | 11 | | 6 | 1 |
| 104 | 4 | 30 | 5 | 15 | 26 | | 2 | 2 |
| 105 | 3 | 20 | 2 | 9 | 20 | 1 | 6 | 3 |
| 106 | 2 | 31 | 4 | 13 | 14 | | 2 | |
| 107 | 4 | 34 | | 14 | 24 | 1 | 4 | 1 |
| 108 | 2 | 26 | 2 | 9 | 17 | | 6 | |
| 109 | 1 | 24 | 3 | 7 | 19 | 2 | 7 | 2 |
| 110 | 2 | 18 | | 9 | 16 | 1 | 5 | 1 |
| 111 | 5 | 27 | 3 | 6 | 17 | 1 | 4 | 1 |
| 112 | 2 | 23 | 2 | 11 | 14 | 1 | 5 | |
| 113 | | 26 | 1 | 8 | 30 | | 2 | 1 |
| 114 | 1 | 23 | 2 | 9 | 24 | | 5 | |
| 115 | 5 | 29 | 3 | 15 | 19 | | 8 | 1 |
| 116 | 1 | 27 | | 9 | 13 | | 3 | |
| 117 | 3 | 19 | 6 | 5 | 11 | 1 | 5 | |
| 118 | 7 | 22 | 3 | 14 | 17 | 2 | 4 | 4 |
| 119 | 1 | 21 | 3 | 6 | 18 | 1 | 7 | |
| 120 | 1 | 20 | 3 | 8 | 25 | | 7 | |
| 121 | 3 | 21 | 2 | 12 | 10 | | 3 | |
| 122 | 1 | 20 | 1 | 11 | 14 | 1 | 7 | 1 |
| 123 | 3 | 21 | 2 | 8 | 11 | | 5 | 1 |
| 124 | 4 | 29 | 1 | 8 | 24 | 1 | 4 | |
| 125 | 1 | 15 | 2 | 4 | 16 | | 3 | 1 |
| 126 | 3 | 16 | | 11 | 15 | | 3 | |
| 127 | 3 | 22 | | 7 | 17 | | 2 | |
| 128 | 2 | 24 | 1 | 7 | 13 | | 5 | |
| 129 | 1 | 20 | | 8 | 11 | 1 | 3 | |
| 130 | 1 | 23 | 4 | 4 | 17 | 1 | 1 | |
| 131 | 1 | 23 | 3 | 9 | 19 | 2 | 4 | |
| 132 | 2 | 17 | | 11 | 14 | | 3 | 3 |
| 133 | 1 | 14 | 1 | 7 | 17 | | 2 | 1 |
| 134 | 3 | 22 | 1 | 10 | 12 | 1 | 9 | |
| 135 | 7 | 24 | 1 | 9 | 20 | 1 | 4 | 1 |
| 136 | 1 | 25 | 2 | 15 | 22 | | 5 | |
| 137 | 6 | 25 | 1 | 13 | 17 | | 3 | 1 |
| 138 | | 19 | 1 | 12 | 18 | | 2 | 1 |
| 139 | 5 | 22 | 1 | 7 | 12 | | 2 | |
| 140 | 2 | 20 | 2 | 7 | 19 | | 2 | |
| 141 | 2 | 18 | 2 | 7 | 6 | 1 | 2 | |
| 142 | 1 | 20 | | 5 | 11 | | | 2 |
| 143 | 2 | 16 | 3 | 8 | 15 | | 5 | |
| 144 | 5 | 16 | | 6 | 13 | | 4 | 1 |
| 145 | | 11 | 1 | 6 | 16 | 1 | 3 | |
| 146 | | 17 | 4 | 7 | 11 | | 4 | |
| 147 | 6 | 22 | 1 | 6 | 12 | | 4 | |
| 148 | 6 | 14 | 2 | 4 | 11 | | 3 | |
| 149 | 3 | 13 | | 10 | 12 | | 2 | 1 |
| 150 | 2 | 19 | 1 | 7 | 11 | 1 | | |

TABLE 2-continued

Distribution of ChIPseq AR/ERG binding sites relative to TSS of the nearest genes (negative for upstream, positive for downstream). Shown are the number of binding sites at each distance bin.

| Distance of binding sites to TSS (kb) | AR-bound in LNCaP ethl-treated | AR-bound in LNCaP R1881-treated | AR-bound in VCaP ethl-treated | AR-bound in VCaP R1881-treated | ERG-bound in VCaP | ERG-bound in LNCaP | ERG-bound in RWPE + ERG | ERG-bound in RWPE + GUS |
|---|---|---|---|---|---|---|---|---|
| 151 | 3 | 15 | 1 | 6 | 11 |   | 3 |   |
| 152 |   | 14 | 1 | 4 | 6 | 1 | 5 |   |
| 153 | 2 | 12 | 2 | 8 | 20 | 1 | 3 |   |
| 154 | 3 | 26 | 1 | 7 | 7 |   | 4 |   |
| 155 | 1 | 19 | 1 | 7 | 13 |   | 4 |   |
| 156 | 1 | 13 |   | 1 | 4 | 1 | 1 |   |
| 157 | 1 | 13 | 3 | 7 | 10 |   | 3 | 1 |
| 158 | 3 | 19 | 2 | 3 | 11 |   | 4 |   |
| 159 | 2 | 16 |   | 8 | 5 | 1 | 2 | 1 |
| 160 | 4 | 16 | 2 | 8 | 8 | 2 | 3 |   |
| 161 | 2 | 9 |   | 2 | 10 | 2 | 1 |   |
| 162 | 2 | 16 |   | 3 | 9 |   | 1 |   |
| 163 | 3 | 14 |   | 5 | 10 |   | 3 | 1 |
| 164 | 1 | 5 | 1 | 5 | 11 | 2 | 3 |   |
| 165 | 1 | 15 | 1 | 7 | 9 | 1 | 3 | 1 |
| 166 | 2 | 15 | 2 | 5 | 9 | 1 |   |   |
| 167 | 4 | 10 |   | 3 | 12 |   | 3 |   |
| 168 | 1 | 8 | 1 | 3 | 9 |   | 1 | 1 |
| 169 |   | 15 |   | 5 | 15 |   | 3 | 1 |
| 170 |   | 14 | 1 | 2 | 5 |   | 2 |   |
| 171 | 2 | 14 |   | 6 | 15 | 1 | 2 | 2 |
| 172 | 2 | 16 |   | 6 | 13 |   | 3 |   |
| 173 | 1 | 17 |   | 6 | 11 |   |   | 1 |
| 174 | 1 | 13 |   | 7 | 5 | 1 | 5 | 1 |
| 175 |   | 10 |   | 4 | 10 |   | 4 |   |
| 176 | 1 | 11 |   | 3 | 8 |   | 2 |   |
| 177 | 2 | 15 | 1 | 3 | 8 |   | 4 | 1 |
| 178 | 1 | 7 |   | 4 | 12 |   | 2 |   |
| 179 | 2 | 10 |   | 5 | 10 |   | 2 |   |
| 180 |   | 11 | 1 | 7 | 10 |   | 1 | 2 |
| 181 | 3 | 14 | 1 | 5 | 14 |   | 3 |   |
| 182 | 2 | 12 |   | 8 | 11 |   | 1 |   |
| 183 | 1 | 10 | 1 | 1 | 5 |   | 3 | 1 |
| 184 | 4 | 11 |   | 6 | 10 |   | 3 | 1 |
| 185 | 2 | 11 |   | 6 | 11 |   | 3 |   |
| 186 | 2 | 16 | 1 | 4 | 6 |   | 2 | 1 |
| 187 | 2 | 19 | 1 | 4 | 10 |   | 1 |   |
| 188 | 2 | 12 |   | 2 | 10 |   | 1 |   |
| 189 | 2 | 9 | 1 | 5 | 6 |   | 2 | 1 |
| 190 | 1 | 7 |   | 6 | 8 |   |   |   |
| 191 | 1 | 14 |   | 2 | 2 |   | 1 |   |
| 192 | 1 | 19 |   | 1 | 7 |   |   |   |
| 193 | 1 | 10 | 1 | 3 | 6 |   | 1 |   |
| 194 | 1 | 11 |   | 1 | 9 | 1 | 1 |   |
| 195 | 4 | 9 | 1 | 5 | 7 | 2 |   |   |
| 196 | 1 | 10 | 1 |   | 6 |   | 1 |   |
| 197 | 1 | 8 |   | 2 | 8 |   |   | 1 |
| 198 |   | 15 | 1 | 3 | 3 |   | 1 |   |
| 199 | 2 | 8 | 1 | 2 | 11 |   | 1 |   |

TABLE 3

The top motifs (and p values by Fisher's exact test) contained in the binding sequences of AR or ERG in different datasets. Top AR binding motifs are in yellow and ETS binding motifs in green.

| LNCaP AR-bound | | | VCaP AR-Bound | | | VCaP ERG-Bound | | | RWPE + ERG ERG-Bound | | |
|---|---|---|---|---|---|---|---|---|---|---|---|
| Genomatix motif | Related TF | p value | Genomatix motif | Related TF | p value | Genomatix motif | Related TF | p value | Genomatix motif | Related TF | p value |
| V$ARE.02 | AR | 0 | V$ARE.02 | AR | 0 | V$ELF2.01 | ETS | 0 | V$ETS1.01 | ETS | 0 |
| V$ARE.01 | AR | 0 | V$GRE.01 | AR | 0 | V$PEA3.01 | ETS | 0 | V$ELF2.01 | ETS | 0 |
| V$GRE.01 | AR | 0 | V$ETS2.01 | ETS | 0 | V$ETS2.01 | ETS | 0 | V$PEA3.01 | ETS | 1.37E−267 |
| V$PRE.01 | AR | 0 | V$ARE.01 | AR | 0 | V$ETS1.01 | ETS | 0 | V$ETS2.01 | ETS | 1.41E−256 |

TABLE 3-continued

The top motifs (and p values by Fisher's exact test) contained in the binding sequences of AR or ERG in different datasets. Top AR binding motifs are in yellow and ETS binding motifs in green.

| V$FREAC4.01 | FKHD | 0 | V$ELF2.01 | ETS | 0 | V$GABP.01 | ETS | 0 | V$ELK1.01 | EST | 4.17E−244 |
| V$ETS2.01 | ETS | 0 | V$PEA3.01 | ETS | 0 | V$PU1.01 | ETS | 0 | V$GABP.01 | ETS | 8.62E−234 |
| V$FKHRL1.01 | FKHD | 0 | V$PRE.01 | AR | 0 | V$ELK1.01 | ETS | 0 | V$CETS1P54.01 | ETS | 2.03E−223 |
| V$PEA3.01 | ETS | 0 | V$ETS1.01 | ETS | 9.08E−298 | V$CKROX.01 | CKROX | 0 | V$NRF2.01 | ETS | 9.98E−208 |
| V$NFAT.01 | NFAT | 0 | V$FREAC4.01 | FKHD | 5.82E−229 | V$SPIB.01 | ETS | 0 | V$ELK1.02 | ETS | 1.32E−204 |
| V$ELF2.01 | ETS | 0 | V$PU1.01 | ETS | 6.50E−229 | V$NFAT.01 | NFAT | 0 | V$SPI1_PU1.02 | ETS | 1.88E−165 |

| | NRSF Bound | | | AR-bound in LNCaP and VCaP | | | AR-bound and ERG-bound in VCaP | |
|---|---|---|---|---|---|---|---|---|
| Genomatix motif | Related TF | p value | Genomatix motif | Related TF | p value | Genomatix motif | Related TF | p value |
| V$NRSF.01 | NRSF | 0 | V$ARE.02 | AR | 0 | V$ELF2.01 | ETS | 5.84E−255 |
| V$PEA3.01 | ETS | 4.74E−132 | V$ARE.01 | AR | 0 | V$ETS2.01 | ETS | 7.03E−255 |
| V$ELF2.01 | ETS | 5.63E−107 | V$GRE.01 | AR | 0 | V$PEA3.01 | ETS | 1.07E−240 |
| V$ZNF202.01 | ZBPF | 1.07E−80 | V$PRE.01 | AR | 5.97E−290 | V$ARE.02 | AR | 8.06E−202 |
| V$PU1.01 | ETS | 5.18E−79 | V$ETS2.01 | ETS | 9.83E−211 | V$ETS1.01 | ETS | 9.84E−193 |
| V$CKROX.01 | CKROX | 9.71E−79 | V$FREAC4.01 | FKHD | 9.21E−202 | V$GRE.01 | AR | 7.03E−142 |
| V$ETS2.01 | ETS | 1.28E−77 | V$PEA3.01 | ETS | 7.73E−192 | V$ARE.01 | AR | 1.18E−134 |
| V$GAGA.01 | GABF | 2.93E−68 | V$ELF2.01 | ETS | 1.01E−182 | V$PRE.01 | AR | 6.97E−120 |
| V$NFAT.01 | NFAT | 7.87E−68 | V$FKHRL1.01 | FKHD | 2.07E−158 | V$PU1.01 | ETS | 1.36E−111 |
| V$GKLF.01 | GKLF | 8.10E−68 | V$XFD3.01 | FKHD | 7.31E−133 | V$ELK1.01 | ETS | 1.36E−101 |

TABLE 4

The percentage of occurrence of motifs in bound-sequences and its enrichment ratio over permutated datasets.

| | V$ARE.01 | V$ARE.02 | V$ETS1.01 | V$ETS2.01 |
|---|---|---|---|---|
| % ChIP-Seq binding sequence containing motif | | | | |
| LNCaP AR-bound | 35.7 | 36.1 | 14.7 | 26.9 |
| VCaP AR-bound | 31.1 | 33.2 | 21.5 | 28.7 |
| VCaP ERG-bound | 19.9 | 21.3 | 40.4 | 39.4 |
| RWPE + ERG ERG-bound | 13.8 | 17 | 53.4 | 40 |
| AR-bound in both LNCaP and VCaP | 41.9 | 43.9 | 18.5 | 30.2 |
| AR-bound in both LNCaP and VCaP, and androgen-responsive | 67.2 | 61.7 | 25 | 46.9 |
| AR-bound and ERG-bound in VCaP | 27.3 | 29.9 | 28.3 | 33.3 |
| AR-bound (Wang et al. 2007) | 34.2 | 26.3 | 10.5 | 14.5 |
| % permutated sequence containing motif | | | | |
| LNCaP AR-bound | 12.06 | 9.94 | 4.93 | 9.47 |
| VCaP AR-bound | 10.65 | 9.43 | 6.89 | 8.75 |
| VCaP ERG-bound | 11.78 | 9.95 | 10.83 | 9.83 |
| RWPE + ERG ERG-bound | 9.93 | 8.67 | 10.60 | 8.15 |
| AR-bound in both LNCaP and VCaP | 11.87 | 10.40 | 6.09 | 9.38 |
| AR-bound in both LNCaP and VCaP, and androgen-responsive | 16.39 | 14.05 | 13.30 | 14.08 |
| AR-bound and ERG-bound in VCaP | 9.51 | 7.99 | 7.43 | 7.93 |
| AR-bound (Wang et al. 2007) | 13.15 | 17.08 | 4.41 | 4.69 |

TABLE 5

MCM analysis of AR-bound genes in VCaP cells

| Group Type | Group ID | Group Name | Group Size | P-Value | Q-Value | Odds Ratio |
|---|---|---|---|---|---|---|
| My Concepts | 70857635 | AR-bound genes in LNCaP | 2889 | ######## | 4.19E−99 | 32.79 |
| Literature-defined Concepts | 148288 | Downregulated in Human Embryonic Stem Cells vs Differentiated Counterparts | 1047 | 3.80E−33 | 6.28E−31 | 2.69 |
| Literature-defined Concepts | 148291 | Trimethylated H3K27 occupancy in embryonic fibroblasts | 2451 | 1.80E−28 | 2.43E−26 | 1.96 |
| Oncomine Gene Expression Signatures | 58926416 | Melanoma Type - Top 20% under-expressed in Lymph Node Metastasis, Metastatic Growth Phase Melanoma, Metastatic Melanoma Culture (Smith) | 3680 | 8.60E−27 | 4.39E−24 | 1.69 |

TABLE 5-continued

MCM analysis of AR-bound genes in VCaP cells

| Group Type | Group ID | Group Name | Group Size | P-Value | Q-Value | Odds Ratio |
|---|---|---|---|---|---|---|
| Literature-defined Concepts | 148285 | Trimethylated H3K27 occupancy in stem cells | 1120 | 9.00E−27 | 9.96E−25 | 2.41 |
| Oncomine Gene Expression Signatures | 22233016 | Breast Carcinoma Histone Lysine H3mK27 Methylation - Top 10% over-expressed in Positive (Richardson) | 1880 | 2.80E−26 | 1.33E−23 | 1.93 |
| Oncomine Gene Expression Signatures | 22233136 | Breast Carcinoma Type - Top 10% under-expressed in Basal-like (Richardson) | 1880 | 2.60E−25 | 1.05E−22 | 1.9 |
| Oncomine Gene Expression Signatures | 40937976 | Bladder Grade - Top 20% under-expressed in High Grade (Dyrskjot) | 3260 | 9.40E−25 | 3.50E−22 | 1.69 |
| Literature-defined Concepts | 148286 | SUZ12 occupancy in stem cells | 1040 | 1.60E−22 | 1.36E−20 | 2.31 |
| Oncomine Gene Expression Signatures | 11632832 | Cancer Type - v1 - Top 10% under-expressed in Metastatic Melanoma (Bittner) | 1880 | 2.70E−20 | 5E−18 | 1.78 |
| Oncomine Gene Expression Signatures | 11640152 | Prostate Type - Top 10% under-expressed in Metastatic Prostate Cancer (Vanaja) | 1720 | 7.00E−20 | 1.01E−17 | 1.8 |
| Oncomine Gene Expression Signatures | 22240116 | Colon Carcinoma Grade - Top 10% under-expressed in 4 (Bittner) | 1880 | 6.80E−19 | 8.11E−17 | 1.75 |
| Oncomine Gene Expression Signatures | 11632752 | Cancer Type - v1 - Top 10% under-expressed in Metastatic Ovarian Carcinoma (Bittner) | 1880 | 7.70E−19 | 8.96E−17 | 1.74 |
| Oncomine Gene Expression Signatures | 40938836 | Bladder Grade - Type - Top 20% under-expressed in High Grade (Sanchez-Carbayo) | 2420 | 1.20E−17 | 1.08E−15 | 1.64 |
| Oncomine Gene Expression Signatures | 22235086 | Breast Carcinoma Type - Top 10% under-expressed in Invasive Ductal (Radvanyi) | 1360 | 2.20E−17 | 1.82E−15 | 1.83 |
| Oncomine Gene Expression Signatures | 22233026 | Breast Carcinoma Estrogen Receptor Status - Top 10% over-expressed in Positive (Richardson) | 1880 | 2.90E−17 | 2.32E−15 | 1.7 |
| Oncomine Gene Expression Signatures | 40937996 | Bladder Progression - Top 20% under-expressed in Progression to T2 (Dyrskjot) | 3260 | 5.20E−17 | 4.04E−15 | 1.54 |
| Oncomine Gene Expression Signatures | 12787382 | Prostate ETS Status - Top 1% over-expressed in ERG over-expression (Glinsky) | 124 | 6.40E−17 | 4.47E−15 | 4.94 |
| Oncomine Gene Expression Signatures | 58088056 | Melanoma Primary__vs__met - Top 20% under-expressed in metastatic lines (Hayward) | 3680 | 1.40E−16 | 9.10E−15 | 1.51 |
| Oncomine Gene Expression Signatures | 40934586 | Bladder Grade - Top 10% over-expressed in High Grade (Dyrskjot) | 1630 | 2.00E−16 | 1.22E−14 | 1.72 |
| Oncomine Gene Expression Signatures | 8453622 | Prostate Type - Top 10% under-expressed in Metastatic (Vanaja) | 1720 | 2.80E−16 | 1.62E−14 | 1.7 |
| Oncomine Gene Expression Signatures | 39219806 | Prostate Adenocarcinoma ETS status - Top 20% over-expressed in ERG, ETV1 (Vanaja) | 3380 | 3.60E−15 | 1.74E−13 | 1.49 |
| Oncomine Gene Expression Signatures | 8464292 | Colon MLH1 Methylation - Top 10% under-expressed in Positive (Koinuma) | 1720 | 5.40E−15 | 2.52E−13 | 1.66 |
| Oncomine Gene Expression Signatures | 21463266 | Oligodendroglioma Grade - Top 10% under-expressed in Grade 3 (Sun) | 1880 | 6.20E−15 | 2.81E−13 | 1.64 |
| Oncomine Gene Expression Signatures | 40938676 | Bladder Stage - Type - Top 20% under-expressed in Stage T4, Cancer (Sanchez-Carbayo) | 2420 | 8.40E−15 | 3.60E−13 | 1.57 |
| Oncomine Gene Expression Signatures | 40938006 | Bladder Progression (y/n) - Top 20% under-expressed in Progression (Dyrskjot) | 3260 | 1.80E−14 | 7.55E−13 | 1.48 |
| Oncomine Gene Expression Signatures | 12787532 | Prostate ETS Status - Top 1% over-expressed in ERG over-expression (Glinsky) | 124 | 3.00E−14 | 1.20E−12 | 4.33 |
| Oncomine Gene Expression Signatures | 8467232 | Breast Carcinoma Survival - 5 years - Top 10% under-expressed in Dead (Pawitan) | 1720 | 6.20E−14 | 2.28E−12 | 1.63 |
| Literature-defined Concepts | 49520036 | Up-regulated genes in luminal breast cell lines compared to basal breast cell lines | 347 | 6.30E−14 | 3.50E−12 | 2.59 |
| Oncomine Gene Expression Signatures | 22210716 | Breast Carcinoma Grade - Top 10% under-expressed in 3 (Bittner) | 1880 | 6.50E−14 | 2.37E−12 | 1.61 |

TABLE 5-continued

MCM analysis of AR-bound genes in VCaP cells

| Group Type | Group ID | Group Name | Group Size | P-Value | Q-Value | Odds Ratio |
|---|---|---|---|---|---|---|
| Literature-defined Concepts | 148292 | SUZ12 occupancy in embryonic fibroblasts | 1115 | 7.80E−14 | 3.97E−12 | 1.91 |
| Literature-defined Concepts | 148284 | EED occupancy in stem cells | 1066 | 1.40E−13 | 6.55E−12 | 1.91 |
| Oncomine Gene Expression Signatures | 40936866 | Bladder Progression - Top 20% over-expressed in Progression to T2 (Dyrskjot) | 3260 | 1.40E−13 | 5.01E−12 | 1.46 |
| Literature-defined Concepts | 61201506 | Down-regulated genes in human prostate cancer cell line LNCaP treated with R1881 (synthetic androgen) | 323 | 2.30E−13 | 1.03E−11 | 2.53 |
| Oncomine Gene Expression Signatures | 49442886 | Prostate ETS Status - Top 10% over-expressed in ERG (Yang) | 1210 | 4.20E−13 | 1.36E−11 | 1.72 |
| Oncomine Gene Expression Signatures | 51554656 | Melanoma Primary_vs_met_vs_NOS - Top 20% over-expressed in metastatic lines (Hayward) | 3680 | 5.00E−13 | 1.61E−11 | 1.44 |
| Literature-defined Concepts | 49519286 | Down-regulated genes in prostate cancer after 3 months of androgen ablation therapy | 203 | 1.10E−12 | 4.42E−11 | 3.14 |
| Oncomine Gene Expression Signatures | 8620062 | Ovarian Survival - 5 years - Top 10% over-expressed in Dead of Disease (Lu) | 1700 | 2.40E−12 | 6.84E−11 | 1.58 |
| Oncomine Gene Expression Signatures | 8467222 | Astrocytoma Survival - 5 years - Top 10% under-expressed in Dead (Phillips) | 1720 | 1.90E−11 | 4.13E−10 | 1.55 |
| Oncomine Gene Expression Signatures | 8437612 | Astrocytoma Primary/Recurrent - Top 10% under-expressed in Recurrent (Phillips) | 1720 | 5.90E−11 | 1.13E−09 | 1.54 |
| Literature-defined Concepts | 104368 | Upregulated genes in prostate cancer cells in response to synthetic androgen R1881 | 301 | 7.20E−11 | 2.39E−09 | 2.36 |
| Oncomine Gene Expression Signatures | 8449382 | Lung Carcinoma 3 Year Survival - Top 10% under-expressed in Dead (Bild) | 1880 | 1.10E−10 | 2.03E−09 | 1.51 |
| My Concepts | 23624076 | 3mH3K27 occupancy in metastatic prostate tumors | 1253 | 2.00E−10 | 4.61E−10 | 1.7 |

TABLE 6

MCM analysis of ERG-bound genes in VCaP cells

| Group Type | Group ID | Group Name | Group Size | P-Value | Q-Value | Odds Ratio |
|---|---|---|---|---|---|---|
| My Concepts | 70857755 | ERG-bound in VCaP | 2891 | ######## | 2.03E−98 | 69467839 |
| My Concepts | 70857675 | ERG-bound in RWPE + ERG | 2895 | ######## | 3.62E−99 | 15.45 |
| Transfac TF Matrix - 1000bp | 104952 | c-Ets-1(p54) | 1308 | ######## | 4.51E−98 | 5.02 |
| Transfac TF Matrix - 1000bp | 112968 | NRF-2 | 1233 | ######## | 2.26E−98 | 4.98 |
| Transfac TF Matrix - 1000bp | 107640 | Elk-1 | 1386 | ######## | 1.52E−98 | 4.82 |
| Transfac TF Matrix - 1000bp | 112595 | GABP | 1403 | ######## | 1.20E−98 | 4.01 |
| My Concepts | 70857715 | AR-bound in VCaP | 2893 | ######## | 2.40E−99 | 3.4 |
| My Concepts | 70857635 | AR-bound in LNCaP | 2889 | 4.70E−39 | 3.42E−38 | 2.08 |
| Oncomine Gene Expression Signatures | 49442936 | Prostate Tissue Type - Top 20% over-expressed in Prostate Carcinoma (Yang) | 2420 | 1.90E−28 | 1.07E−25 | 1.87 |
| Oncomine Gene Expression Signatures | 8453582 | Prostate Adenocarcinoma Grade - Top 10% over-expressed in Metastatic (Vanaja) | 1720 | 2.10E−27 | 9.15E−25 | 1.98 |
| Oncomine Gene Expression Signatures | 8453592 | Prostate Type - Top 10% over-expressed in Metastatic (Vanaja) | 1720 | 2.40E−24 | 5.80E−22 | 1.9 |
| Oncomine Gene Expression Signatures | 58926376 | Melanoma Type - Top 20% over-expressed in Lymph Node Metastasis, Metastatic Growth | 3680 | 5.00E−24 | 1.16E−21 | 1.64 |

TABLE 6-continued

MCM analysis of ERG-bound genes in VCaP cells

| Group Type | Group ID | Group Name | Group Size | P-Value | Q-Value | Odds Ratio |
|---|---|---|---|---|---|---|
| | | Phase Melanoma, Metastatic Melanoma Culture, Vertical Growth Phase Melanoma (Smith) | | | | |
| Oncomine Gene Expression Signatures | 22210396 | Breast Carcinoma Grade - Top 10% over-expressed in 3 (Bittner) | 1880 | 3.30E−22 | 6.00E−20 | 1.82 |
| Oncomine Gene Expression Signatures | 22242446 | Bladder Type - Top 10% over-expressed in Invasive Transitional Cell Carcinoma (Dyrskjot) | 1240 | 2.60E−21 | 4.13E−19 | 1.98 |
| Oncomine Gene Expression Signatures | 22231476 | Melanoma Tissue Group - Top 10% over-expressed in Advanced Stage (Smith) | 1880 | 1.20E−20 | 1.64E−18 | 1.79 |
| Oncomine Gene Expression Signatures | 40936826 | Bladder Recurrence - cis present - Top 20% over-expressed in cis, recurrence (Dyrskjot) | 905 | 1.10E−18 | 1.08E−16 | 2.24 |
| GO Biological Process | 102314 | protein biosynthesis | 265 | 1.90E−17 | 3.59E−14 | 3.26 |
| Oncomine Gene Expression Signatures | 120991 | Breast Carcinoma Disease Free Survival - 5 years - Top 10% over-expressed in Relapse (vandeVijver) | 1480 | 2.90E−17 | 2.46E−15 | 1.78 |
| Oncomine Gene Expression Signatures | 40937706 | Bladder Grade - Type - Top 20% over-expressed in High Grade (Sanchez-Carbayo) | 2420 | 9.00E−17 | 7.32E−15 | 1.61 |
| KEGG Pathway | 100478 | Ribosome | 85 | 1.50E−16 | 2.52E−14 | 6.79 |
| Oncomine Gene Expression Signatures | 21463186 | Oligodendroglioma Grade - Top 10% over-expressed in Grade 3 (Sun) | 1880 | 3.00E−16 | 2.24E−14 | 1.67 |
| Oncomine Gene Expression Signatures | 8467182 | Astrocytoma Survival - 5 years - Top 10% over-expressed in Dead (Phillips) | 1720 | 1.00E−15 | 6.89E−14 | 1.68 |
| Oncomine Gene Expression Signatures | 8467192 | Breast Carcinoma Survival - 5 years - Top 10% over-expressed in Dead (Pawitan) | 1720 | 2.30E−15 | 1.45E−13 | 1.67 |
| Oncomine Gene Expression Signatures | 12787652 | Prostate ETS Status - Top 10% over-expressed in ERG over-expression (Glinsky) | 1240 | 3.00E−14 | 1.71E−12 | 1.75 |
| Oncomine Gene Expression Signatures | 131411 | ER+ Breast Carcinoma Disease Free Survival - 5 years - Top 10% over-expressed in Relapse (vandeVijver) | 1480 | 6.50E−14 | 3.51E−12 | 1.67 |
| Oncomine Gene Expression Signatures | 22212096 | Prostate Adenocarcinoma Type - Top 10% over-expressed in Metastasic Prostate Cancer (Holzbeierlein) | 470 | 2.00E−13 | 9.71E−12 | 2.26 |
| Oncomine Gene Expression Signatures | 22231336 | Melanoma Culture Type - Top 10% over-expressed in | 1240 | 5.10E−13 | 2.36E−11 | 1.7 |

TABLE 6-continued

MCM analysis of ERG-bound genes in VCaP cells

| Group Type | Group ID | Group Name | Group Size | P-Value | Q-Value | Odds Ratio |
|---|---|---|---|---|---|---|
| Oncomine Gene Expression Signatures | 39219806 | Metastasic Melanoma (Hoek) Prostate Adenocarcinoma ETS status - Top 20% over-expressed in ERG, ETV1 (Vanaja) | 3380 | 1.60E−12 | 6.65E−11 | 1.43 |
| GO Molecular Function | 110024 | RNA binding | 458 | 2.50E−12 | 2.62E−09 | 2.21 |
| Connectivity Map | 21639906 | MCF Cells Treatment - Top 5% under-expressed in 506, MCF7 treated with estradiol (.00000001 M) for 6 h (Lamb) | 620 | 2.70E−12 | 4.13E−09 | 1.99 |
| Oncomine Gene Expression Signatures | 12787462 | Prostate ETS Status - Top 10% over-expressed in ERG over-expression (Glinsky) | 1240 | 7.30E−12 | 2.86E−10 | 1.66 |
| Oncomine Gene Expression Signatures | 123612 | Prostate Type - Top 10% over-expressed in Metastatic Prostate Cancer (LaTulippe) | 780 | 8.30E−12 | 3.20E−10 | 1.86 |
| Oncomine Gene Expression Signatures | 22211976 | Breast Carcinoma Estrogen Receptor Status - Top 10% over-expressed in Positive (Yu) | 884 | 8.50E−12 | 3.22E−10 | 1.78 |
| Literature-defined Concepts | 148289 | Upregulated in Human Embryonic Stem Cells vs Differentiated Counterparts | 871 | 8.80E−12 | 5.31E−10 | 1.92 |
| Oncomine Gene Expression Signatures | 12787452 | Prostate ETS Status - Top 10% over-expressed in ERG over-expression, ETV1 over-expression (Glinsky) | 1240 | 1.10E−11 | 4.11E−10 | 1.65 |
| Oncomine Gene Expression Signatures | 40936846 | Bladder Grade - Top 20% over-expressed in High Grade (Dyrskjot) | 3260 | 4.90E−11 | 1.60E−09 | 1.4 |
| Oncomine Gene Expression Signatures | 40938506 | Bladder Type - Top 20% under-expressed in Invasive (Modlich) | 2420 | 1.10E−10 | 3.38E−09 | 1.45 |

TABLE 7

MCM analysis of ERG-bound genes in metastatic prostate caner tissue

| Group Type | Group ID SEQ | Group Name | Group Size | P-Value | Q-Value | Odds Ratio |
|---|---|---|---|---|---|---|
| My Concepts | 73995065 | tissue-ERG | 1472 | 1.00E−100 | 2.03E−98 | 37459456 |
| My Concepts | 73995015 | tissue-AR | 2892 | 1.10E−100 | 1.08E−98 | 15.85 |
| Oncomine Gene Expression Signatures | 72365935 | Prostate Type - Top 5% over-expressed in Metastatic Prostate Carcinoma | 505 | 1.10E−100 | 6.17E−97 | 11.03 |
| My Concepts | 70857755 | VCaP-ERG | 2891 | 1.20E−100 | 6.01E−99 | 6.39 |
| My Concepts | 70857675 | RWPE-ERG | 2895 | 1.30E−100 | 5.10E−99 | 4.89 |
| My Concepts | 70857715 | VCaP-AR | 2893 | 1.30E−100 | 3.75E−99 | 4.42 |
| My Concepts | 70857635 | LNCaP-AR | 2889 | 2.20E−96 | 5.59E−95 | 4.04 |
| Oncomine Gene Expression Signatures | 71321925 | Metastatic Prostate Carcinoma Mets ETS 2 - Top 20% over-expressed in ERG+ | 3140 | 6.80E−43 | 1.81E−40 | 2.43 |
| Transfac TF Matrix - 1000bp | 104952 | c-Ets-1(p54) | 1308 | 1.20E−24 | 4.27E−22 | 2.44 |
| Oncomine Gene Expression Signatures | 8453582 | Prostate Adenocarcinoma Grade - Top 10% over-expressed in Metastatic (Vanaja) | 1720 | 1.20E−20 | 2.01E−18 | 2.13 |

TABLE 7-continued

MCM analysis of ERG-bound genes in metastatic prostate caner tissue

| Group Type | Group ID SEQ | Group Name | Group Size | P-Value | Q-Value | Odds Ratio |
|---|---|---|---|---|---|---|
| Oncomine Gene Expression Signatures | 72366945 | Prostate Type - ETS Status - Top 20% over-expressed in Localized Prostate Carcinoma, ERG+ | 3510 | 1.40E-18 | 1.81E-16 | 1.78 |

TABLE 8

Oligonucleotide sequences used in this study.

| Target | Sequence | SEQ ID NO |
|---|---|---|
| AR_pF2 | GGGTGATTTTGCCTTTGAGA | 1 |
| AR_pR2 | CTGCCTTTCTTCCTGTCTGG | 2 |
| AR F1 | CAGTGGATGGGCTGAAAAAT | 3 |
| AR R1 | GGAGCTTGGTGAGCTGGTAG | 4 |
| C15ORF21 pF4 | CCTCCACCGAAAGTGTGTCT | 5 |
| C15ORF21 pR4 | CAATTTGCCAGAGACAAGCA | 6 |
| TMPRSS2_pF1 | tggagctagtgctgcatgtc | 7 |
| TMPRSS2_pR1 | ctgccttgctgtgtgaaaaa | 8 |
| TMPRSS2 pF2 | GGTAAACTCTCCCTGCCACA | 9 |
| TMPRSS2 pR2 | TACTCCAGGAAGTGGGGATG | 10 |
| SLC45A3_pF1 | actcccctgagctctccttc | 11 |
| SLC45A3_pR1 | gggaaagaacactgggaaca | 12 |
| HNRPA2B1_pF1 | tcccccaacatttagaaaagc | 13 |
| HNRPA2B1_pR1 | agcgttggaagagttgttgg | 14 |
| TMPRSS2_pF1 | tggagctagtgctgcatgtc | 15 |
| TMPRSS2_pR1 | ctgccttgctgtgtgaaaaa | 16 |
| HERV-K_pF1 | CGGCTGTTTGtgtagggaaa | 17 |

TABLE 8-continued

Oligonucleotide sequences used in this study.

| Target | Sequence | SEQ ID NO |
|---|---|---|
| HERV-K_pR1 | atcgtgcccctgattaatgg | 18 |
| GAPDH_F1 | TGCACCACCAACTGCTTAGC | 19 |
| GAPDH_R1 | GGCATGGACTGTGGTCATGAG | 20 |
| HMBS_F1 | GATGGGCAACTGTACCTGACTGGA | 21 |
| HMBS_R1 | TGGGGCCCTCGTGGAATGTTA | 22 |
| Both_ERG_F1 | CGCAGAGTTATCGTGCCAGCAGAT | 23 |
| Both_ERG_R1 | CCATATTCTTTCACCGCCCACTCC | 24 |
| TMPRSS2-ERG_F1 | TAGGCGCGAGCTAAGCAGGAG | 25 |
| TMPRSS2-ERG_R1 | GTAGGCACACTCAAACAACGACTGG | 26 |
| wildtype-ERG_F1 | GCTCTAAACAACCTCATCAAAACTACTT | 27 |
| wildtype-ERG_R1 | CTTAATAGTGCTGGCCATAATGCG | 28 |
| wildtype-ERG siRNA | UGG UCA GAG AGA AGC AAU A | 29 |

EXAMPLE 2 siRNA Targeting siRNAs were designed that targeted ERG or TMPRSS2-ERG fusions. Exemplary oligonucleotides are shown in Table 9.

TABLE 9

| Name | Sequence | Additional information | SEQ ID NO |
|---|---|---|---|
| Custom WTShort duplex, 1 of 4 | CGC AUU AUG GCC AGC ACU A | Targets WT-ERG short only | 30 |
| Custom WTShort duplex, 2 of 4 | CAA UAA ACU UGA UCG CAU U | Targets WT-ERG short only | 31 |
| Custom WTShort duplex, 3 of 4 | UGG UCA GAG AGA AGC AAU A | Targets WT-ERG short only | 32 |
| Custom WTShort duplex, 4 of 4 | CAA AAC UAC UUU CUG GUC A | Targets WT-ERG short only | 33 |
| Custom WT-ERG-Long duplex, 1 of 3 | UGG UAG AUG GGC UGG CUU A | Targets WT-ERG long only | 34 |
| Custom WT-ERG-Long duplex, 2 of 3 | CAA CUA AAG CCG UCA GGU U | Targets WT-ERG long only | 35 |
| Custom WT-ERG-Long duplex, 3 of 3 | CAA AUG ACU CAC AGA GAA A | Targets WT-ERG long only | 36 |

TABLE 9-continued

| Name | Sequence | Additional information | SEQ ID NO |
|---|---|---|---|
| Custom FUS-ERG duplex, 1 of 5 | GCA GGA AGC CUU AUC AGU U | Targets TMPRSS2-ERG fusion (the fusion observed in VCap cells) | 37 |
| Custom FUS-ERG duplex, 2 of 5 | CAG GAA GCC UUA UCA GUU G | Targets TMPRSS2-ERG fusion (the fusion observed in VCap cells) | 38 |
| Custom FUS-ERG duplex, 3 of 5 | GGC AGG AAG CCU UAU CAG U | Targets TMPRSS2-ERG fusion (the fusion observed in VCap cells) | 39 |
| Custom FUS-ERG duplex, 4 of 5 | CGG CAG GAA GCC UUA UCA G | Targets TMPRSS2-ERG fusion (the fusion observed in VCap cells) | 40 |
| Custom FUS-ERG duplex, 5 of 5 | GCG GCA GGA AGC CUU AUC A | Targets TMPRSS2-ERG fusion (the fusion observed in VCap cells) | 41 |
| D-003886-01 (Dharmacon) | D-003886-01 (Dharmacon) | Targets all isoforms of ERG | |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method of inhibiting the expression of an ERG gene in a cell, comprising contacting said cell with an siRNA against ERG, wherein said siRNA has the sequence of one of SEQ ID NOS: 30-41.

2. The method of claim 1, wherein said cell is a cancer cell.

3. The method of claim 2, wherein said cancer cell is a prostate cancer cell.

4. The method of claim 1, wherein said cell is in vivo.

5. The method of claim 4, wherein said cell is in an animal.

6. The method of claim 5, wherein said animal is a human.

7. The method of claim 1, wherein said cell is ex vivo.

8. The method of claim 1, wherein said ERG gene is fused to TMPRSS2.

9. A kit, comprising a pharmaceutical composition that inhibits the expression of an ERG gene in a cell, wherein said composition comprises an siRNA against ERG, and wherein said siRNA has the sequence of one of SEQ ID NOS: 30-41.

* * * * *

SEQUENCE LISTING

```
<160> NUMBER OF SEQ ID NOS: 44

<210> SEQ ID NO 1
<211> LENGTH: 20
<212> TYPE: DNA
<213> ORGANISM: Homo sapiens

<400> SEQUENCE: 1
gggtgatttt gcctttgaga                                              20

<210> SEQ ID NO 2
<211> LENGTH: 20
<212> TYPE: DNA
<213> ORGANISM: Homo sapiens

<400> SEQUENCE: 2
ctgcctttct tcctgtctgg                                              20

<210> SEQ ID NO 3
<211> LENGTH: 20
<212> TYPE: DNA
<213> ORGANISM: Homo sapiens

<400> SEQUENCE: 3
cagtggatgg gctgaaaaat                                              20

<210> SEQ ID NO 4
<211> LENGTH: 20
<212> TYPE: DNA
<213> ORGANISM: Homo sapiens

<400> SEQUENCE: 4
ggagcttggt gagctggtag                                              20
```

```
<210> SEQ ID NO 5
<211> LENGTH: 20
<212> TYPE: DNA
<213> ORGANISM: Homo sapiens

<400> SEQUENCE: 5
cctccaccga aagtgtgtct                                                   20

<210> SEQ ID NO 6
<211> LENGTH: 20
<212> TYPE: DNA
<213> ORGANISM: Homo sapiens

<400> SEQUENCE: 6
caatttgcca gagacaagca                                                   20

<210> SEQ ID NO 7
<211> LENGTH: 20
<212> TYPE: DNA
<213> ORGANISM: Homo sapiens

<400> SEQUENCE: 7
tggagctagt gctgcatgtc                                                   20

<210> SEQ ID NO 8
<211> LENGTH: 20
<212> TYPE: DNA
<213> ORGANISM: Homo sapiens

<400> SEQUENCE: 8
ctgccttgct gtgtgaaaaa                                                   20

<210> SEQ ID NO 9
<211> LENGTH: 20
<212> TYPE: DNA
<213> ORGANISM: Homo sapiens

<400> SEQUENCE: 9
ggtaaactct ccctgccaca                                                   20

<210> SEQ ID NO 10
<211> LENGTH: 20
<212> TYPE: DNA
<213> ORGANISM: Homo sapiens

<400> SEQUENCE: 10
tactccagga agtggggatg                                                   20

<210> SEQ ID NO 11
<211> LENGTH: 20
<212> TYPE: DNA
<213> ORGANISM: Homo sapiens

<400> SEQUENCE: 11
actcccctga gctctccttc                                                   20

<210> SEQ ID NO 12
<211> LENGTH: 20
<212> TYPE: DNA
<213> ORGANISM: Homo sapiens

<400> SEQUENCE: 12
gggaaagaac actgggaaca                                                   20
```

```
<210> SEQ ID NO 13
<211> LENGTH: 21
<212> TYPE: DNA
<213> ORGANISM: Homo sapiens

<400> SEQUENCE: 13
tcccccaaca tttagaaaag c                                              21

<210> SEQ ID NO 14
<211> LENGTH: 20
<212> TYPE: DNA
<213> ORGANISM: Homo sapiens

<400> SEQUENCE: 14
agcgttggaa gagttgttgg                                                20

<210> SEQ ID NO 15
<211> LENGTH: 20
<212> TYPE: DNA
<213> ORGANISM: Homo sapiens

<400> SEQUENCE: 15
tggagctagt gctgcatgtc                                                20

<210> SEQ ID NO 16
<211> LENGTH: 20
<212> TYPE: DNA
<213> ORGANISM: Homo sapiens

<400> SEQUENCE: 16
ctgccttgct gtgtgaaaaa                                                20

<210> SEQ ID NO 17
<211> LENGTH: 20
<212> TYPE: DNA
<213> ORGANISM: Homo sapiens

<400> SEQUENCE: 17
cggctgtttg tgtagggaaa                                                20

<210> SEQ ID NO 18
<211> LENGTH: 20
<212> TYPE: DNA
<213> ORGANISM: Homo sapiens

<400> SEQUENCE: 18
atcgtgcccc tgattaatgg                                                20

<210> SEQ ID NO 19
<211> LENGTH: 20
<212> TYPE: DNA
<213> ORGANISM: Homo sapiens

<400> SEQUENCE: 19
tgcaccacca actgcttagc                                                20

<210> SEQ ID NO 20
<211> LENGTH: 21
<212> TYPE: DNA
<213> ORGANISM: Homo sapiens

<400> SEQUENCE: 20
ggcatggact gtggtcatga g                                              21
```

```
<210> SEQ ID NO 21
<211> LENGTH: 24
<212> TYPE: DNA
<213> ORGANISM: Homo sapiens

<400> SEQUENCE: 21
gatgggcaac tgtacctgac tgga                                              24

<210> SEQ ID NO 22
<211> LENGTH: 21
<212> TYPE: DNA
<213> ORGANISM: Homo sapiens

<400> SEQUENCE: 22
tggggccctc gtggaatgtt a                                                 21

<210> SEQ ID NO 23
<211> LENGTH: 24
<212> TYPE: DNA
<213> ORGANISM: Homo sapiens

<400> SEQUENCE: 23
cgcagagtta tcgtgccagc agat                                              24

<210> SEQ ID NO 24
<211> LENGTH: 24
<212> TYPE: DNA
<213> ORGANISM: Homo sapiens

<400> SEQUENCE: 24
ccatattctt tcaccgccca ctcc                                              24

<210> SEQ ID NO 25
<211> LENGTH: 21
<212> TYPE: DNA
<213> ORGANISM: Homo sapiens

<400> SEQUENCE: 25
taggcgcgag ctaagcagga g                                                 21

<210> SEQ ID NO 26
<211> LENGTH: 25
<212> TYPE: DNA
<213> ORGANISM: Homo sapiens

<400> SEQUENCE: 26
gtaggcacac tcaaacaacg actgg                                             25

<210> SEQ ID NO 27
<211> LENGTH: 28
<212> TYPE: DNA
<213> ORGANISM: Homo sapiens

<400> SEQUENCE: 27
gctctaaaca acctcatcaa aactactt                                          28

<210> SEQ ID NO 28
<211> LENGTH: 24
<212> TYPE: DNA
<213> ORGANISM: Homo sapiens

<400> SEQUENCE: 28
cttaatagtg ctggccataa tgcg                                              24
```

-continued

```
<210> SEQ ID NO 29
<211> LENGTH: 19
<212> TYPE: RNA
<213> ORGANISM: Homo sapiens

<400> SEQUENCE: 29
uggucagaga gaagcaaua                                                   19

<210> SEQ ID NO 30
<211> LENGTH: 19
<212> TYPE: RNA
<213> ORGANISM: Homo sapiens

<400> SEQUENCE: 30
cgcauuaugg ccagcacua                                                   19

<210> SEQ ID NO 31
<211> LENGTH: 19
<212> TYPE: RNA
<213> ORGANISM: Homo sapiens

<400> SEQUENCE: 31
caauaaacuu gaucgcauu                                                   19

<210> SEQ ID NO 32
<211> LENGTH: 19
<212> TYPE: RNA
<213> ORGANISM: Homo sapiens

<400> SEQUENCE: 32
uggucagaga gaagcaaua                                                   19

<210> SEQ ID NO 33
<211> LENGTH: 19
<212> TYPE: RNA
<213> ORGANISM: Homo sapiens

<400> SEQUENCE: 33
caaaacuacu uucugguca                                                   19

<210> SEQ ID NO 34
<211> LENGTH: 19
<212> TYPE: RNA
<213> ORGANISM: Homo sapiens

<400> SEQUENCE: 34
ugguagaugg gcuggcuua                                                   19

<210> SEQ ID NO 35
<211> LENGTH: 19
<212> TYPE: RNA
<213> ORGANISM: Homo sapiens

<400> SEQUENCE: 35
caacuaaagc cgucagguu                                                   19

<210> SEQ ID NO 36
<211> LENGTH: 19
<212> TYPE: RNA
<213> ORGANISM: Homo sapiens

<400> SEQUENCE: 36
caaaugacuc acagagaaa                                                   19
```

```
<210> SEQ ID NO 37
<211> LENGTH: 19
<212> TYPE: RNA
<213> ORGANISM: Homo sapiens

<400> SEQUENCE: 37
gcaggaagcc uuaucaguu                                                    19

<210> SEQ ID NO 38
<211> LENGTH: 19
<212> TYPE: RNA
<213> ORGANISM: Homo sapiens

<400> SEQUENCE: 38
caggaagccu uaucaguug                                                    19

<210> SEQ ID NO 39
<211> LENGTH: 19
<212> TYPE: RNA
<213> ORGANISM: Homo sapiens

<400> SEQUENCE: 39
ggcaggaagc cuuaucagu                                                    19

<210> SEQ ID NO 40
<211> LENGTH: 19
<212> TYPE: RNA
<213> ORGANISM: Homo sapiens

<400> SEQUENCE: 40
cggcaggaag ccuuaucag                                                    19

<210> SEQ ID NO 41
<211> LENGTH: 19
<212> TYPE: RNA
<213> ORGANISM: Homo sapiens

<400> SEQUENCE: 41
gcggcaggaa gccuuauca                                                    19

<210> SEQ ID NO 42
<211> LENGTH: 19
<212> TYPE: RNA
<213> ORGANISM: Homo sapiens

<400> SEQUENCE: 42
uggucagaga gaagcaaua                                                    19

<210> SEQ ID NO 43
<211> LENGTH: 293
<212> TYPE: DNA
<213> ORGANISM: Homo sapiens

<400> SEQUENCE: 43
taggcgcgag ctaagcagga ggcggaggcg gaggcgagg gcgagggcg gggagcgccg          60 cctggagcgc ggcaggaagc cttatcagtt gtgagtgagg accagtcgtt gtttgagtgt       120
gcctacggaa cgcccacacct ggctaagaca gagatgaccg cgtcctcctc cagcgactat      180
ggacagactt ccaagatgag cccacgcgtc cctcagcagg attggctgtc tcaacccca       240 gccagggtca ccatcaaaat ggaatgtaac cctagccagg tgaatggctc aag             293

<210> SEQ ID NO 44
```

```
<211> LENGTH: 303
<212> TYPE: DNA
<213> ORGANISM: Homo sapiens
<220> FEATURE:
<221> NAME/KEY: misc_feature
<222> LOCATION: (21)..(25)
<223> OTHER INFORMATION: n is a, c, g, or t
<220> FEATURE:
<221> NAME/KEY: misc_feature
<222> LOCATION: (106)..(110)
<223> OTHER INFORMATION: n is a, c, g, or t

<400> SEQUENCE: 44
taggcgcgag ctaagcagga nnnnnggcgg aggcggaggc ggagggcgag gggcggggag      60
cgccgcctgg agcgcggcag gaagccttat cagttgtgag tgaggnnnnn accagtcgtt     120
gtttgagtgt gcctacggaa cgccacacct ggctaagaca gagatgaccg cgtcctcctc     180
cagcgactat ggacagactt ccaagatgag cccacgcgtc cctcagcagg attggctgtc     240
tcaaccccca gccagggtca ccatcaaaat ggaatgtaac cctagccagg tgaatggctc     300
aag                                                                  303
```